United States Patent [19]
Barton et al.

[11] Patent Number: 6,114,699
[45] Date of Patent: Sep. 5, 2000

[54] PREDICTION OF TOTAL DIETARY FIBER IN CEREAL PRODUCTS USING NEAR-INFRARED REFLECTANCE SPECTROSCOPY

[75] Inventors: Franklin E. Barton, Bogart; Sandra E Kays, Athens; William R Windham, Watkinsville, all of Ga.

[73] Assignee: The United States of America as represented by the Secretary of Agriculture, Washington, D.C.

[21] Appl. No.: 08/978,761

[22] Filed: Nov. 26, 1997

[51] Int. Cl.$^7$ .................................................. G01N 21/35
[52] U.S. Cl. ............................ 250/339.09; 250/339.12; 250/341.8; 250/341.5; 702/28
[58] Field of Search ...................... 250/339.09, 339.11, 250/339.01, 339.12, 341.5, 341.8; 702/28

[56] References Cited

U.S. PATENT DOCUMENTS

| | | |
|---|---|---|
| 5,132,538 | 7/1992 | Norris . |
| 5,464,981 | 11/1995 | Squyres et al. . |
| 5,592,402 | 1/1997 | Beebe et al. . |
| 5,606,164 | 2/1997 | Price et al. . |
| 5,842,150 | 11/1998 | Renberg et al. ........................ 702/23 |

OTHER PUBLICATIONS

Kays, Sandra E., et al., Prediction of Total Dietary Fiber in Cereal Products Using Near–Infrared Reflectance Spectroscopy, Journal of Agricultural and Food Chemistry, vol. 44, No. 8 (Aug. 1996), pp. 2266–2271.

Baker et al., "The Determination of Fiber in Processed Cereal Foods by Near–Infrared Reflectance Spectroscopy", *Cereal Chem.*, vol. 60(3), pp. 217–219, 1983.

Hruschka et al., "Least–Squares Curve Fitting of Near Infrared Spectra Predicts Protein and Moisture Content of Ground Wheat", *Applied Spectroscopy*, vol. 36(3), pp. 261–265, 1982.

Workman et al., "Review of Chemometrics Applied to Spectroscopy: 1985–95, Part I", *Applied Spectroscopy Reviews*, 31(1&2), pp. 73–124, 1996.

Cowe et al., "The Use of Principal Components in the Analysis of Near–Infrared Spectra", *Applied Spectroscopy*, vol. 39(2), pp. 257–266, 1985.

Tormod Naes et al., "Comparison of Multivariate Calibration and Discriminant Analysis in Evaluating NIR Spectroscopy for Determination of Meat Tenderness", *Applied Spectroscopy*, vol. 51(3), pp. 350–356, 1997.

Haaland et al., "Multivariate Classification of the Infrared Spectra of Cell and Tissue Samples", *Applied Spectroscopy*, vol. 51(3), pp. 340–345, 1997.

(List continued on next page.)

*Primary Examiner*—Constantine Hannaher
*Assistant Examiner*—Albert Gagliardi
*Attorney, Agent, or Firm*—M. Howard Silverstein; John D. Fado; Gail E. Poulos

[57] ABSTRACT

Near-infrared spectroscopic calibration models are developed for the rapid, accurate and non-polluting prediction of the total dietary fiber content in a wide range of cereal products, including mixed grain products, products with high sugar content, products with high crystal sugar content, products with high fat content, and cereal products with high sugar and high fat content.

20 Claims, 31 Drawing Sheets

Microfiche Appendix Included
(7 Microfiche, 450 Pages)

OTHER PUBLICATIONS

Workman et al., "Calculating the Solution for Regression Techniques—Part I: Multivariate Regression Made Simple", *Spectroscopy*, vol. 12(5), pp. 32–36, Jun., 1997.

Windham et al., "Effect of Cereal Product Residual Moisture Contentl on total Dietary Fiber Determined by Near–Infrared Reflectance Spectroscopy", *Journal of Agricultural and Food Chemistry*, vol. 45(1), pp. 140–144, 1997.

Kays et al., "The Use of Near Infrared Spectroscopy to Measure Total Dietary Fiber Content of Cereal Products", *The Proceedings of the 7th International Conference on Near Infrared Spectroscopy*, Montreal, Canada, Aug. 6–11, 1995, published 1996.

Kays et al., "Prediction of Total Dietary Fiber by Near–Infrared Reflectance Spectroscopy in Cereal Products Containing High Sugar and Crystalline Sugar", *Journal of Agricultural and Food Chemistry*, vol. 45(10), pp. 3944–3951, 1997.

Kays et al., "Prediction of Total Dietary Fiber in Cereal Products Using Near–Infrared Reflectance Spectroscopy", *Journal of Agricultural and Food Chemistry*, vol. 44(8), pp. 2266–2271, 1996.

PREDICTION OF TOTAL DIETARY FIBER IN CEREAL PRODUCTS USING NEAR-INFRARED REFLECTANCE SPECTROSCOPY

MICROFICHE APPENDIX

A Microfiche Appendix containing 7 microfiche containing 450 frames is included.

BACKGROUND OF THE INVENTION

1. Field of the Invention

Near-infrared spectroscopic calibration models are developed for the rapid, clean and reliable prediction of the total dietary fiber content in a wide range of cereal products, including mixed grain products and cereal products with high sugar content, high crystal sugar content, high fat content, and high sugar and fat content.

2. Description of the Related Art

The medical and nutritional communities have long recognized the health benefits of a high fiber diet. For many years Americans have been encouraged to increase their consumption of high fiber foods such as vegetables, fruits and whole grain cereal products. To help consumers to make informed and healthful food choices, the Nutrition Labeling and Education Act (NLEA) was created in 1990. This legislation requires that the amount of total dietary fiber present in a product be included on the nutrition label (Code of Federal Regulations, FDA, HHS; 21 CFR §101.9, 1995).

The method currently in use in the United States, Canada, and many European countries for dietary fiber content analysis for nutrition labeling is the AOAC enzymatic-gravimetric total dietary fiber method (*AOAC Official Methods of Analysis*, 15$^{th}$ Ed., "Total Dietary Fiber in Foods: Method"; AOAC: Arlington, Va. 1990 and 1992). The AOAC method has been used with consistent results, over time, and on a wide variety of food products, grains, and fresh fruits and vegetables. However, it is a very time consuming "wet technique" (taking 2–3 days), expensive, and labor intensive. A more rapid method is needed to help industries comply with the NLEA and to help regulatory agencies efficiently monitor industry compliance.

Near-infrared reflectance spectroscopy (NIRS) is rapid, inexpensive, and clean. However, the amount of intelligence which can be derived from a near-infrared spectral scan is limited. In its most basic form, it is known that the near infrared absorbance spectrum of a sample of, e.g., ground grain, may be plotted to depict absorbance as a function of wavelength. The shape of the absorbance spectrum, including relative magnitudes and wavelengths of peak absorbances, may provide a characteristic "fingerprint" of certain analytes in the sample, by means of which the analytes in the sample may be quantified, particularly where the spectral peaks of the analyte in interest in the sample are unmasked and approximately proportional to the concentration of the analyte in the sample.

However, in the field of agricultural products, materials to be analyzed do not have uniform compositions. The constituent in interest may be partially or fully masked by a complex background of other components. It may also be the case that the target "analyte" is not a simple discrete element or compound, but rather a class of compounds not liable to being "fingerprinted". Thus, limitations are quickly reached as to the amount of information that can be expected to be extracted from bare spectral data.

Mathematical tools have been developed to help extract additional information from spectra. Chemometrics has been described as the application of mathematical and statistical methods to extract more useful chemical information from chemical and physical measurement data. Chemometrics has become a necessary tool, applying computerized data analysis techniques to help find deeply hidden relationships between variables among large volumes of raw data (Workman et al, *Applied Spectroscopy Reviews,* 31 (1&2), 73–124 (1996)). Recent advances have lead to new data analysis systems and a new breed of analytical tools—microprocessor controlled "intelligent" instrumentation. Commercially available NIRS instruments are provided with software packages and use one or more of several methods to convert NIR information to percent composition. So it is known to convert reflectance data to data representing log 1/R values, wherein R is reflectivity, which values vary approximately linearly with the concentration of the absorber. From the log 1/R data, the first or second derivative may be determined. Most methods use some linear combination of these values at a few wavelengths ($\leq 10$). The first or second derivative values are inserted into equations in which the coefficients are determined by linear regression on known samples. The resulting measurements have been correlated to easily defined classes of chemical compounds, e.g., oil, protein, and water content of grain samples.

However, even those working in this art would not be able to predict whether NIRS could be used as a predictor for a target analyte as varied and imprecise as "total dietary fiber" in samples as varied as those which the AOAC enzymatic-gravimetric total dietary fiber method routinely analyzes. To compete with the AOAC method, any method would have to be capable of determining total dietary fiber over a wide range of grains and cereal products, even high sugar and/or high fat content products. Mixed grain cereals and cereal products containing high fat and high sugar represent a significant portion of the cereal product market and baking industries. It is well known that NIR spectral properties of cereal products containing high fat or sugar can differ substantially from the spectral properties of other cereal products. For example, the NIR spectra of sucrose, fructose, and glucose differ significantly. If NIRS can not be made to accurately and reliably predict dietary fiber content of most or all types of bakery products, regardless of fat content, sugar type and content, and grain heterogeneity, then it has little or no use as a commercial indicator.

SUMMARY OF THE INVENTION

It is an object of the present invention to provide a method for the rapid, efficient, accurate and non-polluting total dietary fiber content prediction in any of a wide range of cereal products, including mixed grain products, products with high sugar content, products with high crystalline sugar content, products with high fat content, and products with high fat and sugar content, with results comparable to the approved AOAC enzymatic-gravimetric method.

These and other objects of the invention have been achieved by the careful collection of a sufficiently varied and representative data base and the use thereof in the development of calibration models for the prediction of total dietary fiber content of cereal samples.

The present invention was made only after careful analysis of a wide range of grain samples, taking into consideration possible error attributable to variations in particle size, light-particle interaction, moisture, sampling errors, sample selection errors, repack errors, sample non-homogeneity, sample cell orientation differences, temperature variations from measurement to measurement, instrument bandpass and bandshape, and noise characteristics. As a result of intensive and careful analysis the invention provides calibration models, and means of obtaining them, in which near-infrared reflectance spectroscopy is used for rapid and accurate measurement of dietary fiber to a degree of accuracy sufficient to satisfy the Nutrition Labeling and Education Act (NLEA) requirement for nutrition labels on cereal products. Calibrations were obtained using NIRS for the prediction of dietary fiber in a wide range of cereal products, and the calibrations were found to accurately predict the total dietary fiber content of cereal samples. The standard error of performance, coefficient of determination, bias, and slope observed indicated a high degree of accuracy and reliability in determining dietary fiber by NIRS. Furthermore, the NIRS method requires only seconds to make a determination, requires no chemicals, and requires very little sample preparation.

The invention is not limited to any one specific sample set, statistical or mathematical sample selection technique, model development technique, or type of calibration model. It has been found that sample selection and statistical analysis methods for modeling the variance within the calibration data (e.g., PCR, CPCR, PLS, etc.) show sufficiently similar predictive performance that any one can form the basis of a calibration model within the scope of the present invention. What is significant is that a NIRS model can be created with sufficient intelligence to serve as predictor for dietary fiber content, which model can be generic or can focus on one or more of specific grain type, variations in moisture, fat, solids, type of grain, and amount and type of sugar, a single model can be used to predict total dietary fiber.

The foregoing has outlined rather broadly the more pertinent and important features of the present invention in order that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other treatment methodologies for carrying out the same purposes of the present invention. It should also be realized by those skilled in the art that such equivalent structures do not depart from the spirit and scope of the invention as set forth in the appended claims.

BRIEF DESCRIPTION OF THE DRAWINGS

For a fuller understanding of the nature and objects of the present invention reference should be made by the following detailed description taken in with the accompanying drawings in which.

DETAILED DESCRIPTION OF THE INVENTION

Figure 1:
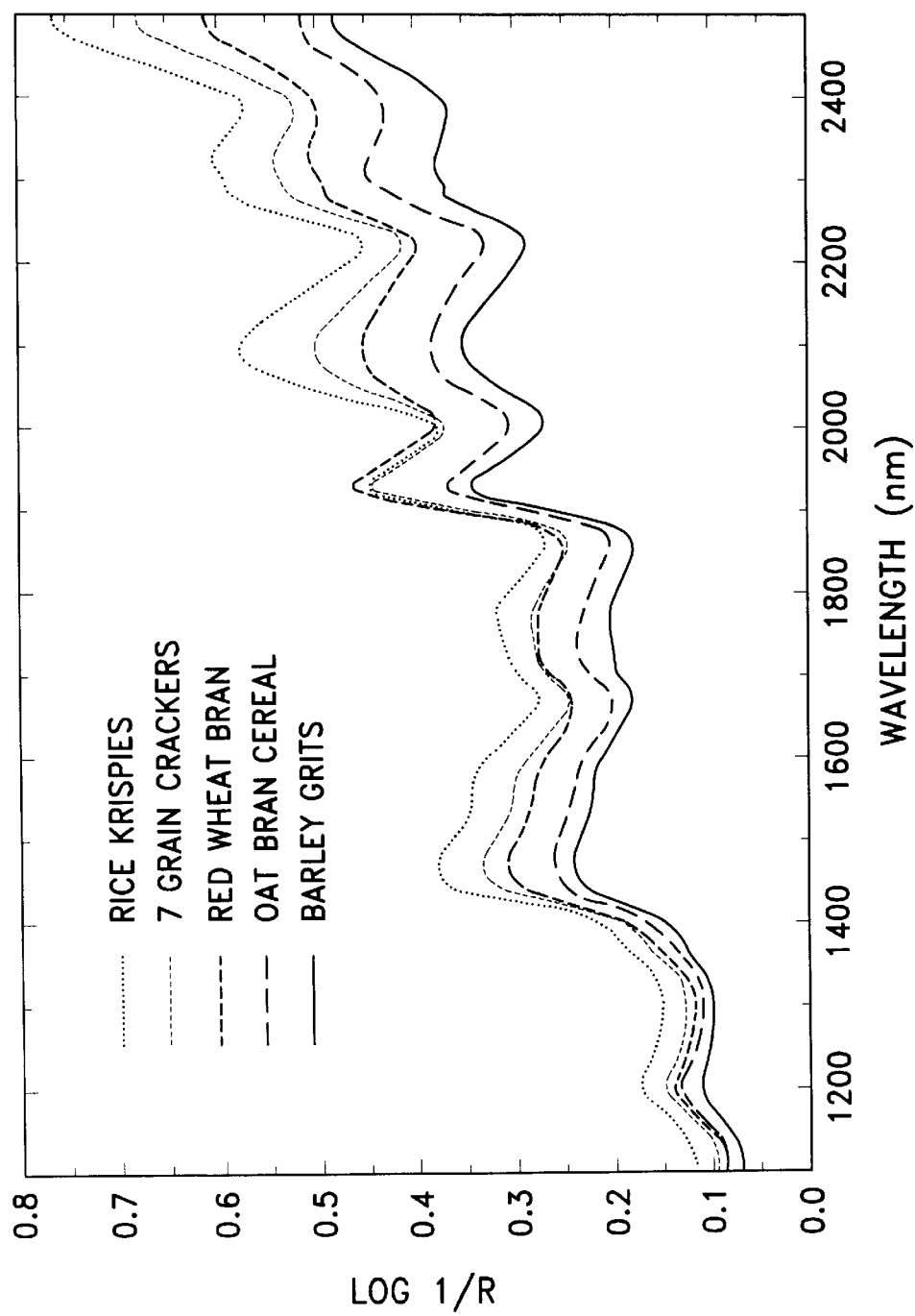
FIG. 1 represents typical NIRS spectra of five cereal samples from the calibration data set.

The present invention applies NIR techniques to the measurement of dietary fiber in a very wide range of dietary fiber values and cereal types, including multi-grain as well as single grain products, and provides accurate, rapid, and environmentally safe methods for the measurement of dietary fiber and for monitoring NLEA compliance.

Dietary Fiber

Dietary fiber has been defined as "the sum of lignin and polysaccharides that are not hydrolyzed by human alimentary enzymes" as postulated by Trowell et al in 1976 and subsequently widely adopted. That is, dietary fiber is the lignin and polysaccharides that remain unaltered and unabsorbed in the digestive tract and which are excreted in their original state. The AOAC total dietary fiber method (*AOAC Official Methods of Analysis*, 15$^{th}$ Ed., "Total Dietary Fiber in Foods: Enzymatic-gravimetric Method"; AOAC: Arlington, Va. 1990 and 1992) is currently used in the United States, Canada, and many European countries for nutrition labeling. It measures non-starch polysaccharides, resistant starch, and lignin remaining after α-amylase, protease, and amyloglucosidase digestion of food samples.

Included in the analyte are other non-hydrolyzed materials such as cutin and waxes, remnants of plants components resistant to human alimentary enzymes, which are often also included as components of dietary fiber.

Chemometrics

Chemometrics is now an established subdiscipline of chemistry. Chemometric tools are powerful enough to completely alter the science of chemistry as it is practiced today. Standard practices for infrared, multivariate, quantitative analysis are described in the "American Society for Testing Materials (ASTM) Practice E1655-94 (1995)", *ASTM Annual Book of Standards,* West Conshohocken, Pa. 19428-2959 USA, Vol. 03.06. *The Association of Official Analytical Chemists (AOAC) Official Methods of Analysis,* 15$^{th}$ Ed. (1990), pp. 74–76, Method 989.03, 1989 presents a near-infrared method for determination of Acid Detergent Fiber and Crude Protein in forage materials using multivariate calibration.

As explained by Cowe et al "The Use of Principal Components in the Analysis of Near-Infrared Spectra", *Applied Spectroscopy* Vol. 39, No. 2, 1985, multiple linear regression can be used to relate changes in spectral intensity (reflectance or transmittance) values at from four points to seven hundred points in the near infra-red spectrum to the concentration of a particular constituent present in a series of representative samples. For any calibration, the critical step is often the identification of a suitable set of four or five near-infrared wavelengths where the combined changes in optical density correlate highly with the constituent in interest. With fixed filter instruments, the number of possible combinations to be tested is relatively small, but with the development of monochromator systems, which typically record each spectrum as a series of several hundred data points, the number of combinations becomes too large for exhaustive testing. As a consequence, a number of techniques have been devised which avoid testing all possible combinations. However, the number of combinations remains large because with highly interrelated spectral intensity values the multiple correlation cannot easily be estimated from the individual wavelength correlations, and the wavelengths selected are often highly dependent upon the which statistical selection technique is used.

Principal Component Analysis (PCA) is one technique for identifying the underlying features of large data sets, and attempts to describe the variation in multi-dimensional data by means of a small number of uncorrelated variables. The underlying concepts and properties of PCA can be illustrated by considering the geometry of a set of samples for which the reflectance energies are measured at two wavelengths only. As principal components are concerned only with the variation in data, all reflectance energies can be plotted as deviations from their mean. Rigid rotation of the plot axis $E_1$ and $E_2$ to maximize the variation along one of the new axis produces the first component $P_1$. The second new axis, $P_2$, which by definition is at right angles to the first, becomes the second principal component. These new axes can be expressed as their linear combinations of the original axis:

$$P_1 = C_{11}E_1 + C_{12}E_2$$

$$P_2 = C_{21}E_1 + C_{22}E_2$$

Where the coefficients $C_{11}$–$C_{22}$ are referred to as "weights" and are always so scaled that the sum of the squared weights for any single component is unity. The weights of any principal component are derived with reference to the rotation which defines the new axis.

In the above example, each sample can be considered as a single point in two dimensions. Where spectral intensity values are measured at several wavelengths, each sample can be taken as a single point in a higher number of dimensions. Each dimension corresponds to an axis or wavelength at which the sample is measured. PCA, in the case of more than two dimensions, involves the rigid rotation of the original axis so that there is a maximum variation along the first new axis, or principal component. The second component is the axis, at right angles to the first, along which there is a maximum residual variation. Subsequent components are defined as the axis, at right angles to all preceding principal components, which in turn explain the greatest amount of "unexplained" variation in the data. This process continues until all the variation has been partitioned into principal components.

When one is using a monochromator, spectra are typically recorded at 700 wavelengths. Thus, each sample is measured at 700 variables or axes, and can be considered a single point in 700 dimensions. Each principal component is therefore defined in terms of the original reflectance values as $$C_1E_1 + C_2E_2 + \ldots + C_{700}E_{700}$$

where $E_i$ denotes the reflectance energy at wavelength i, and $C_I$ denotes the coefficient or weight for energy values at wavelength i.

As a principal component is a linear combination of the original wavelength spectral energy values it can not be measured directly, but must be derived. In this sense principal components are artificial variables. Given the energy values for any sample, we can calculate a principal component value or "score". Denoting the score by S, we have $$S = C_1E_1 + C_2E_2 + \ldots + C_{700}E_{700}$$

For any sample, we can derive a score for each principal component. Since principal components are uncorrelated, the correlation coefficient between the scores of any two components is zero. These scores can be used in regression modeling as alternatives to spectral energy values, and the correlation between a principal component and a constituent is the correlation between the scores on that component and the constituent values.

Principal components can play a valuable role in the interpretation of the spectral data, highlighting the areas of the spectrum which have the greatest influence on the component.

With a database covering a sufficiently representative range of grain samples (which can be generic or can be tailored to the requirements of a specific end user, as discussed below), ranges of dietary fiber content within each type of grain sample, and sample sets with varying amounts of sugar, crystal sugar and fat, sample selection techniques are employed which may be random selection, stratified selection, nearest centroid clustering, and spectral difference calculations, as well as more complex approaches such as correlation analysis between spectra in the wavelength domain, correlation analysis between principal component scores of spectral data, and discriminant analysis between raw and transformed (derivatized) spectra, or between principal component scores of spectra.

As described in Workman et al, *Applied Spectroscopy Reviews,* 31 (1&2), 73–124 (1996), sample selection techniques include random selection, manual subset selection, spectral subtraction methods for "uniqueness" tests, stratified sample selection, wavelength-based discriminant analysis, principal components scores-based discriminant analysis, correlation matching, and small training set problem solving. Preferred among these is correlation matching, with the sensitivity of the technique being increased by pre-treating the spectra as first to higher order derivatives and then calculating the correlation between test and reference data.

Thus, NIRS, aided by chemometrics, has become a useful tool to provide a rapid and accurate method for measuring some constituents of materials without requiring extensive sample preparations and without creating chemical waste (Williams, P. C. and Norris, K. H., 1987 "Near-infrared Technology in the Agricultural and Food Industries"; *Am. Assoc. Cereal Chem.*; St. Paul, Minn.; Marten, et al., 1989 "Near Infrared Reflectance Spectroscopy (NIBS): Analysis of Forage Quality", *U.S.D.A. Agriculture Handbook No. 643*). NIRS has been used successfully to determine moisture and protein content (Hruschka et al., "Least-squares Curve Fitting of Near Infrared Spectra Predicts Protein and Moisture Content of Ground Wheat", *Applied Spectroscopy*, Vol. 36, No. 3, 1982) and fat, acid detergent fiber, and neutral detergent fiber content (Norris, et al. 1976, "Predicting forage quality by infrared reflectance spectroscopy" *J. Animal Sci.*, 43, 889–897; Williams and Norris, 1987, "Qualitative applications in near-infrared reflectance spectroscopy," Near-infrared Technology in the Agricultural and Food Industries; *Am. Assoc. Cereal Chem.*; St. Pal. Minn., p241–246, 1987; Windham, et al., 1988, "Moisture analysis of forage by near infrared reflectance spectroscopy: Preliminary collaborative study and comparison between Karl Fischer and oven drying reference methods," *J. Assoc. Off. Anal. Chem.* 1988, 71, 256–262; Barton and Windham, 1988, "Determination of acid-detergent fiber and crude protein in forages by near-infrared reflectance spectroscopy: collaborative study," *J. Assoc. Off. Anal. Chem.* 1988, 71, 1162–1167).

Baker reported the successful prediction of neutral detergent fiber content of milled breakfast cereals by NIRS (The determination of fiber in processed cereal foods by near-infrared reflectance spectroscopy, *Cereal Chem.* 1983, 60, 217–219). Williams et al. reported analysis of total, soluble, and insoluble dietary fiber in oat bran products by NIRS (Analysis of oat bran products by near-infrared reflectance spectroscopy, *Cereal Foods World*, 1991, 36, 571–574).

Basic Calibration Model

Many manufacturers process products that contain only one or two types of grains. For these industries a less complex model may suffice. For example, when samples containing oat and wheat only are utilized from the present data set a new calibration is obtained (n=42, data not shown) with only 4 factors, and similar standard error of cross validation, multiple correlation coefficient, and accuracy of prediction as the model derived from the Example 1 complete data set. Thus, calibration development and sample prediction can be successfully achieved of dietary fiber in either homogeneous or heterogeneous groups of products.

Most cereal products contain less than 10% fat and less than 20% sugar. For determination of dietary fiber in these most common cereal products the basic calibration model (total dietary fiber/NIR spectral data set) is all that is required. Such a basic calibration model may be prepared on the basis of only cereal product samples containing less than 10% fat and/or less than 20% sugar. Dietary fiber in high fat/high sugar samples can also be accurately predicted using a calibration model designed for low fat and low sugar cereal products by scanning the sample after extraction of the fat or sugar, rather than scanning the original sample. Thus, for most applications, a simplified calibration model may suffice.

The basic calibration model according to the present invention (not calibrated for high fat and/or high sugar content) developed in accordance with the present invention was based on measurements made using a very wide range of cereal types and dietary fiber values. Included in the set were wheat, oats, rye barley, amaranth, corn, rice and wild rice (both processed and unprocessed). Furthermore, many samples contained several types of grain in a single product.

The basic model was used to predict total dietary fiber in an independent set of samples that had a similar diversity of products and range, mean and standard deviation of dietary fiber values. The diversity of the data set is reflected in the number of factors in the model.

The basic calibration, discussed in greater detail below in association with Example 1, employs nine factors, with 88% of the variability for total dietary fiber modeling being explained by factors 2, 3 and 4. This type of equation has broad utility with manufacturers using multiple grains and multiple grain products and for regulatory agencies monitoring products from many sources.

Briefly, to establish reference values total dietary fiber content of dry milled breakfast cereals, crackers, brans, and flours was first measured in the laboratory by the AOAC enzymatic-gravimetric procedure (AOAC, 991.43) to give reference values. Dietary fiber values ranged from 1.0 to 50.5%. Next, milled cereal samples (n=90) were scanned using an NIRSystems 6500 monochromator (U.S. Pat. No. 4,969,739 to McGee) and ISI software. A dietary fiber calibration was obtained using partial least squares regression. The standard error of cross validation was 1.58% with $R^2=0.99$. Finally, independent samples (n=29) were analyzed in the laboratory and scanned by NIR for equation validation. The standard error for prediction for the validation set was found to be 1.5% with $R^2=0.99$. Accordingly, it was determined that NIR, suitably calibrated and used with the dietary fiber model in accordance with the present invention, provides a rapid and accurate method of measuring total dietary fiber in cereal products.

Although not wishing to be bound by any theoretical explanation of the invention, examination of the individual loadings in the calibration equation indicates that effects related to O—H and C—H groups in the water and carbohydrate bands are most important in the model. The three factors with the highest correlation to dietary fiber have loadings with significant intensity in these regions of the spectrum. It is not known whether the influence of O—H absorption is due to residual water or carbohydrate. Other constituents such as lipid and protein appear to be contributing to the model as shown by the intensity of loadings associated with regions of the spectrum typically associated with aliphatic C—H and protein absorbance (e.g., 2304 and 2052 nm, respectively).

Sugar, Fat, and Sugar and Fat Expanded Calibration Models

Many cereal products, such as sugar-coated cereals, some granolas, muesli, and muffin and cake mixes are high in sugar content. Crystalline sugar has unique spectral characteristics which influence the near-infrared region of the spectrum. Other cereal or bakery products are high in fat. For routine measurement of such materials, a more advanced calibration model may be prepared using cereal sample sets including varying amounts of residual moisture, cereal sample sets including high sugar and crystalline sugar content, and cereal products with high fat content.

Accordingly, modeling was carried out on the basis of additional reference samples having a range of sugar content, crystalline sugar content, and fat contents, and additional NIRS data, as discussed in Examples 2–4 below.

The accuracy of predicting total dietary fiber by NIRS in accordance with the present invention was found to be within the precision required by the Food and Drug Administration (the nutrient content of the composite must be at least equal to 80% of the value for that nutrient declared on the label—Code of Federal Regulations, 1995). This level of accuracy can be easily achieved using NIRS for samples of moderate to high fiber levels. However, below 3% fiber precision tends to decline for any method. The FDA further states that, in respect to the above rule, "no regulatory action will be based on a determination of a nutrient value that falls below this level by a factor less than the variability of the method." Hence, NIRS provides an acceptable method for fiber measurement in a wide cross section of samples.

The present invention will now be discussed by reference to examples.

EXAMPLE 1

Basic Calibration Model

MATERIALS AND METHODS

Instrumentation. Measurements were taken with a NIR-Systems 6500 Monochromator (NIRSystems, Silver Spring, Md.), a visible/near-infrared scanning monochromator having a tungsten source and a holographically ruled grating. Diffusely reflected radiation was detected from 400–2500 nm in 2 nm intervals. The lower wavelength region (400–1098 nm) was observed by a pair of silicon detectors located 20 cm form the surface of the sample cell and at an angle of 45° to the incident beam, and the upper wavelength region (1100–2500 nm) by two pairs of lead sulfide detectors in the same orientation as the silicon detectors, Reference reflectance values were obtained using a ceramic block. Samples were presented in a sample cell that is placed on an oscillating shaft with an axis of rotation parallel to the incident radiation. Each sample was scanned sixteen times.

Reagents. Heat stable α-amylase, A 3306; protease, P3910; amyloglucosidase, A 9913; acid washed celite, C 8656; total dietary fiber control kit, TDF-C10; MES, 2-(N-morpholino)ethanesulfonic acid, M-8250; and TRIS, tris (hydroxymethyl)-aminomethane, T1503 were purchased from Sigma Chemical Co., St. Louis, Mo. Buffer (MES/TRIS, 0.05M) was prepared and adjusted to pH 8.2 at 24° C., although the buffer may be adjusted to pH 8.3 if the temperature is 20° C., and to pH 8.1 if the temperature is 28° C., with interpolation for intermediate temperatures.

Enzyme purity and activity. Purity and activity of α-amylase, protease, and amyloglucosidase used in the AOAC dietary fiber procedure were monitored using the Sigma Total Dietary Fiber Assay Control Kit. Briefly, α-amylase and amyloglucosidase activity were monitored by measuring the recovery of corn or wheat starch, and protease by measuring the recovery of casein in the AOAC total dietary fiber procedure. Contamination by β-glucanase, hemicellulase, and pectinase activity were monitored by measuring the recovery of β-glucan, arabinogalactan, and citrus pectin, respectively.

Samples and Sample Preparation. Cereal and grain products (n=122), including breakfast cereals, crackers, brans, and flours were provided by Canadian Harvest USA L.P. (Cambridge, Minn.) Samples were dry milled to <500 $\mu$m in a cyclone mill (Cyclotec 1093 Sample Mill, Perstorp Analytical, Silver Spring, Md.). After milling, commercial fibers were mixed with several processed cereals to provide samples with high, medium, and low dietary fiber content. Thirteen samples in the calibration set and 4 samples in the validation set were prepared in this way. All samples for calibration and validation contained 10% or less fat and 20% or less sugar.

Reference Laboratory Method for Total Dietary Fiber. Total dietary fiber was measured in the laboratory by the AOAC approved method 991.43. Briefly, duplicate samples of milled cereal products were suspended in MES/TRIS buffer (0.05M, pH 8.2 at 24° C.) and incubated sequentially with heat stable α-amylase (95–100° C., 30 min), protease (60° C., 15 min), and a myloglucosidase (60° C., 15 min, pH 4.5±1) to digest starch and protein. The enzyme digestate was then treated with 4 volumes of 95% ethanol (1hr) to precipitate soluble fiber. The alcohol treated digestate was filtered (Fibertec System, E 1023 Filtration Module, Tecator, Höganäs, Sweden), through borosilicate sintered glass crucibles (40–90 $\mu$m) previously matted with celite, dried and weighed. All crucibles containing celite, residue, or ash were weighed by the hot gravimetric technique. The total dietary fiber residue present in the crucible was washed with alcohol and acetone, dried overnight (105° C.), and weighed. One duplicate from each sample was used for ash determination (495° C. muffle furnace) and the other for protein determination. Protein was determined using the LECO, FP-2000 Protein/Nitrogen Analyzer (LECO® Corporation, St. Joseph, Mich.) by AOAC method 990.03. Dry matter of milled cereal products was determined by the AOAC air oven method 945.14. Samples were weighed by the hot gravimetric technique.

Total dietary fiber percent (TDF %) was calculated as follows:

$$TDF \% = (100/DM) \times 100 \times \{[(R_1+R_2)/2]\text{-protein-ash-blank}\}/[(S_1+S_2)/2]$$

where DM is the percent dry matter, $R_1$ and $R_2$ are the residue weights for duplicate samples and $S_1$ and $S_2$ are sample weights.

Spectroscopic analysis. Dry milled cereal samples were scanned with an NIRSystems 6500 monochromator (NIRSystems, Silver Spring, Md.). Duplicates of each sample were presented in cylindrical sample cells with optical quartz surface and cardboard backing (internal diameter 38 mm, depth 9 mm). Each sample was scanned 16 times, the data averaged, and transformed to $\log_{10}(1/R)$. The duplicate scans of each sample were examined visually for consistency and averaged.

Chemometics. Ninety one cereal samples were scanned for the development of a calibration equation. A commercial spectral analysis program (NIRS3, Infrasoft International, Inc. Port Matilda, Pa.) was used to process the data and develop chemometric models. Partial least squares (PLS) regression was the method selected (Partial least-squares method is discussed in Workman et al, *Applied Spectroscopy Reviews*, 31 (1&2), 73–124 (1996); for example of spectrofluorimetric analysis of mixtures of humic acid and ligninsulfonate, see *Anal. Chem.* 1983, 55, 643–648, Lindberg et al., 1983). Prior to the PLS procedure, $\log_{10}(1/R)$ spectra were transformed with standard normal variate and detrending procedures ("Standard normal variate and de-trending of near-infrared diffuse reflectance spectra", *Appl. Spectros.* 1989, 43, 772–777; Barnes et al., 1989) to remove multiplicative interferences of scatter, and then transformed with second derivative processing (gap=20 nm, smoothing interval=10 nm) to enhance absorption peaks. Data were subsequently centered using the CENTER program, available via NIRS3, which allows centering of samples based on consistent values as well as spectral characteristics, i.e., partial least squares-1 (PLS1, Lindberg et al, 1983). Prior to calibration $\log_{10}(1/R)$ spectra were mean centered, transformed with standard normal variate and detrending procedures ("Standard normal variate and de-trending of near-infrared diffuse reflectance spectra", *Appl. Spectros.* 1989, 43, 772–777, Barnes et al., 1989) to remove multiplicative interferences of scatter, and then transformed with second derivative processing (gap=8 nm, smoothing interval=8 nm). Calibration was performed using modified PLS regression available through NIRS3. The modification to PLS scaled the reference method data and reflectance data at each wavelength to have a standard deviation 1.0 before each PLS regression term ("Population definition, sample selection, and calibration procedures for near infrared reflectance spectroscopy", *Crop Sci.*, 1991, 31, 469–474, Shenk and Westerhaus, 1991; "Population structuring of near infrared spectra and modified partial least squares regression", *Crop Sci.* 1991, 31, 1548–1555, Shenk and Westerhaus, 1991). Cross validation was used to determine the optimum number of PLS factors to use for total dietary fiber prediction ("Assessment, validation and choice of calibration method", In *Multivariate Calibration;* John Whiley and Son: New York, N.Y., Martens and Naes, 1989, pp237–266). Cross validation was performed during model development, whereby one sixth of the calibration samples at a time was temporarily removed from the calibration set and used for prediction. Performance statistics were accumulated for each group of removed samples. The optimal number of factors for total dietary fiber was that which produced a minimum in overall error between modeled and reference values (standard error of cross validation—SECV) for the samples removed during cross validation. The preprocessing transformations used were the optimum required to improve the SECV compared to PLS analysis with untransformed data.

Upon completion of the calibration, the model was validated using an independent set of 31 cereal samples. Model performance was reported as the coefficient of determination ($r^2$), the standard error of performance (SEP), and the average difference between measured and modeled values (bias) ("Data analysis: wavelength selection methods", In Near-infrared Technology in the Agricultural and Food Industries; *Am. Assoc. Cereal Chem.:* St. Paul, Minn., Hruschka, 1987, pp35–54). A third data set with a range in total dietary fiber content of 20–90% (n=4), but containing samples of the same matrix (Snowite Oat Fiber from Canadian Harvest USA L.P. and Common Sense Oat Bran from Kellogg Company) was scanned to observe systematic changes in $\log_{10}(1/R)$ with total dietary fiber content.

Total Dietary Fiber Measured by the Reference Method. The values for total dietary fiber in cereal samples determined by the AOAC enzymatic-gravimetric procedure ranged from <1 to 52% (n=122). The standard error of laboratory determinations for the calibration data set was 0.69%. For the calibration and validation data sets the distribution of samples of each grain type was similar (Tables 1 and 2). Likewise, the range, mean, and standard deviation of total dietary fiber percent, within grain types, were similar for each data set.

TABLE 1

Cereal and Grain Products in the Calibration Data Set.
The Range, Mean, and Standard Deviation (SD) of total Dietary Fiber (TDF) percent.

| Product Type | Number of Products | Range in TDF % | Mean TDF % | SD TDF % |
|---|---|---|---|---|
| Wheat | 27 | 2.9–41.0 | 13.8 | 9.8 |
| Oats | 6 | 8.1–19.0 | 12.7 | 4.4 |
| Corn | 5 | 0.6–13.6 | 5.5 | 5.2 |
| Rice | 10 | 1.0–4.3 | 2.3 | 1.4 |
| Rye | 5 | 15.4–38.4 | 23.2 | 9.3 |
| Barley | 2 | 12.4, 19.4 | 15.9 | — |
| Millet | 2 | 3.0, 3.6 | 3.3 | — |
| Buckwheat | 1 | 5.4 | — | — |
| Multiple Grains | 19 | 5.9–47.6 | 19.9 | 12.7 |
| Commercial Oat or Wheat Fiber & Cereal Product Mixes | 13 | 6.4–52.1 | 30.1 | 14.8 |

TABLE 2

Cereal and Grain Products in the Validation Data Set.
The Range, Mean, and Standard Deviation (SD) of Total Dietary Fiber (TDF) Percent.

| Product Type | Number of Products | Range in TDF % | Mean TDF % | SD TDF % |
|---|---|---|---|---|
| Wheat | 9 | 3.6–43.7 | 14.0 | 13.4 |
| Oats | 2 | 9.9, 15.4 | 12.6 | |
| Corn | 1 | 9.4 | | |
| Rice | 3 | 1.2–2.2 | 1.5 | 0.6 |
| Rye | 4 | 9.7–18.1 | 14.0 | 3.5 |
| Buckwheat | 1 | 5.03 | | |
| Multiple Grains | 8 | 2.0–42.2 | 20.3 | 14.8 |
| Commercial Oat or Wheat Fiber & Cereal Product Mixes | 4 | 25.4–42.8 | 36.5 | 7.7 |

Figure 2:
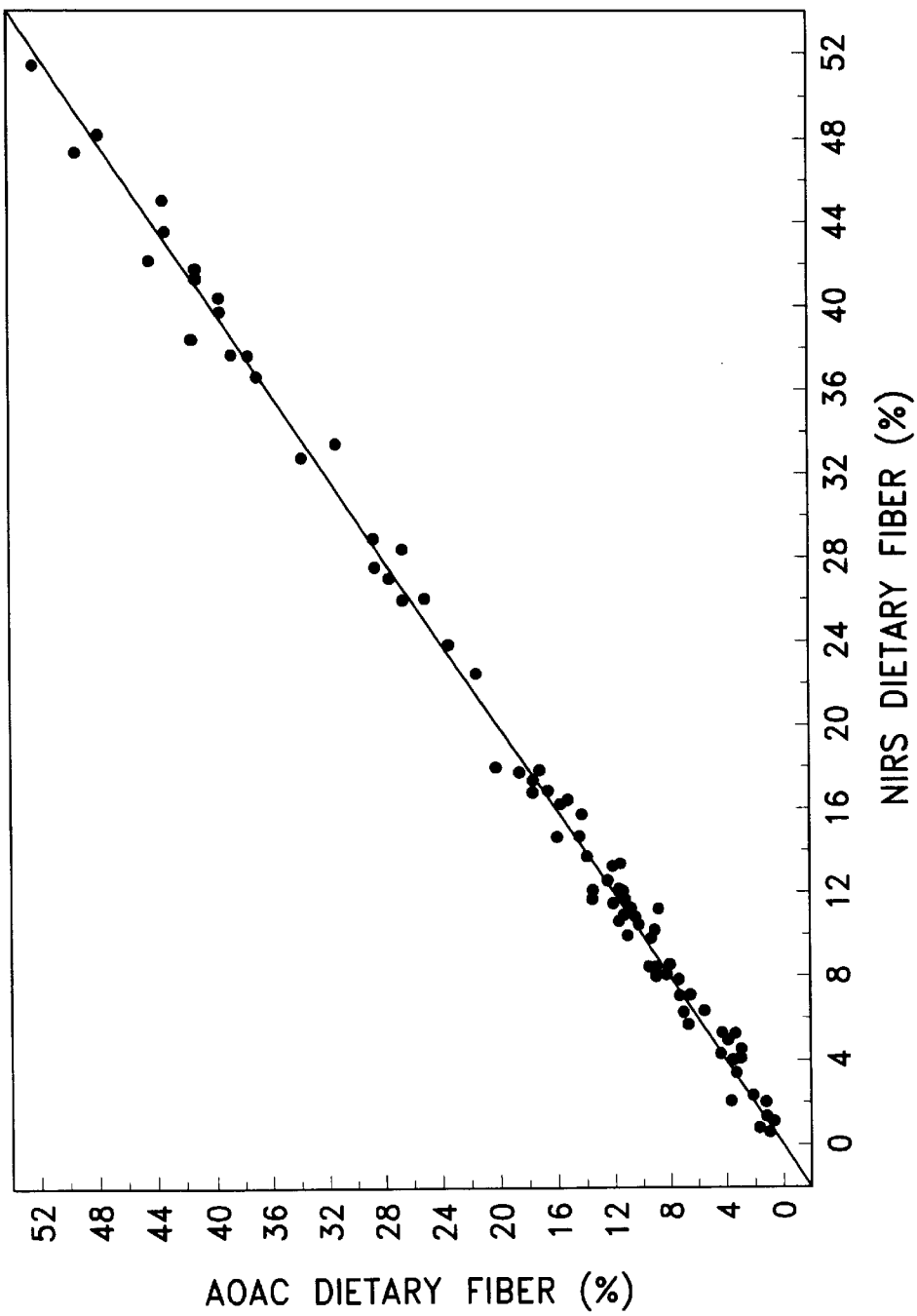
FIG. 2 is a plot of AOAC determined total dietary fiber versus NIRS predicted total dietary fiber for cereal products in the calibration data set (n=90)

NIRS Calibration for Total Dietary Fiber. NIRS spectra obtained were typical of spectra for cereal samples (FIG. 1). Principal component analysis of the spectra indicated that 12 components were required to explain 99% of the variation in the spectral data and that principal components 1 through 3 explained 84% of the variation. One sample was discarded, based on principal component analysis, as a spectral outlier (Mehalanobis distance >3)(for a discussion of a computer technique for outlier recognition, see U.S. Pat. No. 5,592, 402 to Beebe et al.). An NIR calibration equation, using PLS, was obtained for the concentration of total dietary fiber in cereal products. The overall error between modeled and reference values (standard error of cross validation), using six cross validation groups, was 1.58%, with multiple coefficient of determination ($R^2$) of 0.99 (Table 3). Linear regression of AOAC determined dietary fiber against NIRS predicted dietary fiber (Y=0.004+1.00X) gave an intercept and slope not significantly different from 0.0 and 1.0, respectively (p<0.05, FIG. 2). The equation contained 9 factors with scores from factors 2, 3, and 4 having the greatest correlation with total dietary fiber.

TABLE 3

Calibration and Validation Statistics for Dietary Fiber Prediction by NIRS. Mean, Standard Deviation (SD), standard Error of Cross Validation (SECV), and Multiple Coefficient of Determination ($R^2$) for Calibration. Mean, Standard Deviation, Bias, Standard Error of Performance (SEP), and Coefficient of Determination ($r^2$) for Validation.

| | Calibration (N = 90) | | | | Validation (N = 29) | | | | |
|---|---|---|---|---|---|---|---|---|---|
| Method | Mean | SD | SECV | $R^2$ | Mean | SD | Bias | SEP | $r^2$ |
| AOAC | 16.54 | 13.36 | | | 17.43 | 13.77 | | | |
| NIRS | 16.54 | 13.32 | 1.58 | 0.99 | 17.81 | 12.89 | −0.38 | 1.51 | 0.99 |

Figure 3:
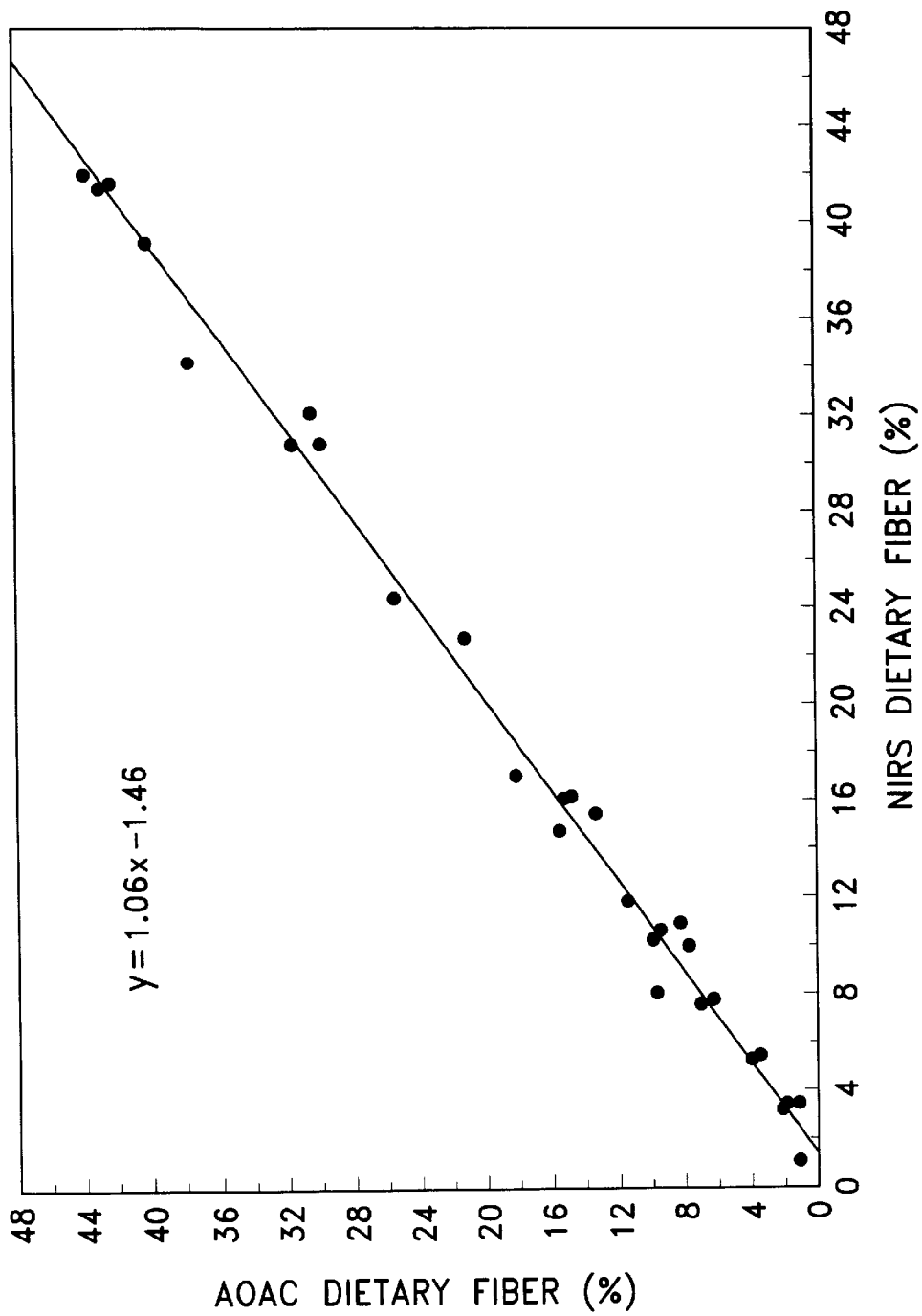
FIG. 3 plots AOAC determined total dietary fiber versus NIRS predicted total dietary fiber for cereal products in the independent validation data set (n=29)

Equation Validation. Independent samples were predicted using the calibration equation. When NIRS predicted values for total dietary fiber were compared statistically with AOAC determined values the standard error of performance was 1.51% and coefficient of determination ($r^2$) 0.99 (Table 3). Linear regression of AOAC determined dietary fiber against NIRS predicted dietary fiber (Y=1.46±1.06X) gave an intercept and slope not significantly different from 0.0 and 1.0, respectively (p<0.05, FIG. 3). Two samples were identified as residual outliers (having a difference between AOAC determined and AOAC predicted values of 2.5 times, or greater, the standard error of the difference between the two values).

Figure 4A:
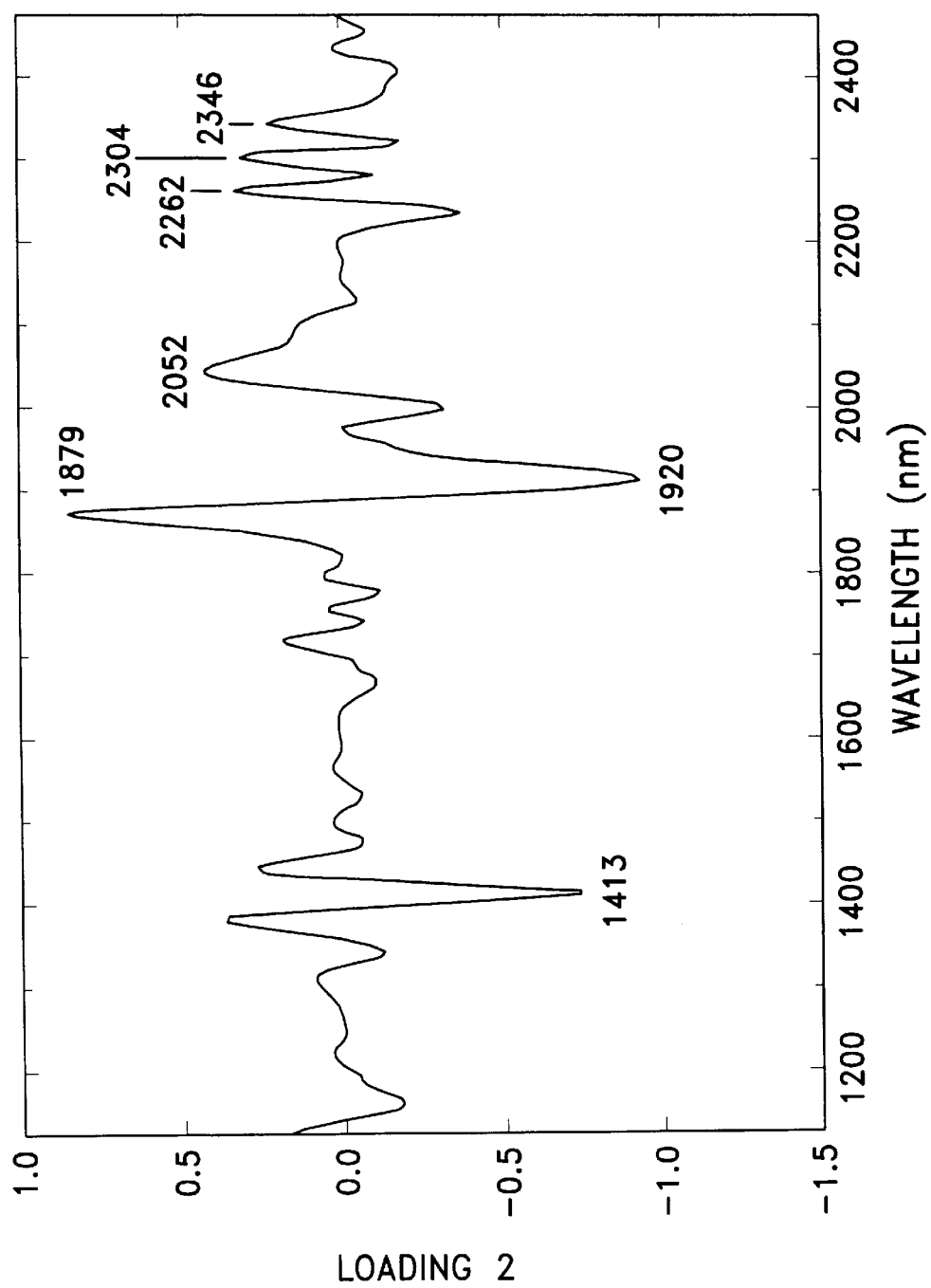
FIGS. 4A, 4B, and 4C represent PLS loading spectra for total dietary fiber in cereal products panels A, B, C represent loadings for factors 2, 3, and 4 respectively.
Figure 4B:
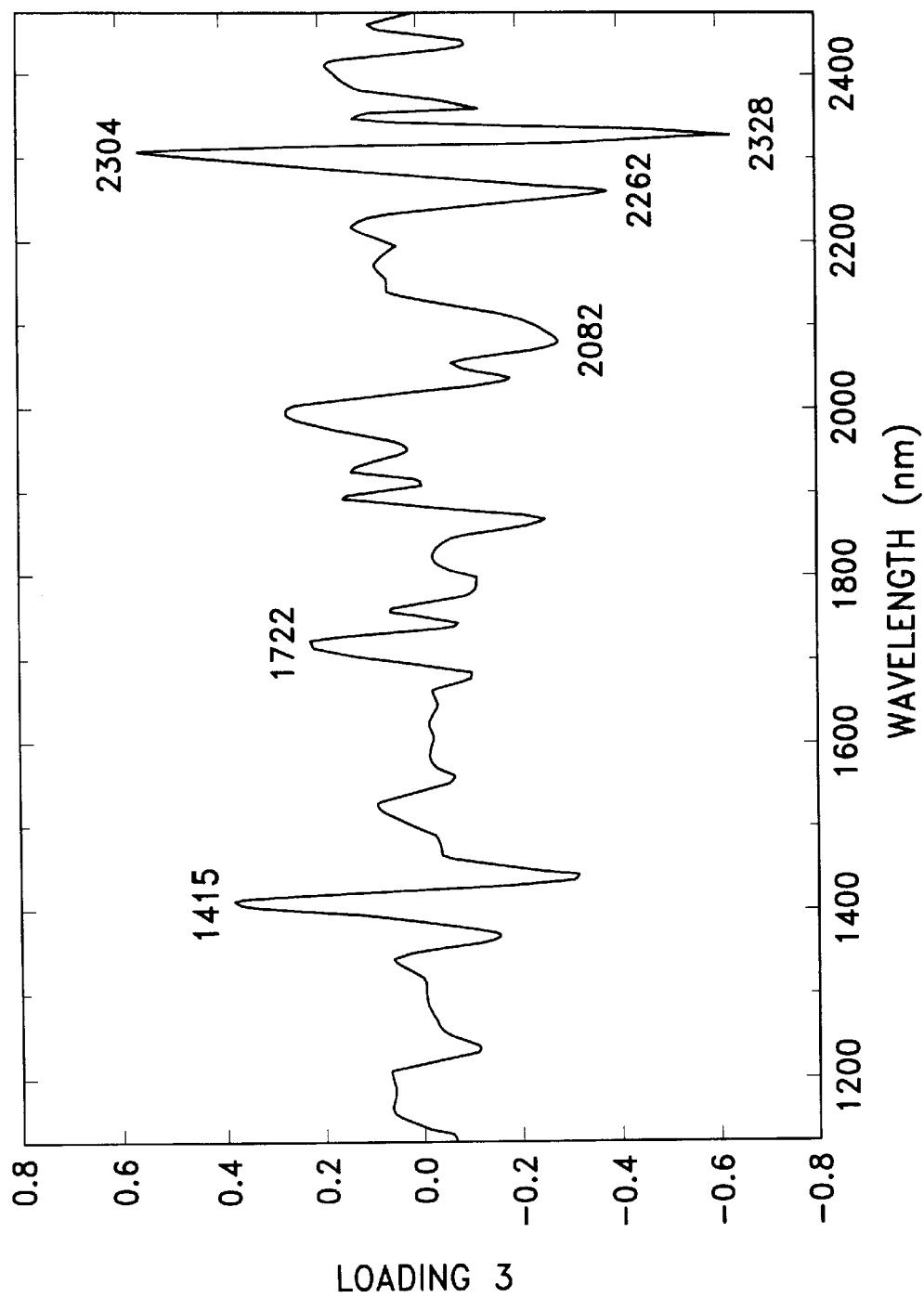
Figure 4C:
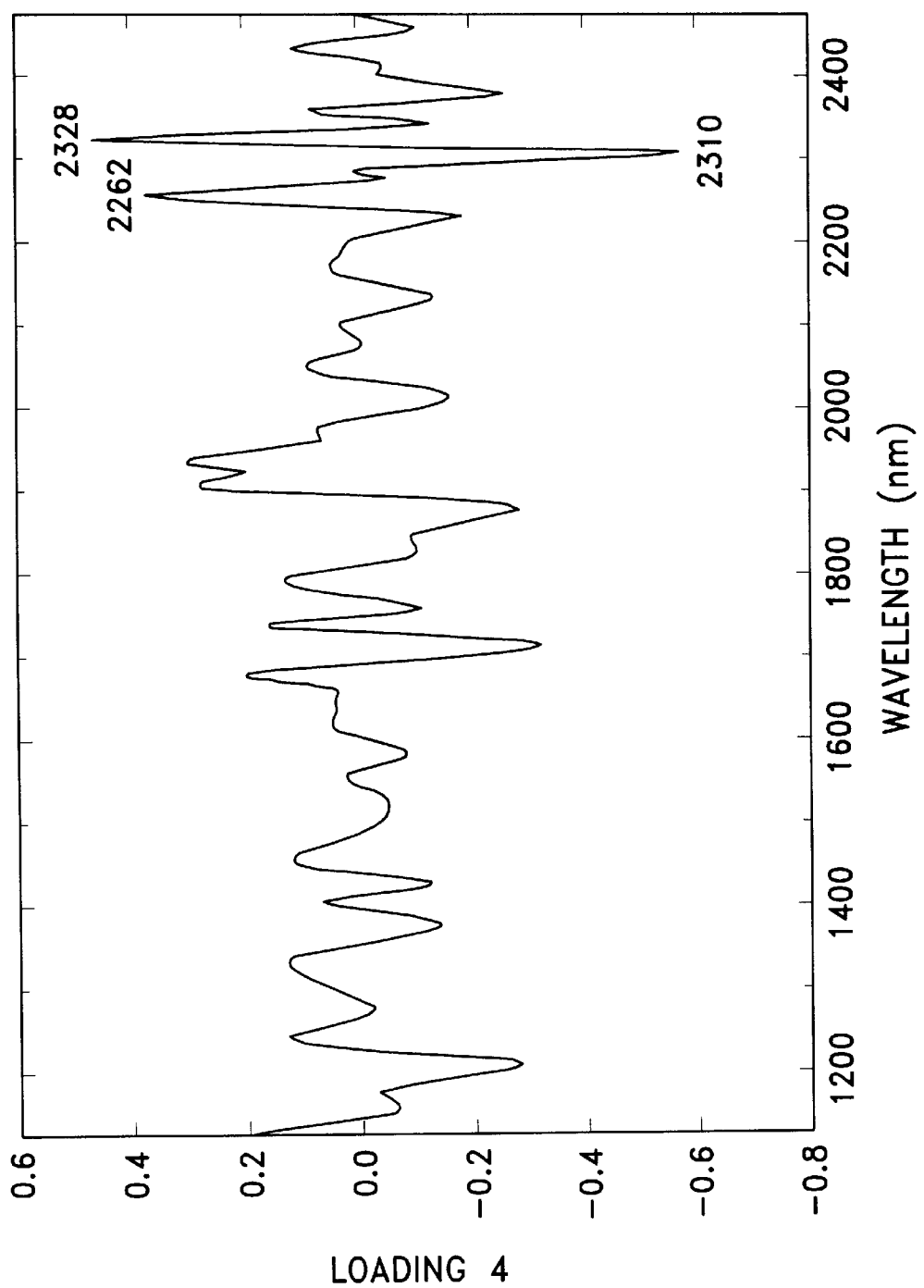

Loadings. Nine factors were employed in the calibration equation. Sample scores from PLS factors having the highest correlation with total dietary fiber were −0.52, 0.72, and 0.31 for factors 2, 3, and 4, respectively. The loadings for factors 2, 3, and 4, which express the spectral variation that corresponds to each factor, are shown in FIG. 4. Visual assessment of FIG. 4 suggested that certain shapes were common among the loadings. Samples scores from factor 3 had the highest correlation with dietary fiber and a loading (FIG. 4B) with large intensities related to O—H absorption in the water band at 1416 nm and the carbohydrate band at 2082 nm (Murray and Williams, 1987; Williams and Norris, 1987b). Loading 3 also had large intensities related to C—H bands at 1722 and 2304 nm. Factor 2 had the second highest correlation with dietary fiber and its loading (FIG. 4A) was dominated by O—H absorption in the water bands at 1413 and 1920 nm. Loading 2 also had significant intensity related to C—H absorption in the carbohydrate band at 2262 nm and the aliphatic C—H band at 2304 nm, and due to C+O absorption in the protein band at 2052 nm. Factor 4 had the third highest correlation with dietary fiber with intensities (FIG. 4C) due to C—H absorption in the carbohydrates bands at 2262 and 2328 nm and the aliphatic C—H band at 2310 nm. Overall, for the three loadings, absorbance was predominantly influenced by effects due to O—H and C—H groups in the water and carbohydrate bands.

Figure 5:
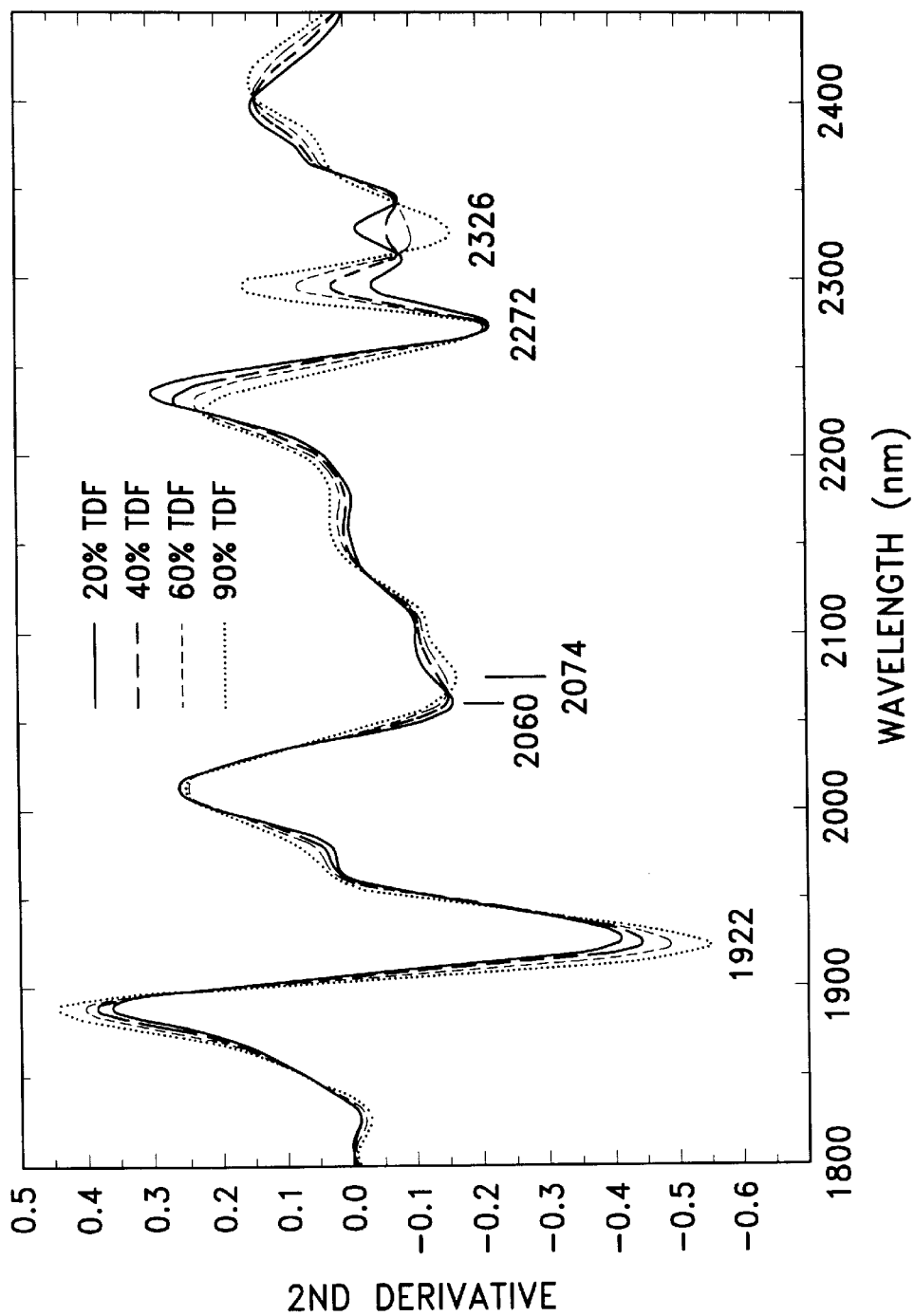
FIG. 5 shows second derivative NIRS spectra of cereal samples that have a range in total dietary fiber (TDF) content and contain the same matrix.

Variation in Dietary Fiber Concentration. The spectra of samples containing 20, 40, 60, and 90% total dietary fiber are shown in FIG. 5. Systematic changes in absorbance with varying total dietary fiber concentrations occurred in the C—H and O—H absorption regions. Systematic change in peak intensity with increased total dietary fiber concentration corresponded to the greatest influence in loadings 2, 3, and 4, that is, at wavelengths 1922 and 2326 nm, with a shift in the peak at 2060 nm.

EXAMPLE 2

Sugar Expanded Calibration Model

Unless indicated to the contrary, the same materials and methods as used in Example 1 were used in Example 2.

Instrumentation. Measurements were taken with a NIR-Systems 6500 Monochromator. A Nicolet 850 (Nicolet Instrument Corporation, Madison, Wis.) was employed as a mid-infrared Fourier transform (FT) spectrometer by configuring it with a globar source, a KBr beamsplitter, and a MCT/B liquid nitrogen cooled detector. Mid-infrared diffuse reflectance spectra were collected using the Collector™ accessory with macro cups. The sample compartment was continuously purged with air supplied by a Balston Model 75-62 (Balston Inc., Haverhill, Mass.) purge gas generator, that removed most of the $CO_2$ and water vapor to a dew point of $-73°$ C. Data collection and processing were performed using Omnic® software (Nicolet Instrument Corporation, Madison, Wis.).

Reagents. Heat stable α-amylase, A 3306; protease, P3910; amyloglucosidase, A 9913; acid washed celite, C 8656; total dietary fiber control kit, TDF-100A; MES, 2-(N-morpholino)ethanesulfonic acid, M-8250; TRIS, tris (hydroxymethyl)-aminomethane, T1503; D(+)glucose, G7528; D(-)fructose, F 0127; and sucrose, S 7903 were purchased from Sigma Chemical Co., St. Louis, Mo. Buffer (MES/TRIS, 0.05M) was prepared and adjusted to pH 8.2 at 24° C., although the buffer may be adjusted to pH 8.3 if the temperature is 20° C., and to pH 8.1 if the temperature is 28° C., with interpolation for intermediate temperatures.

Sample Preparation. Cereal and grain products were again prepared as in Example 1. Due to limited numbers of cereal products with high total dietary fiber content, commercial oat and wheat fibers (range in total dietary fiber 90–98%) are mixed with several processed cereals to provide 23 samples with high, medium and low dietary fiber content. Fifteen samples from Example 1 and 8 samples in the Example 1 validation set were prepared in this way (Tables 4 and 5). Commercial oat and wheat fibers were provided by Canadian Harvest USA L.P. (Cambridge, Minn.).

High sugar cereal products used for expansion of the calibration and validation data sets contained >20% sugar and included breakfast cereals, sugar-coated breakfast cereals, crackers, cookies, and muffin and cake mixes. Thirty nine high sugar samples were available for expansion of the calibration data set obtained in Example 1, and 15 for validation data set expansion. High sugar cereal samples, sucrose, glucose, and fructose were mixed with liquid nitrogen to facilitate grinding in a cyclone mill. Based on product label values, the range, mean, and standard deviation of sugar content of the high sugar cereal samples used in the sugar-expanded calibration data set were 21.8–53.3%, 35.4%, and 9.3% respectively, and in the sugar-expanded validation data set were 22.2–55.6%, 34.4%, and 9.2%, respectively.

Total Dietary Fiber Measured by the Reference Method. The values for total dietary fiber in cereal samples were determined by the AOAC enzymatic-gravimetric procedure as discussed previously. Purity and activity of enzymes was monitored as described previously. Before performing the AOAC procedure samples containing >20% sugar were desugared by extracting 4 times with 85% ethyl alcohol (10 ml/g sample), for 15 minutes with stirring and evaporated in a vacuum oven overnight at 30° C. The sugar extracted was calculated for each sample based on sample weight before and after extraction. Total dietary fiber values for desugared samples were adjusted for the percent sugar extracted and total dietary fiber values for all samples were calculated on a dry weight basis.

Spectroscopic Analysis. High sugar samples were scanned before desugaring. Spectra of sucrose and selected cereal samples were collected in the mid-infrared range (4000–400 $cm^{-1}$) using the Nicolet 850 FT spectrometer. Samples were diluted in powdered KBr (8% sample), to limit absorbance to approximately 0.8 absorbance units, and presented in open surface cylindrical metal cups (13 mm internal diameter, 2 mm depth). Data were averaged over 256 scans at 4 $cm^{-1}$ resolution after standing 10 minutes in a purged air environment. Sample spectra were Fourier transformed, ratioed against a KBr background and presented in the absorbance mode.

NIR Calibration on the Original Data Set. The original calibration was developed using a method similar to that previously described (Kays et al., 1996). Seventy-seven cereal samples were scanned with the NIRSystems 6500 monochromator and analyzed for dietary fiber using the reference method. The wavelength region was used for NIR analysis was 1100–2500 nm with 2 nm intervals. A commercial spectral analysis program (NIRS4, Infrasoft International Inc., Port Matilda, Pa.) was used to process the data and develop chemometric models. First, $log_{10}$ (1/R) spectra were transformed with standard normal variate and detrending procedures (Barnes et al., 1989), to remove multiplicative interferences of scatter, and then transformed with second-derivative processing (gap=20 nm, smoothing interval=10 nm). Data were subsequently centered using the CENTER program, available via NIRS4, which allows centering of samples based on constituent values as well as spectral characteristics, i.e., partial least squares-1 (PLS1; Lindberg et al., 1983). Prior to calibratio, $log_{10}$ (1/R) spectra were mean centered, transformed with standard normal variate and detrending procedures (Barnes et al., 1989) to remove multiplicative interferences of scatter, and then transformed with second-derivative processing (gap=8 nm, smoothing interval=8 nm). Calibration was performed using modified PLS regression available through NIRS4. The modification to PLS scaled the reference method data and reflectance data at each wavelength to have a standard deviation of 1.0 before each PLS regression term (Shenk and Westerhgaus, 1991a). The optimum number of PLS factors used for total dietary fiber prediction was determined by cross-validation (Martens and Naes, 1989). During cross-validation one-sixth of the calibration samples at a time was temporarily removed form the calibration set and used for prediction. Performance statistics were accumulated for each group of removed samples. The optimal number of factors for total dietary fiber was that which produced a minimum in overall error between modeled and reference values (SECV). The preprocessing transformations used were the optimum required to improve the SECV comparped to PLS analysis with untransformed data.

NIR Calibration on the Sugar-expanded Data Set. To expand the calibration obtained in Example 1, which contained products with low to medium amounts of sugar, to include products with high sugar and crystalline sugar content, 39 cereal products containing >20% sugar were purchased from grocery retailers. Using an algorithm called SELECT (NIRS4; Shenk and Westerhaus, 1991a, 1991b) high sugar samples from the group of 39 were selected for calibration expansion. The SELECT algorithm identifies samples within and outside the neighborhoods previously defined by the calibration of Example 1. Eleven PLS1 components were used by SELECT and, with the scores in eleven-dimensional space, the neighborhood H distance was calculated between all spectral pairs in the original model of Example 2 and each of the high sugar samples. A neighborhood H value of 0.6 was used to define the neighborhoods. Any high sugar sample whose neighborhood value was less than 0.6 H from any sample in the Example 2 model was eliminated, as neighbors of the central sample were considered to be spectrally similar and therefore not needed for calibration expansion. This process was performed with all the high sugar samples in the pool, until every sample was in either the calibration update or the eliminated set. Twenty five high sugar samples were chosen by the SELECT algorithm, out of the 39 available, for calibration expansion. Two of the 25 selected samples (Fudge Brownie Mix and Blueberry Muffin Mix) were discarded as spectral outliers (Mahalanobis distance >3; for discussion of methodology see Workman et al, *Applied Spectroscopy Reviews,* 31 (1&2), 73–124, 92 (1996), based on PLS analysis. Rescanned samples were also recognized as outliers. Twenty three high sugar samples were, thus, combined with the original 77 calibration samples of Example 2 to generate a 100 sample, sugar-expanded calibration data set. $Log_{10}(1/R)$ spectra were transformed and centered as described previously for the Example 1 data set and a sugar-expanded calibration model developed using modified PLS (Shenk and Westerhaus, 1991a) with the same preprocessing spectra transformations used for the Example 1 calibration.

The sugar-expanded model was tested using the Example 2 30 independent validation samples alone and the 30 Example 2 independent validation samples plus 15 independent high sugar samples. Model performance was reported as the SEP, $r^2$, slope and bias.

Total Dietary Fiber Measured by the Reference Method. For the high sugar samples the range in total dietary fiber for the calibration and validation data sets was from 0.6 to 14.9% and 1.0 to 10.6%, respectively. The distribution of samples for each grain type in the calibration and validation data sets are given in Tables 4 and 5. The range, mean, and standard deviation of total dietary fiber percent for each grain is also present. The standard error of the AOAC laboratory determinations was 0.73% for the samples in the Example 2 calibration and validation data sets and 0.88% for the high sugar samples.

TABLE 4

Cereal and Grain Products in the Calibration Data Set. The Range, Mean, and Standard Deviation (SD) of Total Dietary Fiber (TDF) Percent

| Samples | Product Type | Number of Products | Range in TDF % | Mean TDF % | SD TDF % |
|---|---|---|---|---|---|
| original | wheat | 25 | 2.9–41.1 | 13.3 | 9.7 |
| | oats | 6 | 8.1–19.0 | 12.6 | 4.32 |
| | corn | 4 | 1.2–13.6 | 6.5 | 5.4 |
| | rice | 8 | 0.7–4.3 | 2.2 | 1.5 |
| | rye | 1 | 38.4 | | |
| | barley | 2 | 12.4–19.4 | 15.86 | |
| | millet | 3 | 2.7–3.6 | 3.1 | 0.5 |
| | multiple grain | 13 | 6.5–41.0 | 16.9 | 13.4 |
| | commercial fiber & cereal product mixes | 15 | 6.4–52.1 | 31.2 | 14.7 |
| high sugar | wheat | 5 | 3.6–14.9 | 8.8 | 4.2 |
| | oats | 3 | 6.7–10.6 | 8.5 | 2.0 |
| | corn | 3 | 0.6–2.1 | 1.4 | 0.8 |
| | rice | 1 | 1.5 | | |
| | multiple grain | 11 | 2.2–11.9 | 7.3 | 2.9 |

TABLE 5

Cereal and Grain Products in the Validation Data Set. The Range, Mean and Standard Deviation (SD) of Total Dietary Fiber (TDF) Percent

| Samples | Product Type | Number of Products | Range in TDF % | Mean TDF % | SD TDF % |
|---|---|---|---|---|---|
| original | wheat | 7 | 3.6–43.7 | 13.0 | 14.1 |
| | oats | 1 | 15.4 | | |
| | corn | 2 | 1.8–4.9 | 3.4 | |
| | rice | 3 | 1.2–2.2 | 1.5 | 0.6 |
| | rye | 2 | 13.3–1801 | 15.7 | |
| | multiple grain | 10 | 2.0–39.3 | 16.8 | 13.1 |
| | commercial fiber & cereal product mixes | 5 | 12.5–42.8 | 29.4 | 12.7 |
| high sugar | wheat | 1 | 5.8 | | |
| | oats | 1 | 6.9 | | |
| | corn | 1 | 2.4 | | |
| | rice | 1 | 1.4 | | |
| | multiple grain | 9 | 1.0–10.6 | 5.3 | 3.1 |

Figure 6:
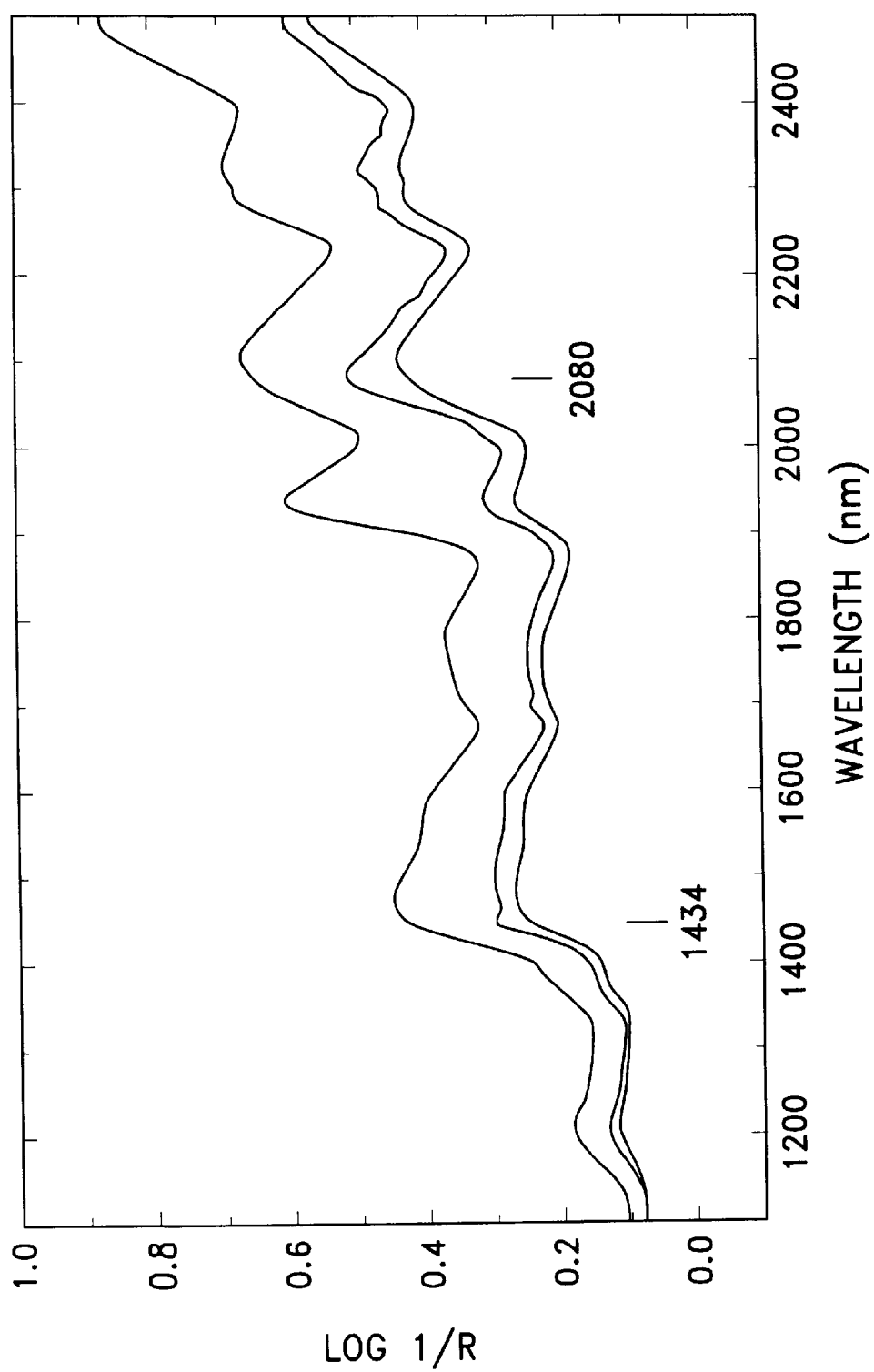
FIG. 6 shows near-infrared spectra of Corn Flakes® (7% sugar, upper plot), Frosted Flakes® (43% sugar, middle plot), and Golden Crisp® cereal (56% sugar, lower plot)
Figure 7A:
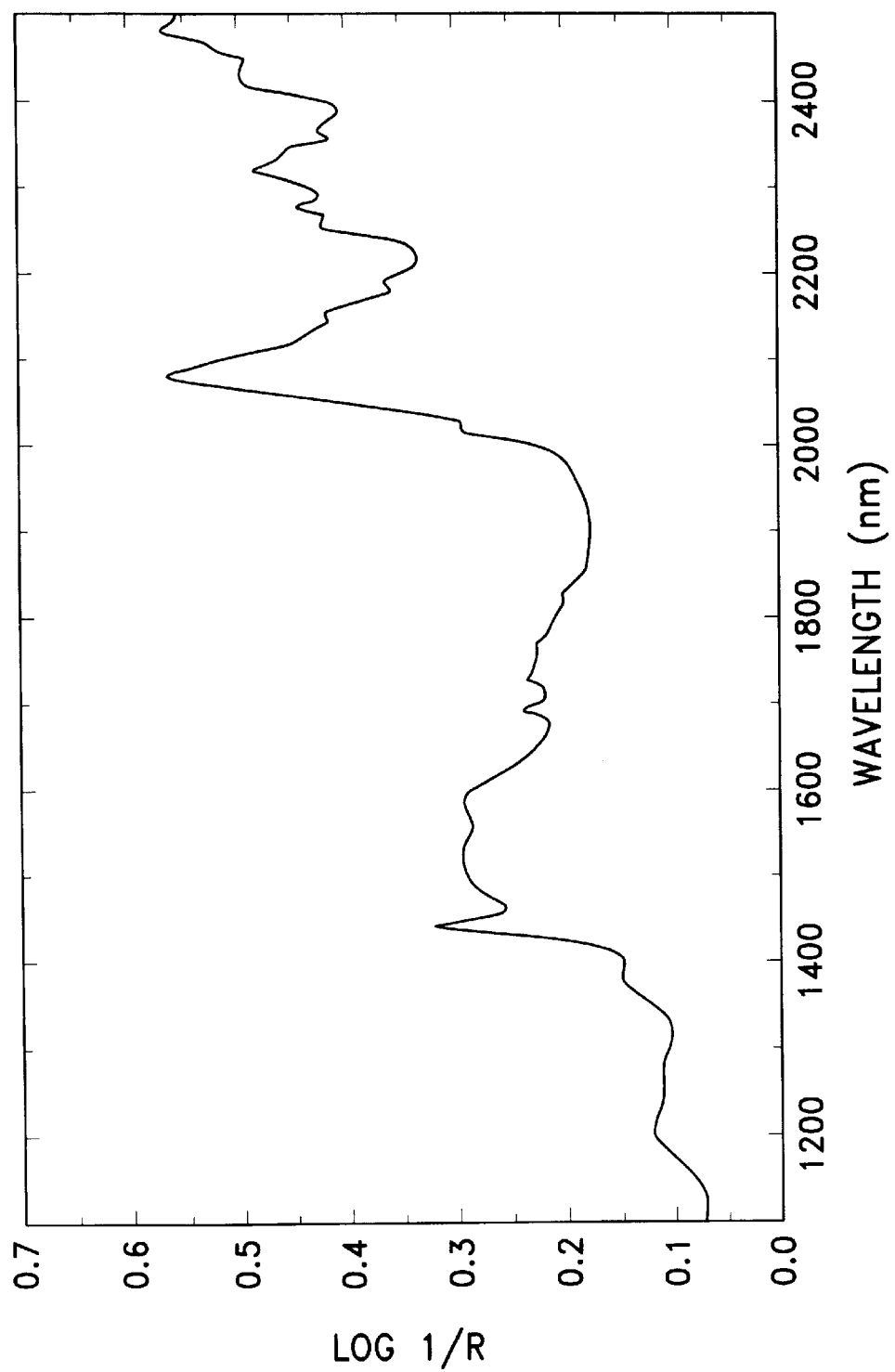
FIG. 7 shows near-infrared spectra of sucrose (A), glucose (B), and fructose (C)
Figure 7B:
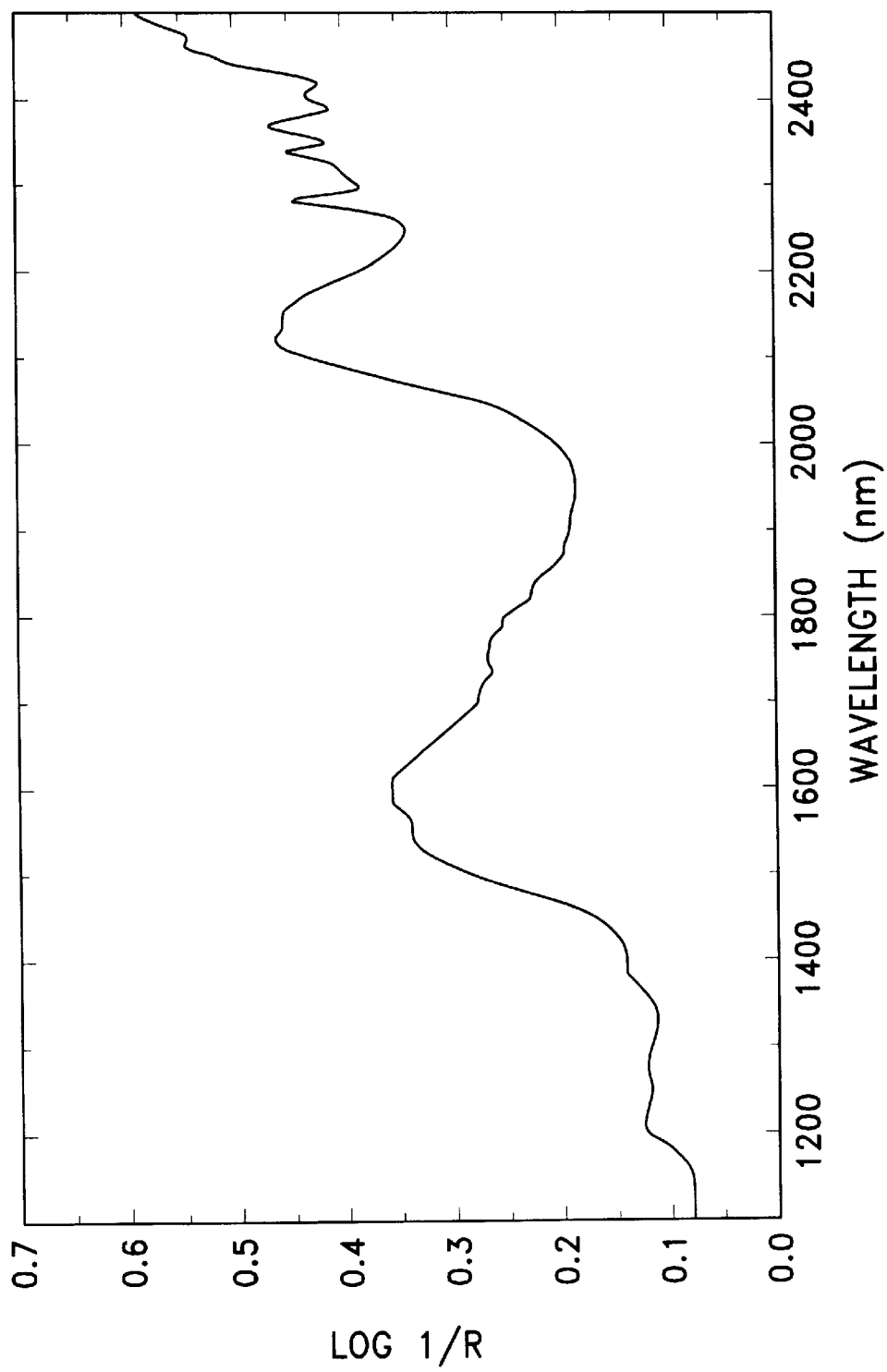
Figure 7C:
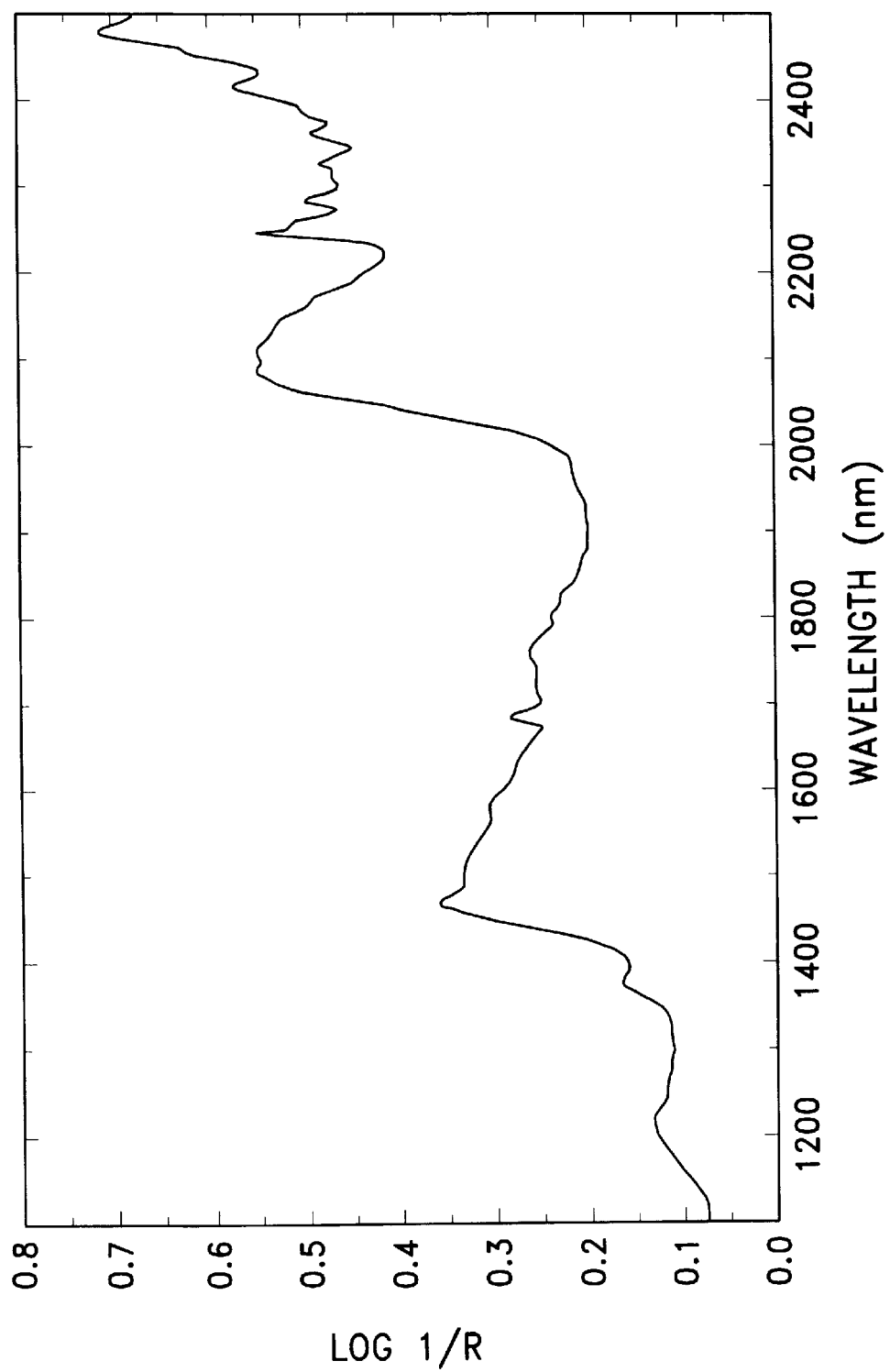
Figure 8:
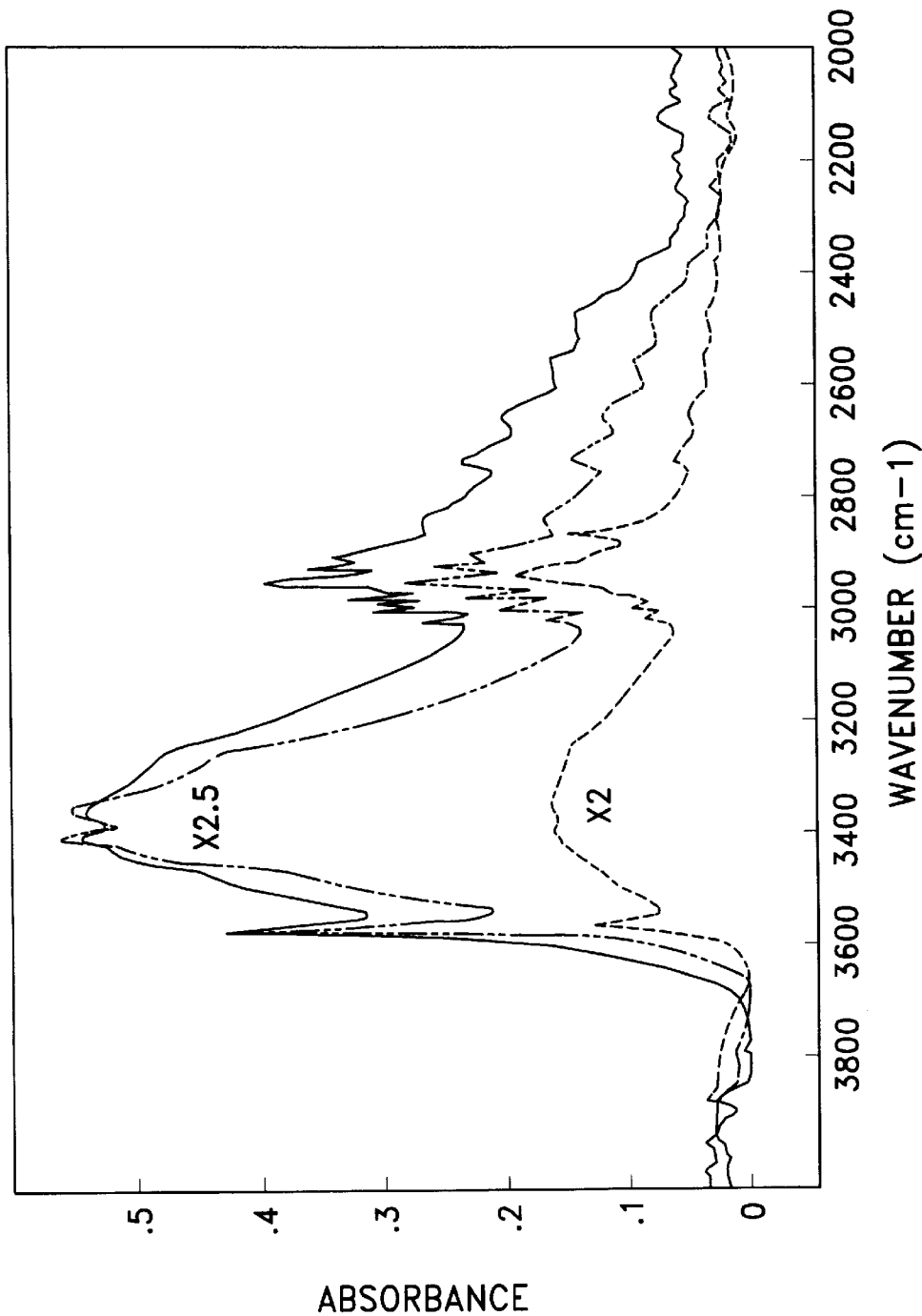
FIG. 8 shows mid-IR spectrum of sucrose (solid line), and mid-infrared difference spectra of Frosted Flakes® minus Corn Flakes® (ratio 1:1, dashed line) and Honey Crunch Corn Flakes® minus Corn Flakes® (ratio 1:1, broken line). The difference spectra are multiplied by 2.5 and 2, respectively.

Spectral Characteristics of Samples. Examples of NIR spectra of cereal samples with varying amounts of sugar are given in FIG. 6. The upper plot is the spectrum of Corn Flakes® cereal which contains approximately 7% sugar, present as sucrose and high fructose corn syrup (predominantly fructose). The middle plot is the spectrum of Frosted Flakes® cereal with 43% sugar, present as sucrose and corn syrup (predominantly glucose). The lower plot is the spectrum of Golden Crisp® cereal with 56% sugar present as sucrose, corn syrup, and honey (a mixture of sucrose, glucose and fructose). The spectrum of Frosted Flakes® is typical of cereal products containing large amounts of crystalline sugar with a sharp peak at 1434 nm and a sharp peak at 2080 mn. Seventeen of the 23 high sugar samples selected for calibration and 8 of the 15 high sugar validation samples showed evidence of crystalline sugar in the near-infrared spectra. Although Golden Crisp® cereal contains a large amount of sugar it does not appear to contain crystalline sugar (FIG. 6). Sucrose, D(+) glucose. and D(−) fructose are the most common sugars found in cereal products, and have unique spectra as demonstrated in FIG. 7, panels A, B and C, respectively. Sucrose has particularly sharp absorbances at 1434 nm and 2070 nm. The monomeric sugars, glucose and fructose, do not exhibit the same characteristics as sucrose at 1434 and 2070 nm. However, they mimic sucrose in other areas of the spectrum. The fundamental O—H and C—H bands that are responsible for absorbances at 1434 and 2070 nm in the near-infrared spectrum for sucrose occur in the 4000–2000 cm$^{-1}$ portion of the mid-infrared region and are shown in FIG. 8 (solid line). FIG. 8 also shows the difference spectrum for Frosted Flakes minus Corn Flakes® (FIG. 8, dashed line) and Honey Crunch Corn Flakes® minus Corn Flakes® (FIG. 8, broken line) in the same portion of the mid-infrared spectrum. The difference in the spectrum of the former reflects a difference in the sucrose amount, which is greater in Frosted Flakes®. In the latter, a difference can be detected in the amount of sucrose and in a long chain-hydrocarbon (2930 and 2854 cm$^{-1}$) which may be lipid. The additivity of the spectra in FIG. 8 would indicate that the sugar frosting is not part of the matrix, but merely mixed with it. The requirement for a single new factor to account for added sugar (see FIGS. 9 and 10 and associated discussion) also suggests that sugar is present in the matrix of many samples but not part of it.

Original NIR Calibration Model for Total Dietary Fiber. As reported previously (Kays et al., 1996) a NIR calibration was obtained, using PLS, for determination of the concentration of total dietary fiber in cereal products. This model was designated the "original" calibration in the prsent study and contained products with <20% sugar and <10% fat. For the original calibration the overall error between moeled and referenced values (SECV), using six cross-validation groups, was 1.64%, with $R^2$ of 0.99 (Table 3). Independent validation samples were predicted using the original calibration model. When NIR-predicted values for dietary fiber were compare statistically with AOAC-determined values, the SEP was 1.39% and $r^2$ 0.99 (Table 3). The SEP was lower than the SECV, possibly because the range in total dietary fiber values for the validation data set falls within the range of values for the calibration data set. Linear regression of AOAC determined dietary fiber against NIR-predicted dietary fiber for the calibration data (Y=0.07+1.00X) and the validation data (Y=−0.18+1.02X) gave intercepts and slopes not significantly different from 0.0 and 1.0, respectively (p>0.05).

Sugar-expanded NIR Calibration Model for Total Dietary Fiber. The sugar-expanded calibration data set contained products that spanned the range of high (>20%), medium, and low sugar content. Thus, a NIR calibration was obtained, using modified PLS, for determination of total dietary fiber in cereal products containing a wide range of sugar and crystalline sugar. Using 6 cross validation groups, the SECV for the sugar-expanded calibration was 1.88% and $R^2$ was 0.98 (Table 6). The intercept and slope of the linear regression line (AOAC determined dietary fiber versus NIR predicted dietary fiber, Y=−0.23+1.00X), were not significantly different from 0.0 and 1.0, respectively (p>0.05). Initially 15 independent high sugar validation samples were purchased. Fifteen high sugar validation samples were combined with the Example 2 30 validation samples and predicted with the sugar-expanded model. One validation sample (Low Fat Apple Cinnamon Muffin Mix) was discarded as a spectral outlier (Mahalanobis distance >3.0). The SEP was 1.58%, $r^2$ 0.98, and bias −0.30. One sample (Cocoa Pebbles) was identified as a residual (t statistic) outlier (the sample was re-scanned and re-analyzed for dietary fiber using the reference method and still recognized as an outlier). When this sample was removed the SEP was 1.40%, $r^2$ 0.99, and bias −0.40 (Table 6). As with the Example 1 calibration the SEP was lower than the SECV. The intercept and slope of the linear regression line (AOAC determined versus NIR predicted dietary fiber for the sugar-expanded validation data set, Y=−0.64+1.02X) were not significantly different from 0.0 and 1.0, respectively (p>0.05). When the model developed in Example 1 was used for prediction of total dietary fiber in the Example 2 30 validation samples plus the 13 high sugar validation samples, the SEP, $r^2$, bias, and slope were 4.22%, 0.91, 1.21, and 0.87, respectively. The large SEP and bias are primarily due to markedly under-predicted values for high sugar products that exhibit spectral evidence of crystalline sugar. A comparison of AOAC determined values versus NIR predicted values, using the two models developed in Examples 1 and 2, for the individual high sugar validation samples is presented in Table 7. The sugar-expanded model was used to predict the original validation samples (N=30) alone with a resulting SEP, $r^2$, bias, and slope of 1.42%, 0.99, −0.66 and 1.04, respectively.

TABLE 6

Calibration and Validation Statistics for Dietary Fiber Prediction by the Example 2 and Sugar Expanded NIR Models[a]

| Model | Method | calibration | | | | | validation | | | | | |
|---|---|---|---|---|---|---|---|---|---|---|---|---|
| | | n | Mean | SD | SECV | $R^2$ | n | Mean | SD | SEP | $r^2$ | Bias | Slope |
| original | AOAC | 77 | 15.83 | 13.70 | | | 30 | 15.50 | 13.53 | | | | |
| | NIRS | 77 | 15.83 | 13.66 | 1.64 | 0.99 | 30 | 15.34 | 13.17 | 1.39 | 0.99 | 0.16 | 1.02 |
| expanded | AOAC | 100 | 13.74 | 12.73 | | | 43 | 12.31 | 12.36 | | | | |
| | NIRS | 100 | 13.93 | 12.54 | 1.88 | 0.98 | 43 | 12.61 | 12.23 | 1.40 | .099 | −0.40 | 1.01 |

[a]Mean, standard deviation (SD), standard error of cross validation (SECV), and multiple coefficient of determination ($R^2$) for calibration. Mean, standard deviation, standard error of performance (SEP), and coefficient of determination ($r^2$) for validation.

[b]Validation samples (n = 30) used to test the Example 2 model contained <20% sugar. Validation samples (n = 43) used to test the sugar expanded model consisted of 30 validation samples containing <20% sugar plus 13 samples with >20% sugar.

TABLE 7

NIR Prediction of Dietary Fiber in High Sugar Cereal Products

| Product | AOAC TDF % | NIR Predicted TDF %[a] Original Model | NIR Predicted TDF %[a] Sugar Expanded Model |
|---|---|---|---|
| Fruit and Fiber ® | 10.58 | 15.93 | 12.12 |
| Healthy Choice ® | 9.36 | 11.31 | 10.01 |
| Golden Crisp ® | 3.59 | 9.37[b] | 6.15 |
| Honey Graham ® | 4.80 | 4.52 | 4.36 |
| Oatmeal Crunch ® | 4.52 | 4.18 | 4.91 |
| Blueberry Morning ® | 3.38 | 3.89 | 3.71 |
| Golden Grahams ® | 3.54 | 3.33 | 4.43 |
| Honey Nut Cheerios ®[c] | 7.29 | 3.33 | 4.43 |
| Nut and Honey Crunch ®[c] | 2.45 | −3.97 | 0.93 |
| Apple Cinnamon Toasted Oats ®[c] | 6.87 | −4.00 | 5.79 |
| Honey Crunch Corn Flakes ®[c] | 1.84 | −7.09 | 0.93 |
| Oat Bran Muffin Mix ®[c] | 4.65 | −10.62 | 2.44 |
| Double Dip Crunch ®[c] | 1.01 | −9.97 | −0.77 |

[a]Total dietary fiber.
[b]Global outlier (Mahalanobis distance > 3).
[c]Spectral evidence of crystalline sugar.

PLS Loadings. In the Example 2 calibration 9 factors were employed in the model and explained 99.1% of the spectral variation. Sample scores having the highest correlation (calculated by Pearson Correlation Coefficient) with dietary fiber were for factors 1, 2 and 3 with correlation coefficients of 0.78, 0.56 and 0.19, respectively.

Figure 9A:
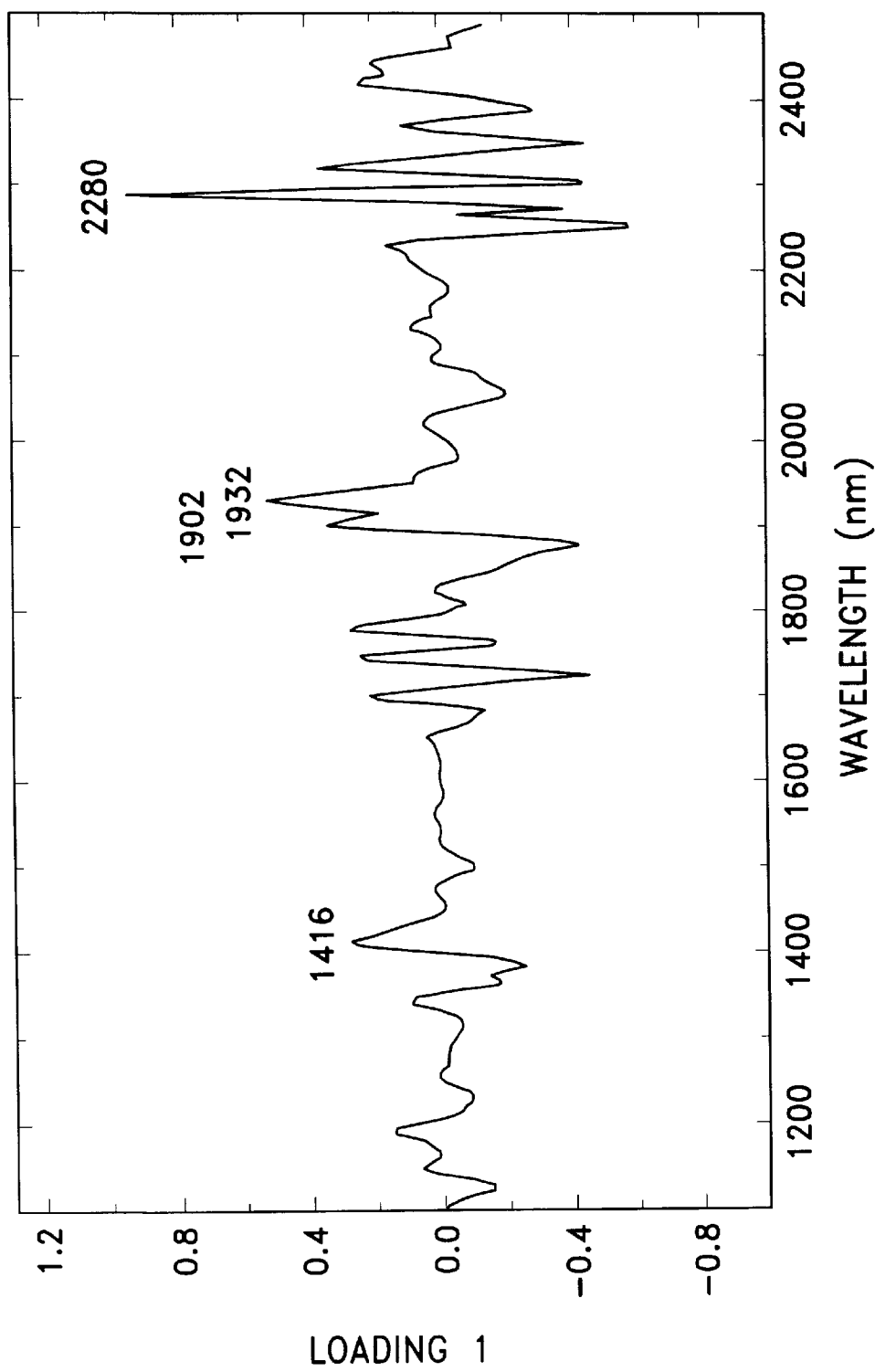
FIG. 9 shows PLS loading spectra for total dietary fiber in cereal products in the Example 2 model. Panels A, B and C represent loadings for factors 1, 2 and 3 respectively.
Figure 9B:
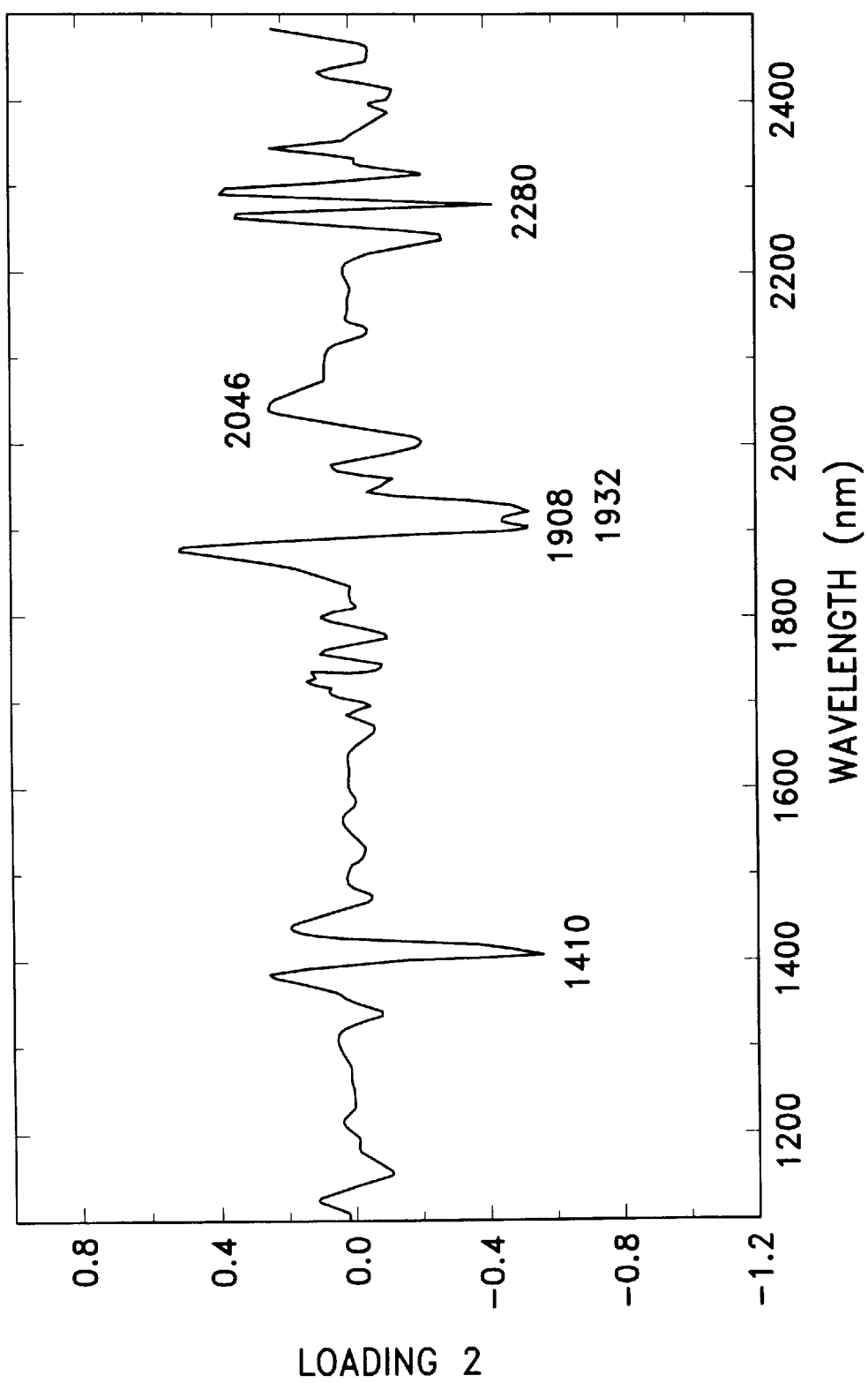
Figure 9C:
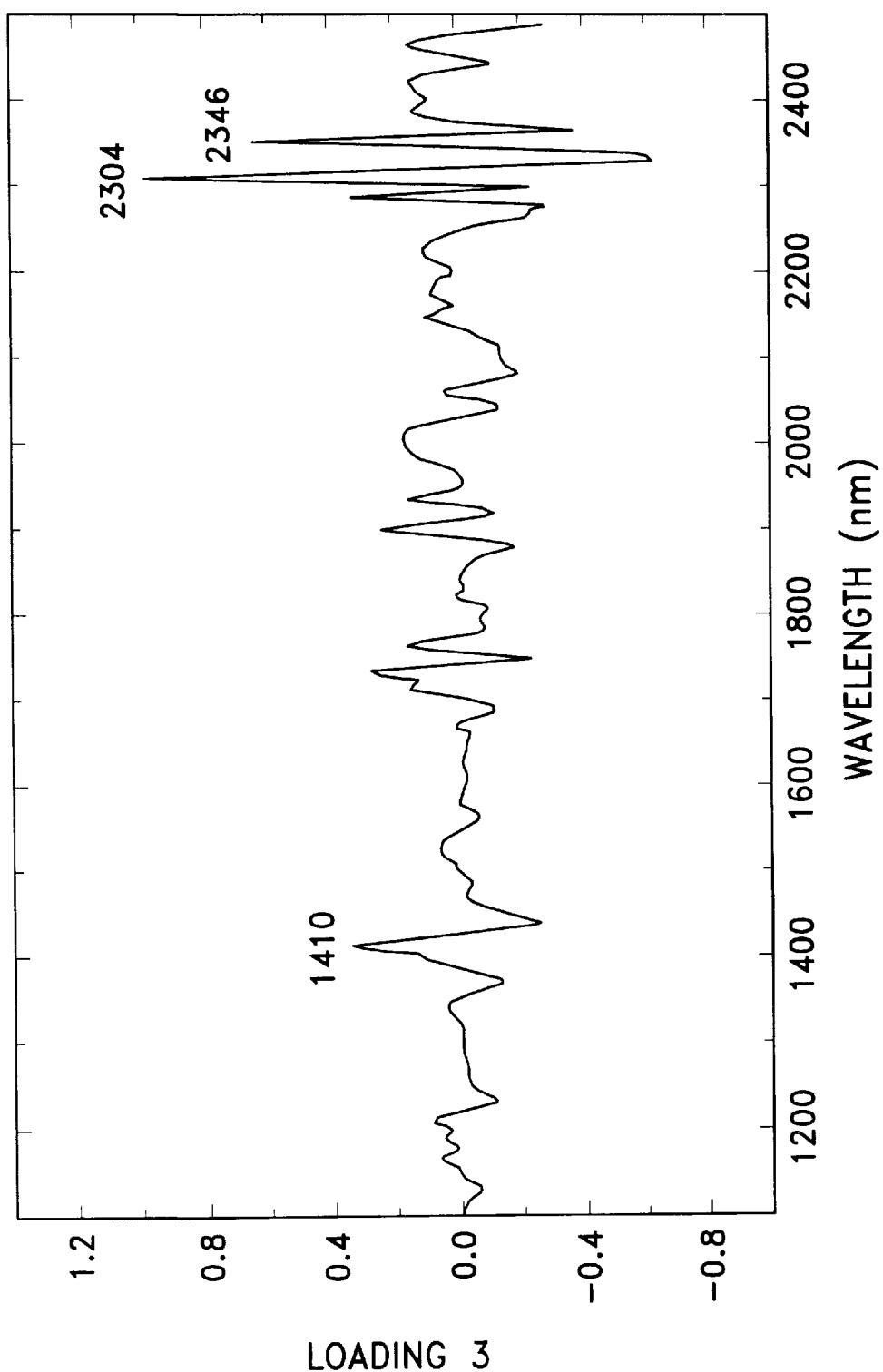

PLS loadings, which are the regression coefficients of each wavelength to dietary fiber for each factor, can indicate wavelengths of high variation in a calibration set which may show association with wavelengths of chemical origin known a priori. The two calibration sets appear to have loadings of high relative positive or negative value at wavelengths that are known for carbohydrates, water, or lipids. Association of these known vibrations with the appearance of key values in loadings, along with the correlation of individual loadings independently to fiber or sugar content, lend an estimation of what chemical component is the primary contributor for each loading. Loading plots for factors 1, 2 and 3 of the Example 1 model are presented in FIG. 9. Factor one had the highest correlation with dietary fiber and its loading has peaks correlated to O—H absorption in water bands at 1416 and 1902/1932 nm and C—H absorption in the carbohydrate band at 2280 nm (FIG. 9A). The loading for factor two has regression coefficient related to absorption by O—H in the water bands at 1410 and 1908/1932 nm, C—H groups of carbohydrate at 2280 nm, and amide in the protein band at 2046 nm (FIG. 9B). The loading for the third factor exhibited effects associated with C—H stretch groups in lipid at 2304 and 2346 nm (FIG. 9C). The model appears to be predominantly influenced by carbohydrate and water absorbance with smaller influences due to protein and lipid.

Figure 10A:
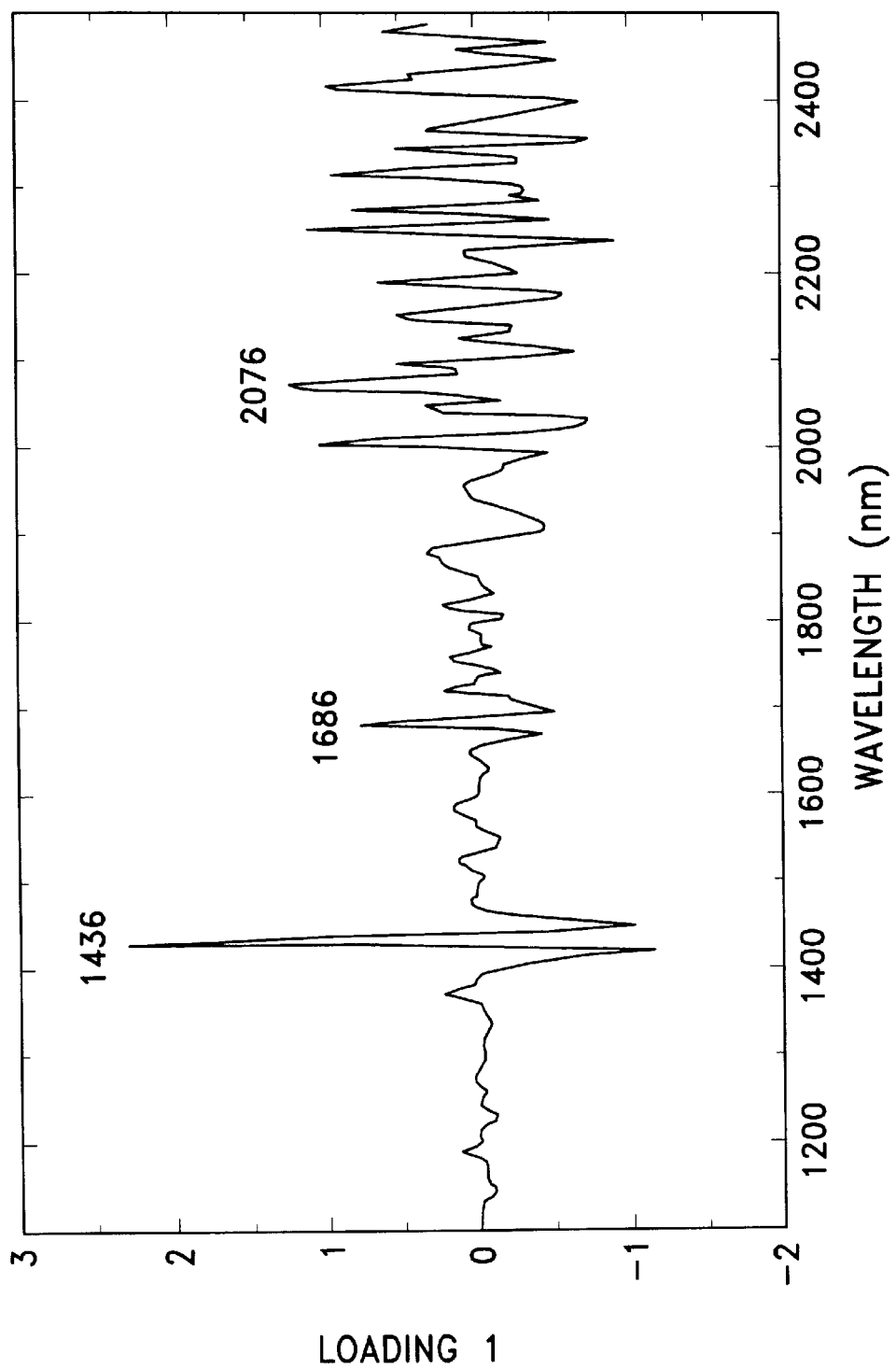
FIG. 10 shows PLS loading spectra for total dietary fiber in cereal products in the sugar expanded model. Panels A, B and C represent loadings for factors 1, 2 and 3 respectively.
Figure 10B:
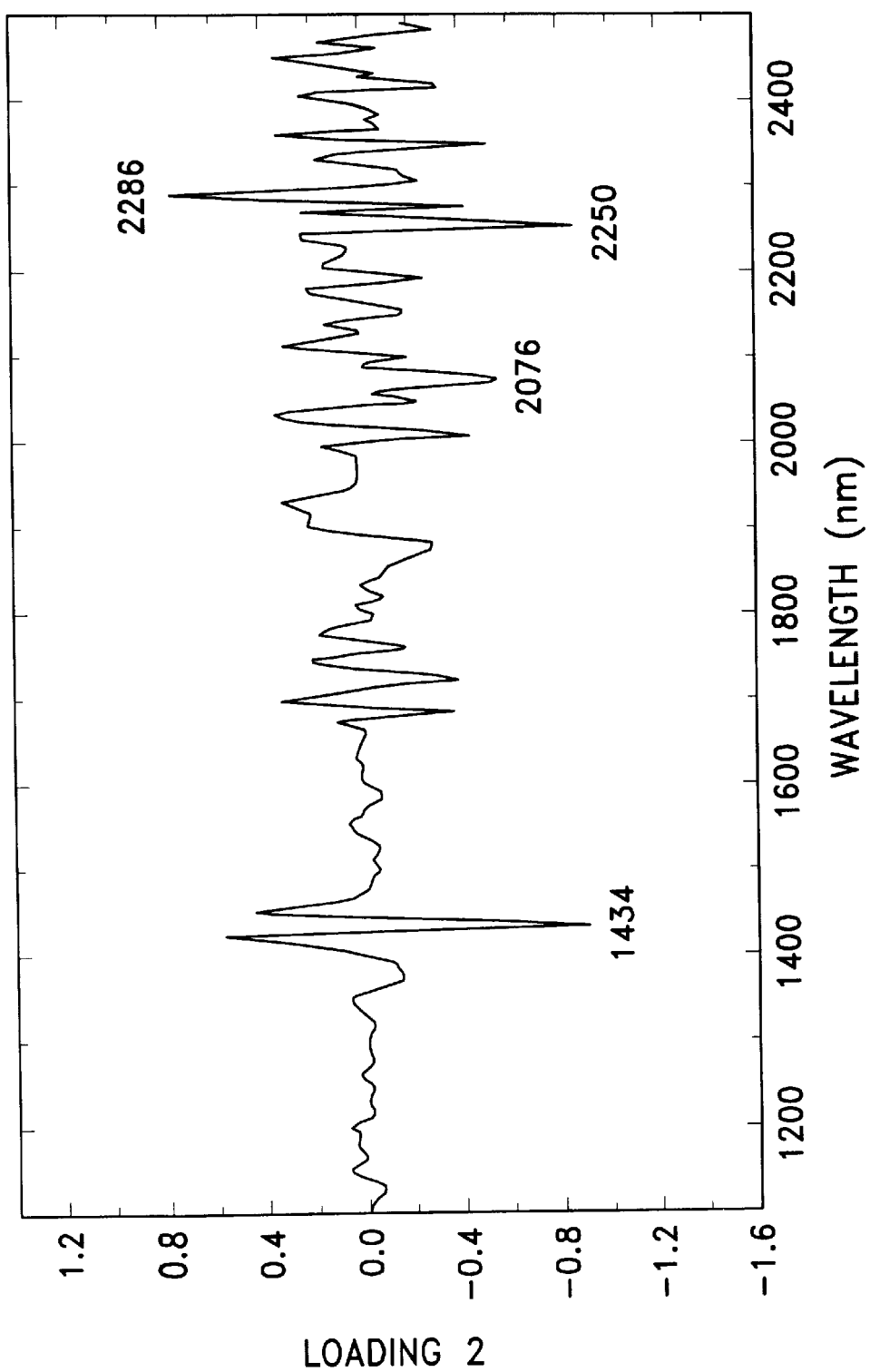
Figure 10C:
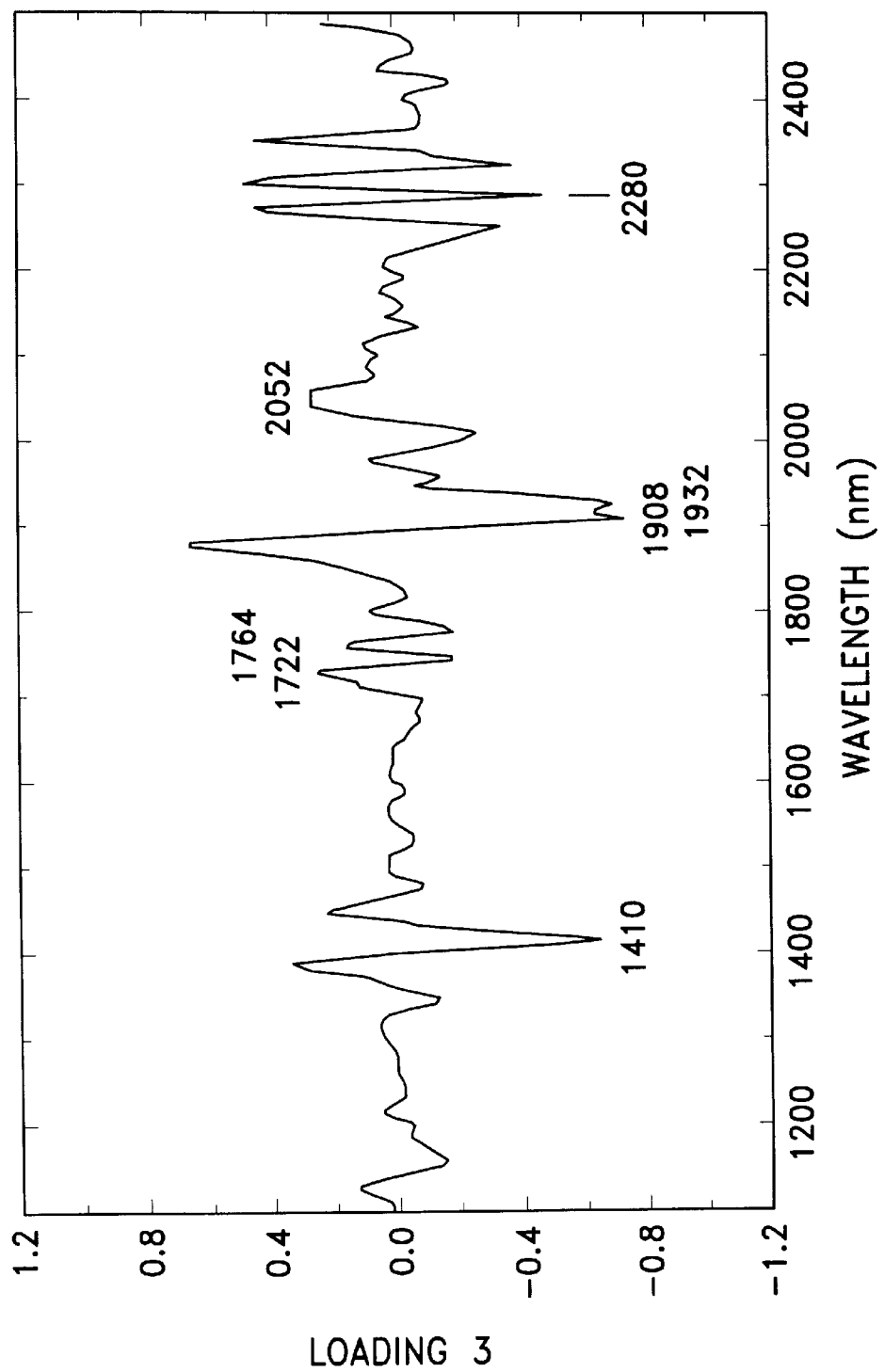

Eight factors were employed in the sugar-expanded model and explained 98.5% of the spectral variation. Sample scores having the highest correlation with dietary fiber were for factors 1, 2 and 3 with correlation coefficients of 0.48, 0.76 and 0.37, respectively. The loading for factor 2 showed strong correlation to absorbance at 1434 nm, typical of O—H groups in crystalline sugar, and to the 2200 to 2300 nm carbohydrate absorbing region of the NIR spectrum (FIG. 10B). The loading for factor one also has a sharp peak at 1436 nm (FIG. 10A) and peaks at 2076 nm and 2200 to 2300 nm correlated to carbohydrate (FIG. 10A). The third factor of the sugar-expanded model had a loading plot with peaks at 1410 and 1908 nm which are commonly associated with water and at 2280 associated with carbohydrate (FIG. 10C). Overall the sugar expanded model appears to be predominantly influenced by carbohydrate with sharp peaks at 1434 nm and peaks at 2076 and 2200 to 2300 nm. Lesser influences due to water, lipid, and protein are indicated by the third loading.

Figure 11A:
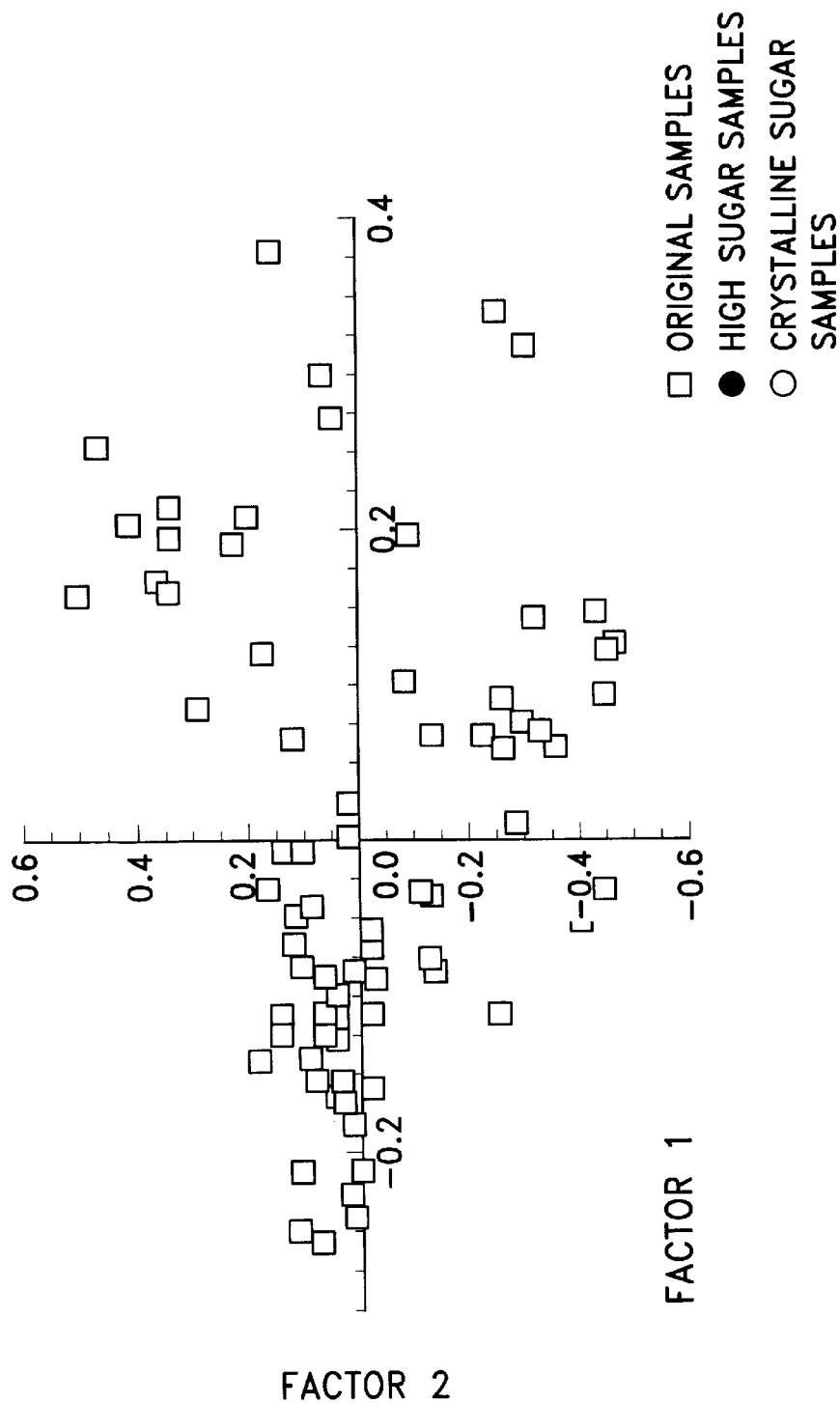
FIG. 11 shows plots for the PLS scores for factor 1 versus factor 2 for the Example 2 model (A) and the sugar expanded model (B)
Figure 11B:
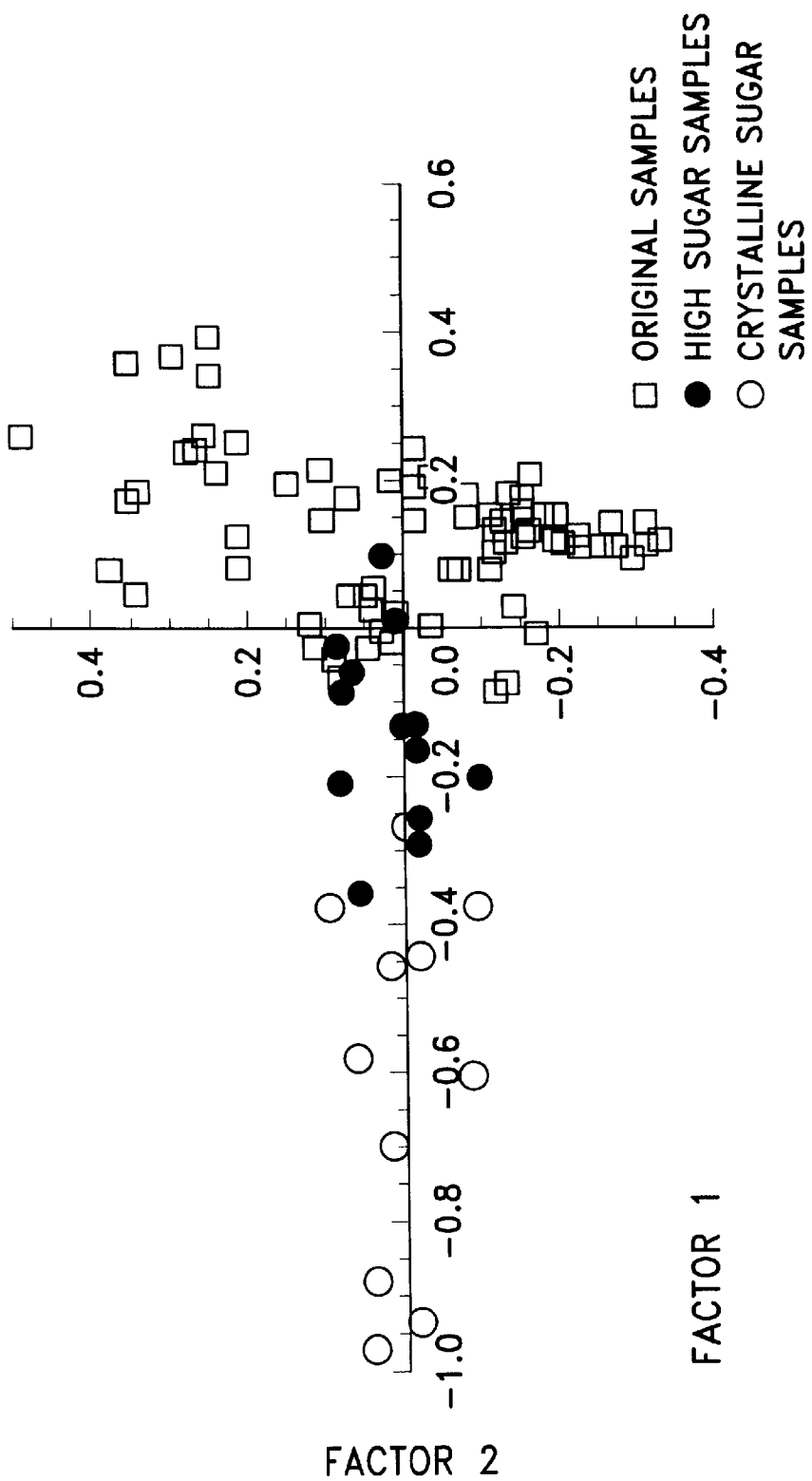

PLS Scores. Plots of the factor 1 versus factor 2 scores for total dietary fiber are represented in FIG. 11. In the Example 2 model, the contribution of dietary fiber (Pearson Correlation Coefficient=0.78) is appreciable resulting in the visualization of samples of low to high fiber primarily along the factor 1 axis (FIG. 11A). For the sugar-expanded model (FIG. 11B), the predominant contribution to factor 1 appears to be sugar content, based on product label values (Pearson Correlation Coefficient=−0.84), whereas, the predominant contribution to factor 2 appears to be dietary fiber (Pearson correlation Coefficient=0.76). Crystalline sugar samples, in general, have the highest sugar content and separation of these samples along the factor 1 axis is illustrated in FIG. 11B.

Accordingly, in Example 2, the calibration for prediction of total dietary fiber in cereal products has been expanded to include cereal products with high sugar and crystalline sugar content. The accuracy of total dietary fiber prediction, overall, for high sugar samples was markedly improved by the sugar-expanded model compared to the Example 1 model. Products containing crystalline sucrose, for example, were greatly under-predicted by the Example 1 equation; however, using the sugar-expanded model, predicted values for total dietary fiber were acceptably close to the AOAC determined values. The SECV is slightly higher for the sugar-expanded model, compared to the Example 1 and Example 2 models. Thus, for samples containing less than 20% sugar, either model could be used. Overall, it is an advantage to be able to predict a wide range of products, including high sugar samples, with one calibration.

Sucrose, glucose and fructose are the sugars in cereal products. Many cereal products contain: corn syrup, which is predominantly glucose; high fructose corn syrup, which is predominantly fructose with glucose making up the difference; and honey, which contains a mixture of sucrose, fructose, and glucose. Each of the 3 sugars has unique NIR spectral characteristics which are apparent in cereal products as sharp absorbance bands in specific areas of the product's NIR spectra. Correlations to these bands are observed in loadings 1 and 2 of the sugar-expanded model. Spectral properties of specific cereal products may depend on the concentration of free sugars or honey added to the product, in particular the ratios of crystalline sucrose to sucrose and the presence of glucose or fructose. Some, though not all, high sugar samples were predicted poorly by the Example 2 model (one was a global outlier), however the Example 2 sugar-expanded model has corrected this deficiency.

In the present Example three of the 59 high sugar samples were identified as spectral outliers (two from the calibration and one from the validation data sets). All 3 samples displayed spectral evidence of crystalline sugar and all 3 were mixes (one brownie mix and 2 muffin mixes). Discarding the 3 samples eliminated the only muffin and brownie mixes remaining in the calibration data set. A substantially greater number of samples of this type would expand the calibration to include these products.

The need for extraction of sugar before performing the AOAC procedure increases the length of the assay from 2 days to 3 days and can also potentially decrease the accuracy of the assay. In contrast, for near-infrared analysis, prior extraction of sugar is not required and sample preparation merely consists of grinding. The calibration obtained to associate AOAC total dietary fiber values with NIR spectra can be used for analysis of new prediction samples merely by obtaining NIR spectra of the products. Thus, use of the NIR calibration reduces the time required for total dietary fiber determination from 2 or 3 days to several minutes.

Examination of the loadings for the three factors most highly correlated with total dietary fiber suggests that the sugar-expanded model is predominantly influenced by O—H and C—H groups from the carbohydrate fractions with smaller influences from water, lipid, and protein. This is in contrast to the Example 1 and Example 2 models in which major influences appear to be from carbohydrate and water with minor influences from protein and lipid. It is important to note that the second loading of the Example 2 model is almost identical to loading 3 of the Example 2 sugar-expanded model and that loading 1 of the Example 2 model is very similar in many respects to the loading 2 of the Example 2 sugar-expanded model. However, a new loading was introduced in the expanded model, loading number 1, which appears to account for, or counteract, the effect of the three sugars present. The sharp peaks at 1434/1436 nm in loading 1 correlate with absorbance bands of O—H groups found in crystalline sugar. The importance of factor 1 is further demonstrated in the score plots. By interchanging the axes in FIG. 11B it is observed that the pattern of the low sugar samples is similar to the pattern in FIG. 11A. The position of the high sugar samples in FIG. 11B suggest that the effect of factor 1 in the new model is to account for the presence of sugar.

EXAMPLE 3

Fat and Fat and Sugar Expanded Calibration Model

Unless indicated to the contrary, the same materials and methods as used in Example 1 were used in Example 3.

Instrumentation, Reagents, and Enzyme Purity and Activity. Instrumentation, reagents, and testing of enzyme purity and activity were as described above.

Samples and Sample Preparation. Cereal and grain products, including breakfast cereals, crackers, brans, flours, and cake and muffin mixes were as described above. Products used for the fat-expanded calibration and validation data sets contained >10% fat and included breakfast cereals, granolas, crackers, graham crackers and cereal based snacks. Twenty high fat cereal products were available for expansion of the calibration data set and 10 for expansion of the validation data set. High fat samples were ground in a Coffee Mill (Model KSM-2, Braun, Inc., Lynnfield, Mass.). Based on the nutrition label value of products, the range, mean and standard deviation of fat content of the high fat samples used in the calibration were 10.7–30.0%, 16.3% and 5.8%, respectively, and in the validation sample set were 11.1–23.3#, 17.0%, and 4.8%, respectively.

Reference Laboratory Method for Total Dietary Fiber. Total dietary fiber in all samples was measured in the laboratory by the AOAC approved method as described above. Before performing the AOAC procedure samples containing >10% fat were defatted by extracting 3 times with petroleum ether (25 ml/g sample), for 15 minutes each with stirring, and evaporated overnight at room temperature in a fume hood. Total dietary fiber values for defatted or desugared samples were adjusted for the % fat or sugar extracted. Total dietary fiber values for all samples were calculated on a dry weight basis. Dry matter/moisture content of milled cereal products was determined by the AOAC air oven method 945.14.

Spectroscopic Analysis. All dry milled cereal samples were scanned with the NIRSystems 6500 monochromator (NIRSysstems, Silver Springs, Md.) as described above. High fat and high sugar samples were scanned before defatting and desugaring. The duplicate scans of each sample were examined visually for consistency and averaged.

NIR Calibration on the Fat Expanded Calibration Data Set. A commercial analysis program (NIRS 3 Version 4.01, Infrasoft International Inc., Port Matilda, Pa.) was used to process data, select representative high fat samples and build chemometric models. As in Example 2, SELECT was used to select high fat samples for calibration expansion. Eleven components were used for the selection. Eighteen high fat samples were chosen by the SELECT algorithm, out of the 20 available, for calibration expansion. One of the 18 selected samples (Salted Sesame Sticks) was discarded as a spectral outlier (Mahalanobis distance >3), based on PLS analysis. Seventeen high fat samples were, thus, combined with the Example 2 77 calibration samples to generate a 94 sample, fat-expanded calibration data set. A fat-expanded model was developed using the same preprocessing spectra transformations used in Example 2. Calibration was performed using modified PLS regression. The modification to PLS scaled the reference data and reflectance data at each wavelength to have a standard deviation of 1.0 before each PLS regression term. the optimum number of PLS factors used for total dietary fiber prediction was determined by cross validation. During cross validation one sixth of the calibration samples at a time was temporarily removed from the calibration set and used for prediction and performance statistics were accumulated for each group of removed samples. The optimal number of factors for total dietary fiber was that which produced a minimum in overall error between modeled and reference values (SECV). The preprocessing transformations were the optimum required to improve the SECV compared to PLS analysis with untransformed data.

NIR Calibration on the Fat- and Sugar-expanded Calibration Data Set. A fourth model was developed using both the high fat calibration expansion samples (n=20) used above and the high sugar calibration expansion samples from a previous report (n=37). Three spectral outliers were previously identified among the high sugar samples, two in the calibration data set and 1 in the validation data set. These were not included in the present data set. As described for the sugar-expanded model of example 2 and the fat-expanded model above, a SELECT algorithm was used to select representative high fat samples and high sugar samples, from the pool of 57, for calibration expansion. Eleven components were used for selection. Seventeen high fat and 23 high sugar samples were selected and were combined with the 77 samples from the sugar expanded model to generate a 117 sample fat- and sugar-expanded data set. $Log_{10}$ 1/R spectra were transformed and centered, as described for the fat-expanded data set, and a fat- and sugar-expanded calibration model developed using modified PLS with the same preprocessing spectra transformations used for the fat-expanded calibration model.

Model Validation. Each model was tested using the Example 2 30 independent validation samples, plus 10 new independent high fat samples for the fat-expanded model and plus 10 independent high fat samples and 14 independent high sugar samples for the fat- and sugar-expanded model. The fat- and sugar-expanded NIR model was also tested using independent cereal samples with both high fat and high sugar content (n=5) and with milled cereal samples having a wide range in moisture content i.e. milled cereal products subjected to 4 relative humidity treatments, 20, 60, and 80% relative humidity and a vacuum oven, as described by Windham, et al. (1997). Performance of models was reported as the standard error of performance (SEP), coefficient of determination ($r^2$), slope and bias (Hruschka, 1987).

RESULTS

Total dietary fiber measured by the reference method. The range for total dietary fiber in all cereal samples (including the Example 2 model), determined by the AOAC enzymatic-gravimetric procedure was from 0.6–52.1% (N=188). For the high fat samples the range in total dietary fiber for the calibration and validation data sets was from 2.3–10.9% and 2.1–7.4%, respectively. The distribution of high fat samples used for calibration expansion for each grain type is given in Table 8 and for the calibration data set in Table 9. The range, mean, and standard derivation of total dietary fiber percent for each grain type is also presented. The standard error of the AOAC laboratory determinations was 0.73% for the Example 2 samples, 0.36% for the high fat samples and 0.88% for the high sugar samples.

TABLE 8

High Fat Cereal and Grain Products Used to Expand the Calibration Data Set. The Range, Mean and Standard Deviation (SD) of Total Dietary Fiber (TDF) Percent.

| Samples | Product Type | Number of Products | Range in TDF % | Mean TDF % | SD TDF % |
| --- | --- | --- | --- | --- | --- |
| high fat | wheat | 8 | 2.0–9.6 | 5.1 | 3.3 |
| | oats | 3 | 4.8–7.9 | 6.3 | 1.5 |
| | corn | 1 | 6.1 | | |
| | multiple grain | 5 | 4.0–10.9 | 6.9 | 3.0 |

Grains represented in multiple grains products in the high fat sample set are: Wheat (4), oats (3), corn (2), rice (2), rye (1), barley (1). The number of products of each grain type is in parentheses.

TABLE 9

High Fat Cereal and Grain Products Used to Expand the Validation Data Set. The Range, Mean, and Standard Deviation (SD) of Total Dietary Fiber (TDF) Percent

| Product Type | Number of Products | Range in TDF % | Mean TDF % | SD TDF % |
| --- | --- | --- | --- | --- |
| wheat | 6 | 2.1–7.4 | 4.5 | 1.8 |
| oats | 3 | 6.3–7.3 | 6.7 | 0.5 |
| corn | 1 | 5.2 | | |

Figure 12:
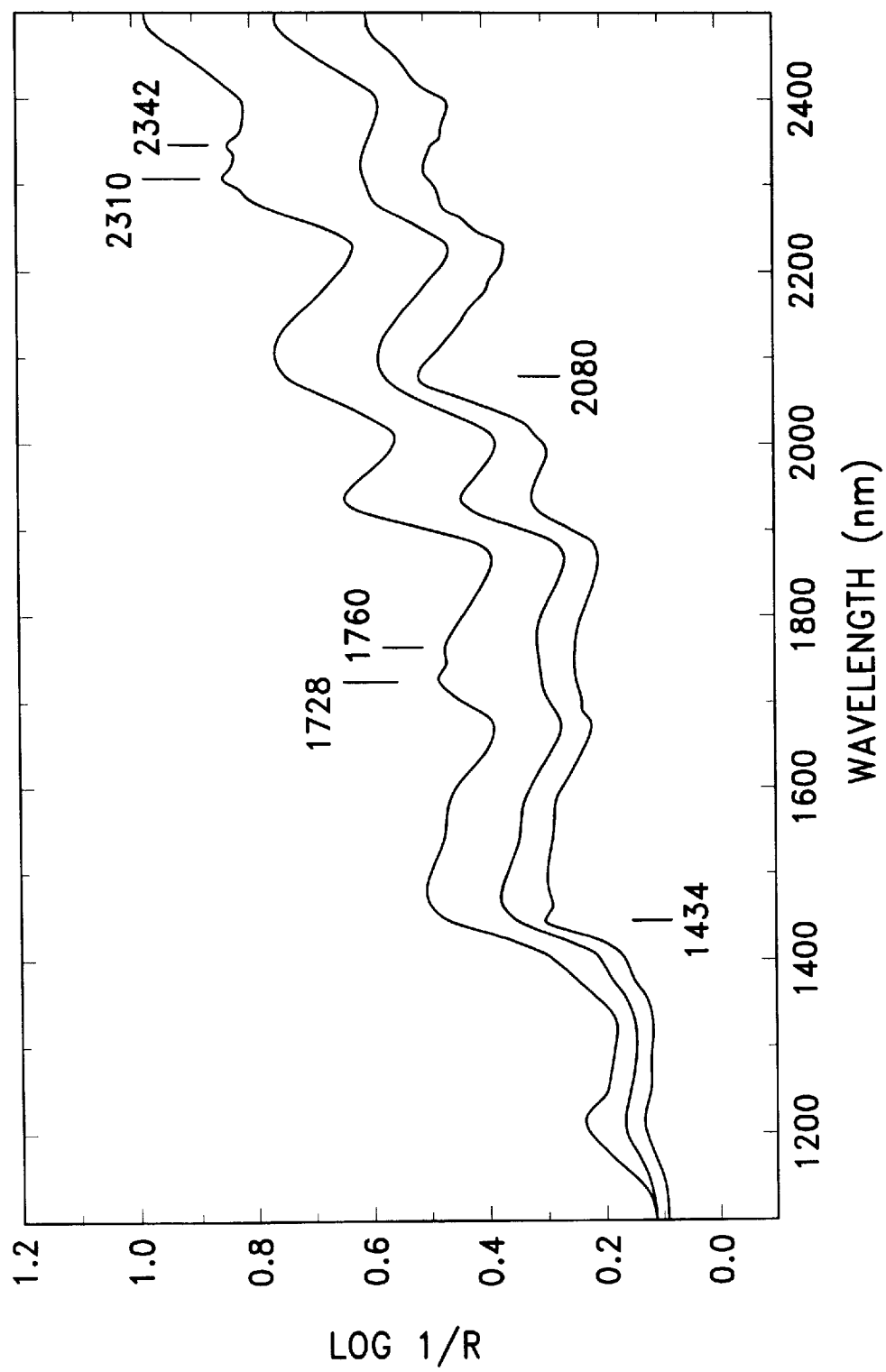
FIG. 12 shows near-infrared spectra of a high fat cereal product (14% fat, 2% sugar, upper plot), low fat low sugar cereal product (0% fat, 9% sugar, middle plot), and high sugar cereal product (3% fat, 47% sugar, lower plot)

Spectral characteristics of samples. NIR spectra of specific cereal samples are presented in FIG. 12. The upper spectrum is of a high fat cereal which has low fat (0%) and low sugar (9%). The lower spectrum of the high fat sample differs from the other spectra in FIG. 12 due to two sets of double bands, at 1728 to 1760 nm and 2310 to 2342 nm, characteristic of absorbance for C—H stretch groups present in lipids. the spectrum of the high sugar sample differs from the other two spectra due to sharp absorbance peaks at 1434 and 2078 nm.

Fat-expanded NIR Calibration Model for Total Dietary Fiber. The fat-expanded calibration data Bet contained cereal products with a range of fat content from high (>10 fat) to medium and low. A NIR calibration was obtained, using modified PLS, for the prediction of total dietary fiber in cereal products with a wide range in fat content. Using 6 cross validation groups, the SECV for the fat-expanded model was 1.75% and $R^2$ 0.98 (Table 10). Linear regression of AOAC determined dietary fiber against NIR predicted dietary fiber (Y=0.14+1.00X) gave an intercept and slope not significantly different from 0.0 and 1.0, respectively (p>0.05). When 10 independent high fat validation samples were combined with the original Example 2 30 independent validation samples and predicted with the high fat model the SEP was 1.77%, $r^2$ 0.98, and bias 0.51 (Table 10). The intercept and slope of the linear regression line, plotting AOAC determined versus NIR predicted dietary fiber for the validation samples (Y=0.24+1.02X), were not significantly different from 0.0 and 0.1, respectively (p>0.05). A comparison of AOAC values versus NIR predicted values for total dietary fiber using the Example 2 model and the fat-expanded model is presented in Table 11. When the original Example 2 model was used to predict the high fat validation samples there was marked over prediction of total dietary fiber. The high fat model corrected this deficiency. The high fat model was used to predict the Example 2 validation samples (n=30) alone with a resulting standard error of performance, $r^2$, bias and slope of 1.87%, 0.98%, 0.36% and 1.04, respectively.

Figure 13A:
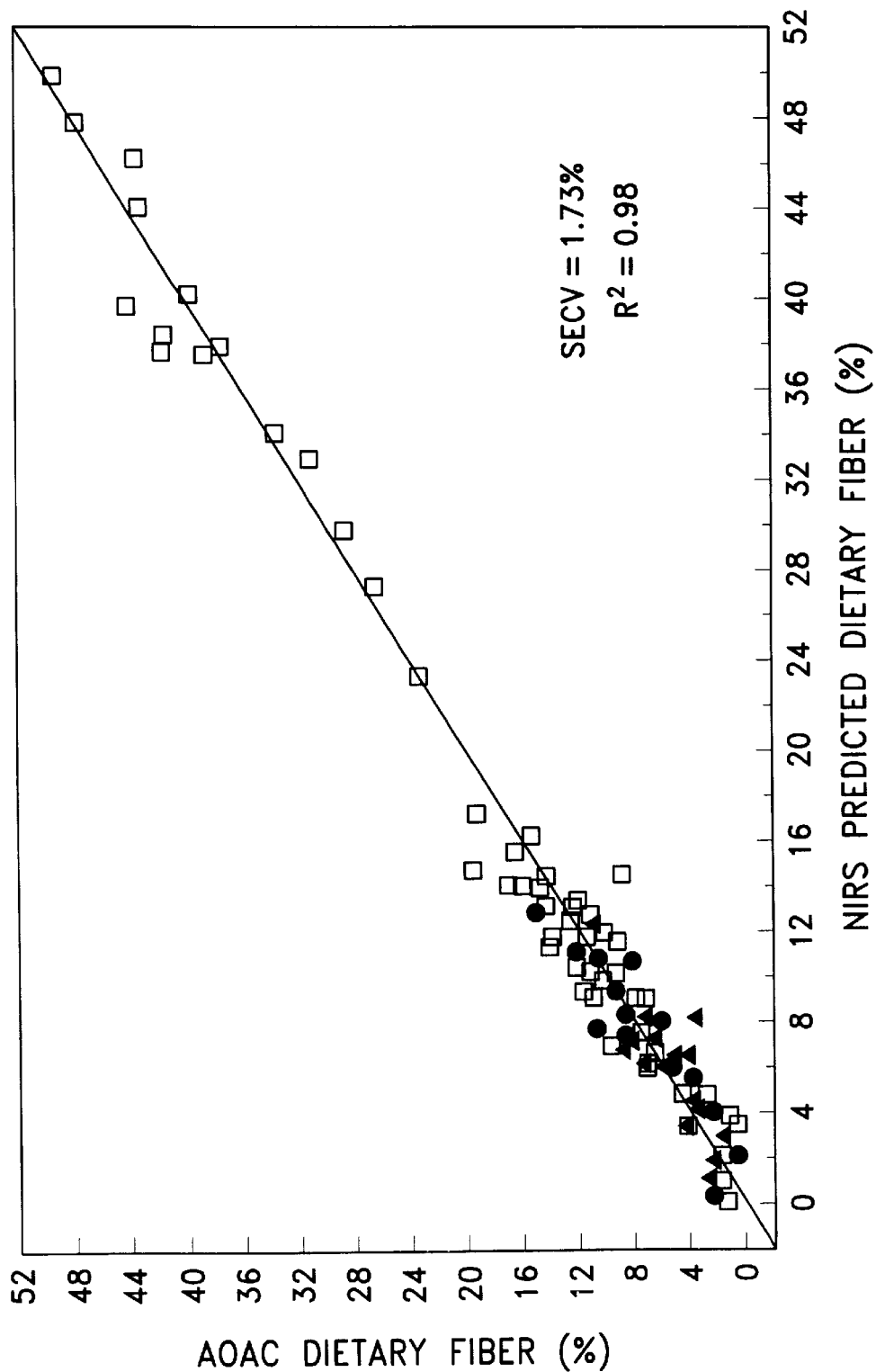
FIG. 13 shows AOAC determined dietary fiber versus NIR-predicted total dietary fiber for cereal products in the calibration data set (n=117, A) and independent validation data set (n=54, B) of the fat- and sugar-expanded model. Open squares represent original cereal samples, solid triangles represent high fat samples (>10% fat), and solid circles represent high sugar samples (>20% sugar)
Figure 13B:
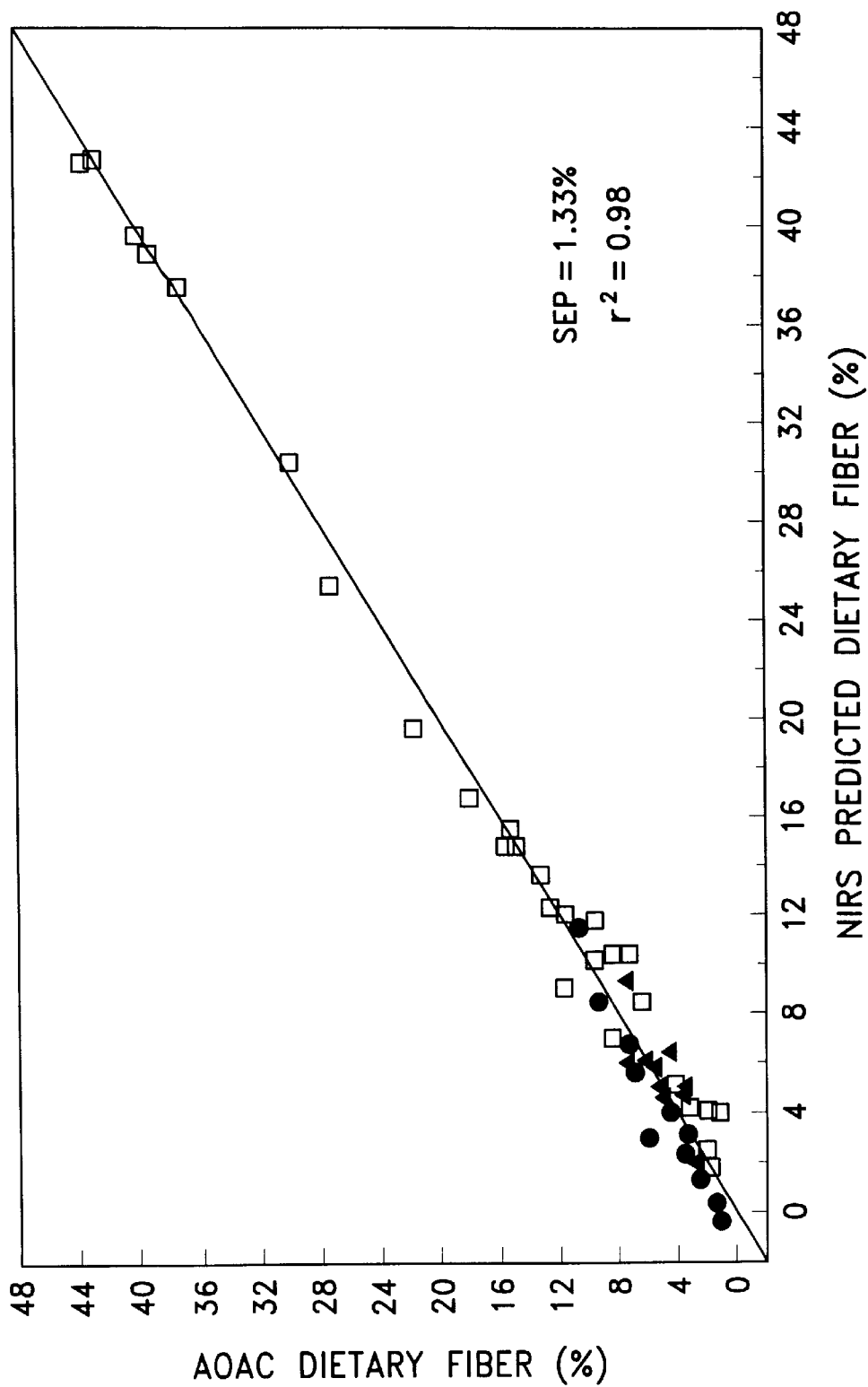

Fat- and Sugar-expanded Calibration Model for Total Dietary Fiber. The fat- and sugar-expanded calibration data set contained cereal products with a broad range of fat content and a broad range of sugar and crystalline sugar content. Thus a NIR model was obtained, using modified PLS, for prediction of total dietary fiber in cereal products with a wide range in fat and sugar content. Using 6 cross validation groups, the SECV for the fat- and sugar-expanded model was 1.73% and $R^2$ 0.98 (Table 10). Linear regression of AOAC determined dietary fiber versus NIR predicted dietary fiber (Y=0.14+1.01X) gave an intercept and slope not significantly different from 0.0 and 1.0, respectively (p>0.05, FIG. 13A). The combined model was tested using the Example 2 30 validation samples plus the 10 high fat and 14 high sugar validation samples. The SEP, $r^2$, and bias were 1.33%, 0.98 and 0.25, respectively. Linear regression of AOAC determined versus NIR predicted dietary fiber for the validation samples (Y+0.21+1.00X) gave an intercept and slope not significantly different from 0.0 and 1.0, respectively (p>0.05), FIG. 13B). When the Example 2 model was used for prediction of total dietary fiber in the Example 2 validation samples plus the 10 high fat and 14 high sugar validation samples, the SEP, $r^2$, bias, and slope were 5.59%, 0.81, 0.15%, and 0.8 respectively. The large SEP was due to marked over prediction of the high fat samples and marked under-prediction of samples containing crystalline sugar (Table 11). A comparison of AOAC values versus NIR predicted values using the Example 2 model and the fat- and sugar-extended model for the corresponding validation samples is presented in Table 11. Data is also included in Table 11 showing prediction, by the Example 2 model and the fat- and sugar-expanded model of total dietary fiber in cereal products (n=5) containing both high fat and high sugar. The Example 2 model markedly over-predicted the total dietary fiber content of 4 of the 5 samples in this category. Whereas, the fat- and sugar-expanded model resulted in correct predictions. When the Example 2 validation samples alone (n=30) are predicted by the combined model the resulting SEP, $r^2$, bias and slope, are 1.40%, 0.98, −0.05%, and 1.03.

Performance of the fat- and sugar-expanded model was tested with spectra of independent validation samples of variable moisture content. Spectra of milled cereal products (n=27) conditioned at 20%, 60%, and 80% relative humidity and in a vacuum oven were utilized. The resulting SEP, $r^2$, bias and slope were 2.09%, 0.98, −0.55%, and 1.12. The large SEP was due to samples stored in the vacuum oven and some of the samples stored at 80% relative humidity. In general these samples were over-predicted, resulting in a large overall negative bias for each of these groups. The overall bias for samples conditioned in the vacuum oven was −1.23%. These samples had a residual moisture range of 1.19–2.85% with mean±SD of 2.30±0.34%. The overall bias was −0.77% for samples conditioned at 80% relative humidity. These samples had a residual moisture range of 12.86–16.21% and mean±SD of 15.11±1.13%. The residual moisture range and mean±SD of milled cereal samples used in the fat- and sugar-expanded calibration data set (n=117) was 3.03–12.89% and 7.34±2.57%, respectively, and for the validation data set (n=54) was 3.31–12.2% and 6.69±2.32%, respectively. Thus, total dietary fiber is predicted well in cereal samples with moisture content within the moisture range of the samples in the calibration.

PLS Loadings. The fat-expanded model employed 8 factors which explained 98.4% of the spectral variation. Sample scores having the highest correlation with dietary fiber were for factors 1, 2, and 3 with correlation coefficients of 0.56, 0.72 and 0.38, respectively.

Figure 14A:
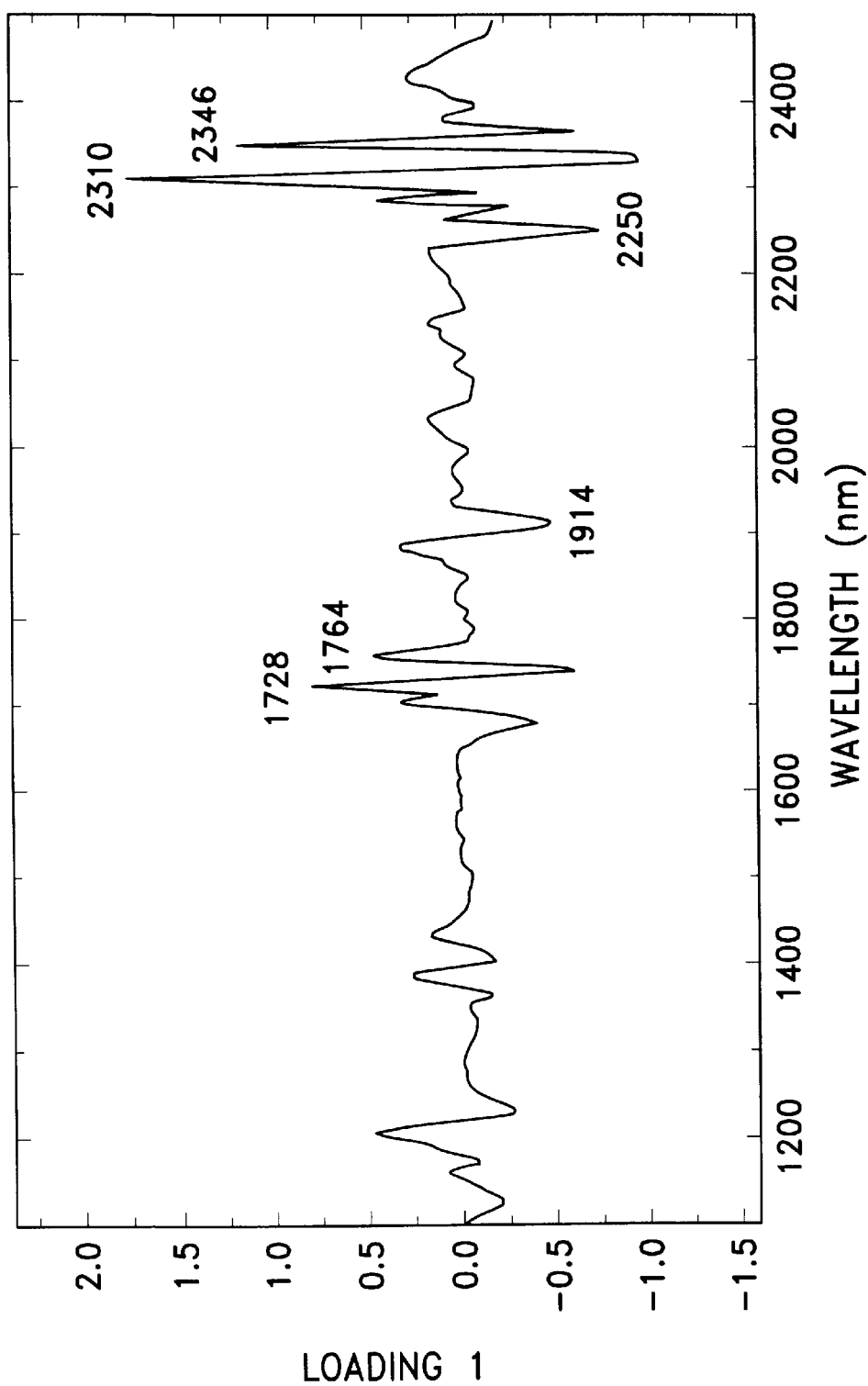
FIG. 14 shows PLS loading spectra for total dietary fiber in cereal products in the fat-expanded model. Panels A, B and C represent loadings for factors 1, 2 and 3, respectively.
Figure 14B:
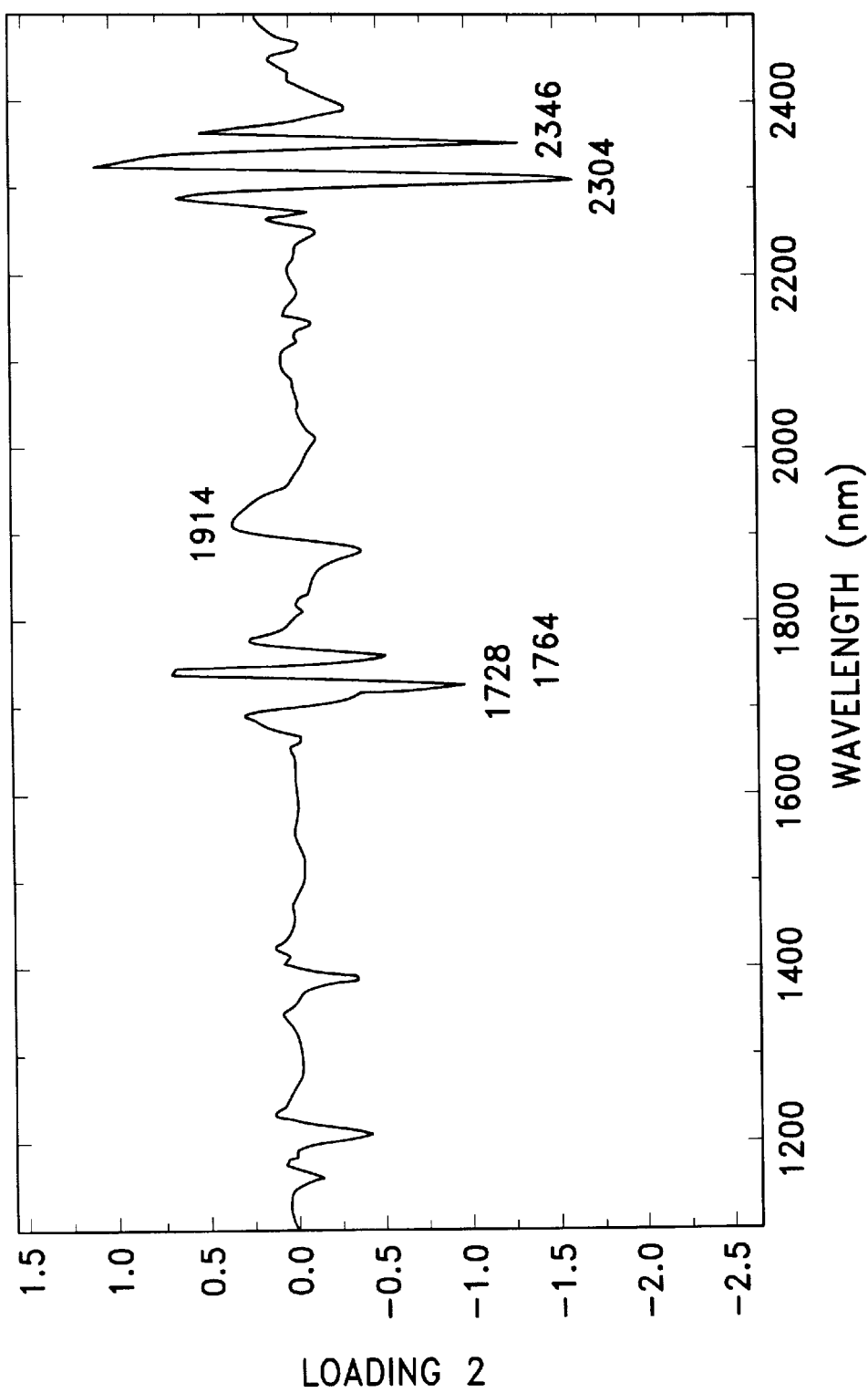
Figure 14C:
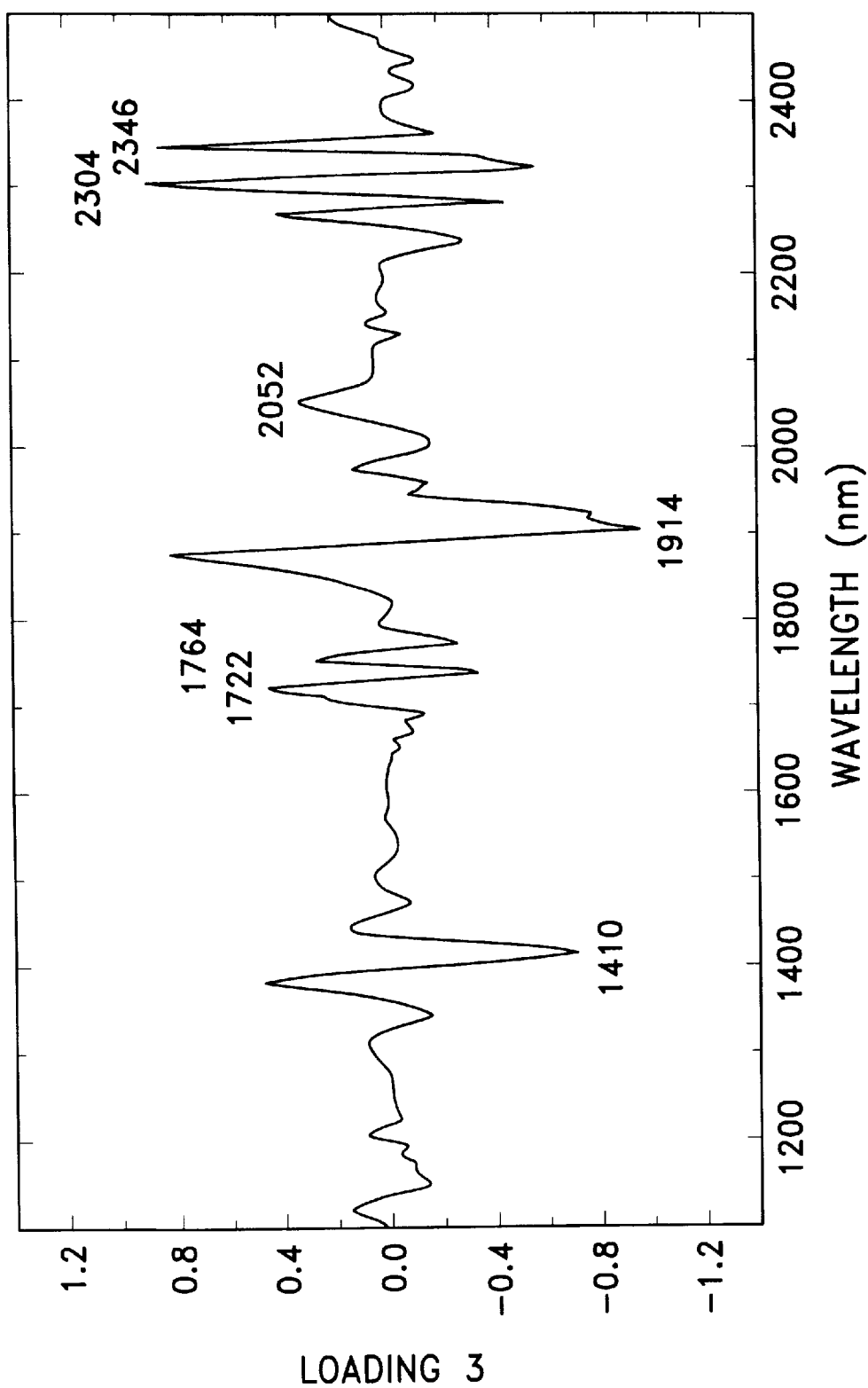

PLS loading plots show the regression coefficients of each wavelength to dietary fiber for each factor and can indicate which wavelengths have the highest variation in a calibration set. Wavelengths of high variation may be associated with areas of the spectrum of known chemical origin. The fat-expanded data set and the fat- and sugar-expanded data set appear to have loadings of high relative positive or negative values primarily at wavelengths that are associated with lipid and carbohydrate, respectively. Key values in loadings may be associated with known vibrations and together with the correlation of individual loadings with fiber, fat, or sugar an estimate may be obtained of which chemical component is the primary contributor for each loading. Factor 2 of the fat expanded model was the most highly correlated to dietary fiber and had a loading with the greatest absorbances at 1728, 1764, 2304, and 2346 nm, associated with absorbance of C—H stretch groups in lipid (FIG. 3B). The first loading was the second most highly correlated to dietary fiber and its loading plot also has the most prominent absorption peaks in the spectral regions associated with C—H stretch groups of lipid (FIG. 14A). The third PLS loading has absorption bands associated with C—H stretch groups of lipid in addition to O—H groups of the water band at 1410 and 1914 and amide groups in the protein region at 2052 n, (FIG. 14C). Overall the constituent having the greatest influence in the high fat model appears to be lipid via C—H stretch absorbance. Other influences appear to be from carbohydrate at 2286 and 2250 nm and water at 1914 and 1410 nm.

Figure 15A:
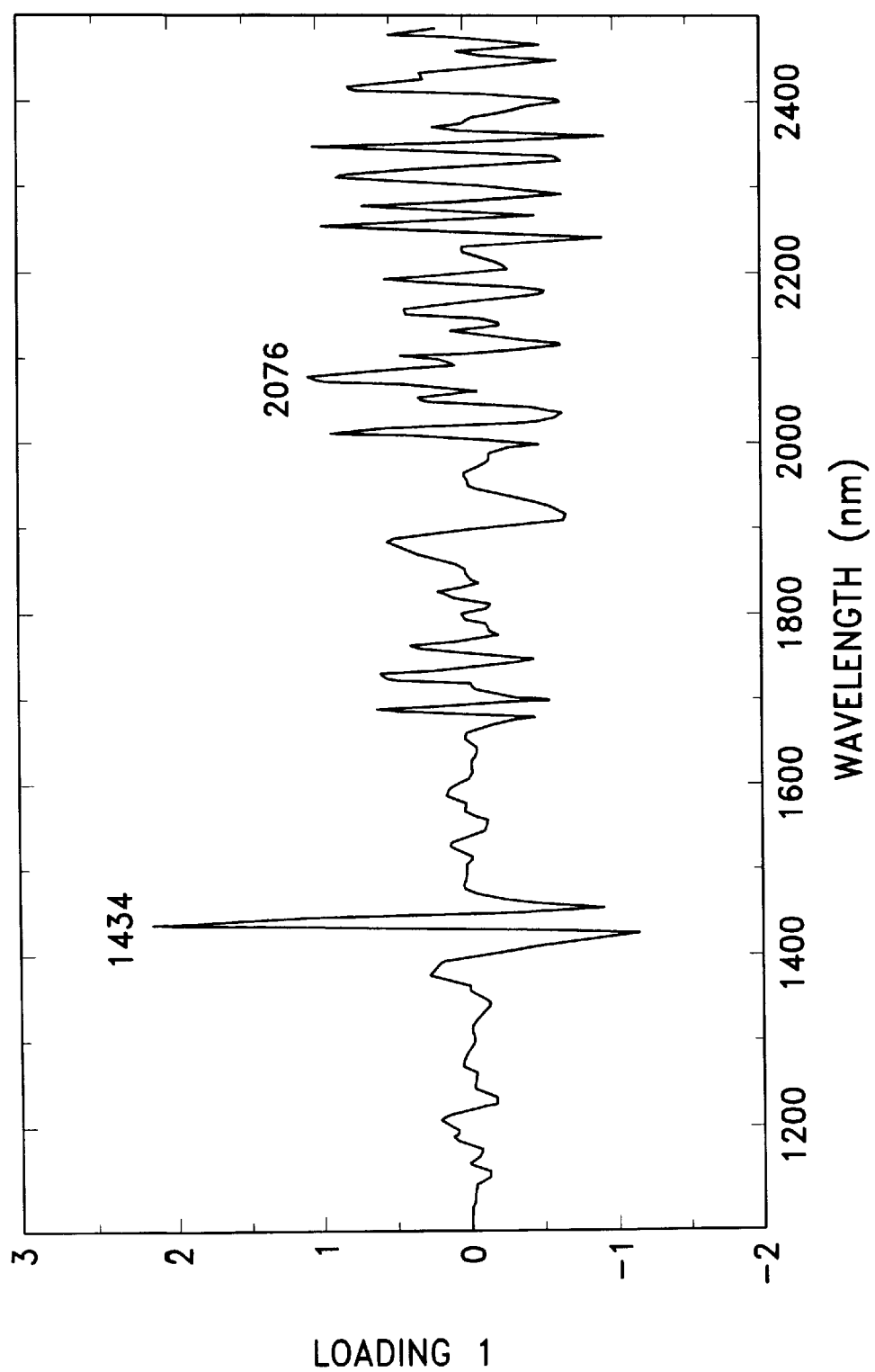
FIG. 15 shows PLS loading spectra for total dietary fiber in cereal products in the fat- and sugar-expanded model. Panels A, B and C represent loadings for factors 1, 2 and 3 respectively.
Figure 15B:
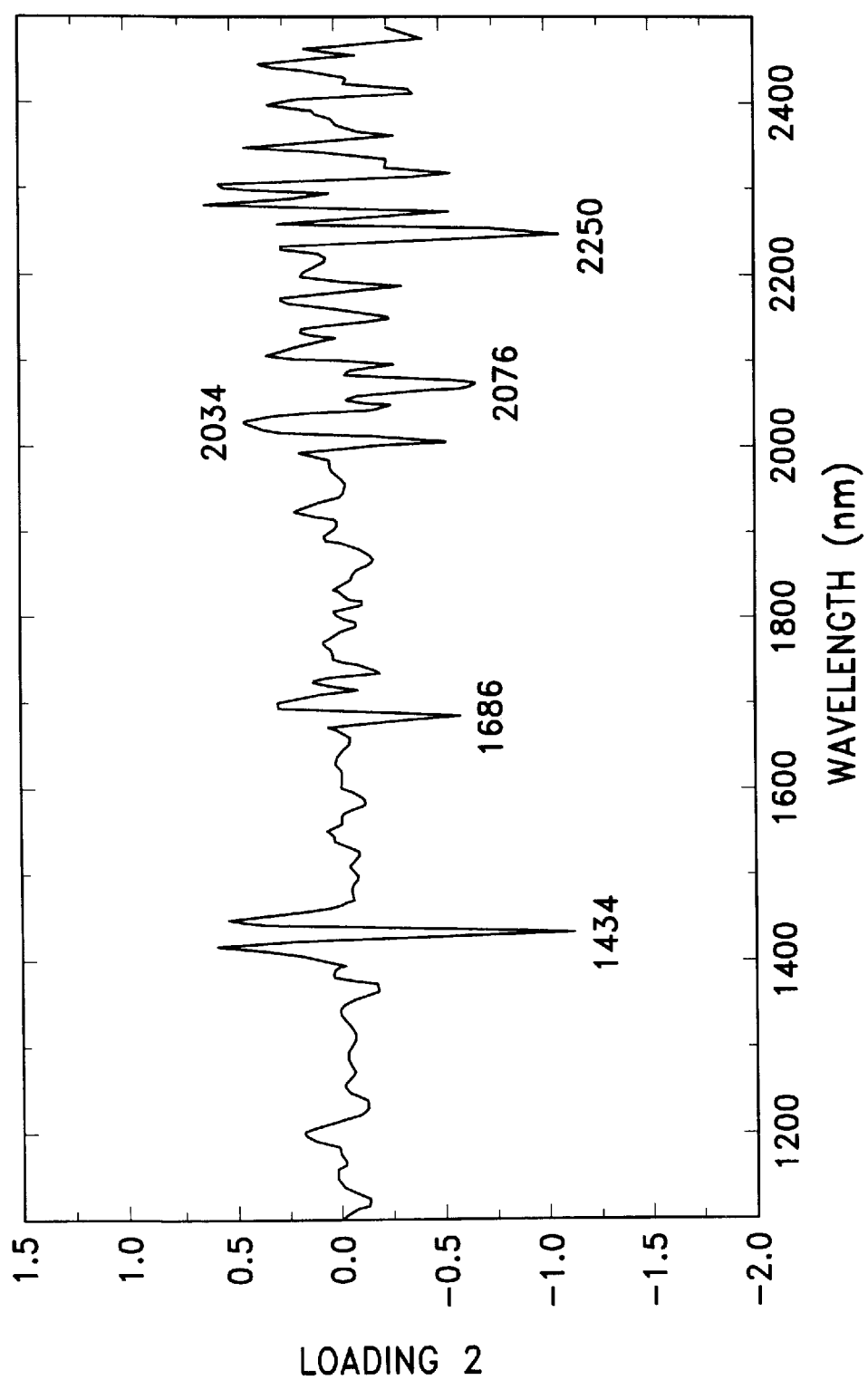
Figure 15C:
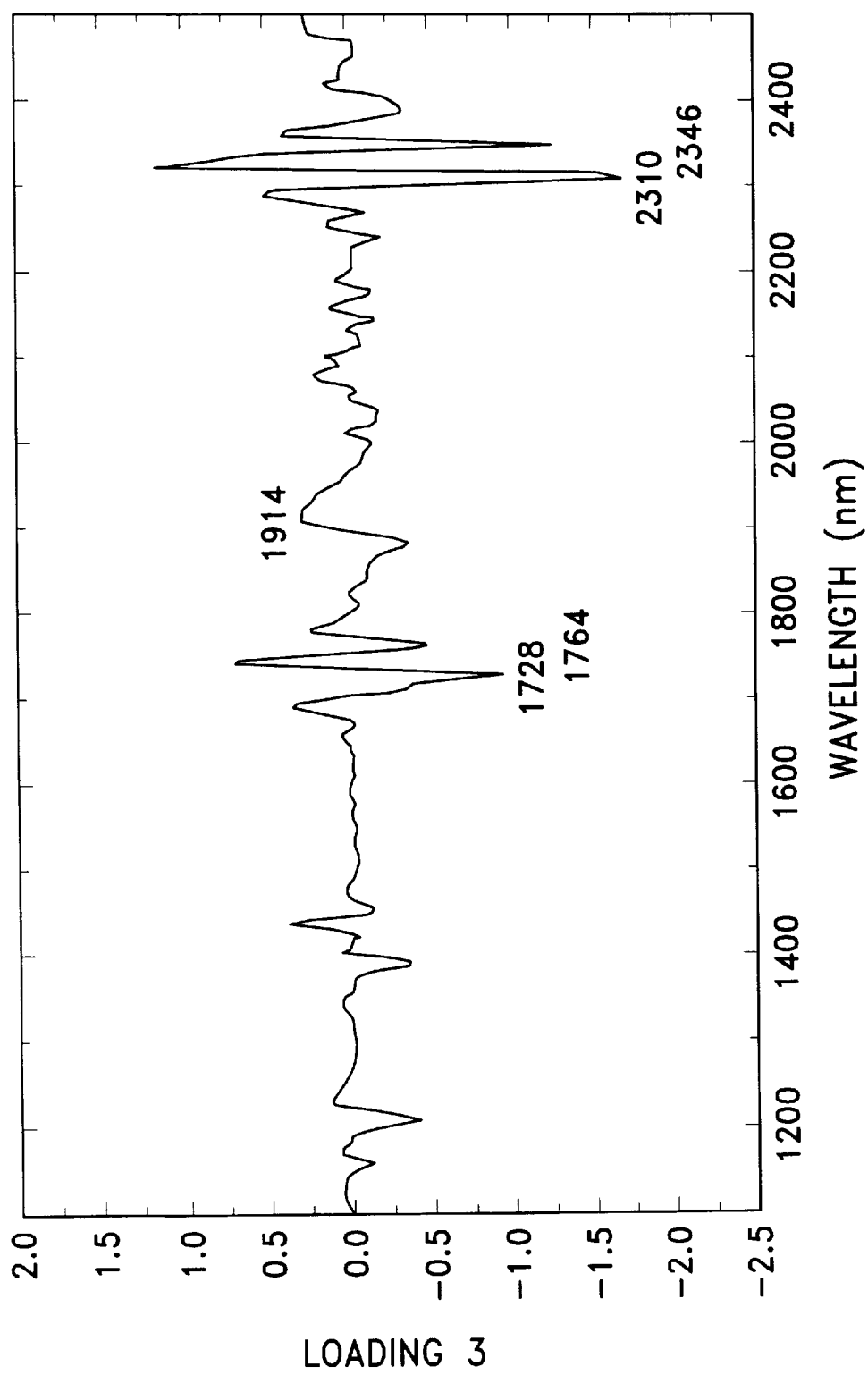

The fat- and sugar-expanded model utilized 9 factors which accounted for 98.1% of the spectral variation. Sample scores having the highest correlation with dietary fiber were for factors 1, 2, and 3 with correlation coefficients of 0.46, 0.79, and 0.31, respectively. The second factor of the combined model was the most highly correlated to dietary fiber and its loading had a sharp absorbance peak at 1434 n, (FIG. 15B), similar to that in loadings 1 and 2 of the high sugar model of Example 2. Peaks also occurred in the second loading for the fat- and sugar-expanded model at 2076 and 2250 nm suggesting absorption by groups in carbohydrate. The loading for the first factor (second most highly correlated to dietary fiber, FIG. 15) had a major absorbance peak at 1434 nm and smaller peaks at 1914 correlated to O—H absorbance in the water band, at 2076 correlated to O—H absorbance in mono- or disaccharides, and from 2200 to 2300 nm a region often associated with C—H groups in carbohydrates. The loading for the third factor had principle areas of absorption at 1728, 1764, 2310, and 2346 nm typical of C—H stretch groups in lipid (FIG. 15C). The fat- and sugar-expanded model was predominantly influenced by carbohydrate with minor influences due to lipid and water.

Figure 16A:
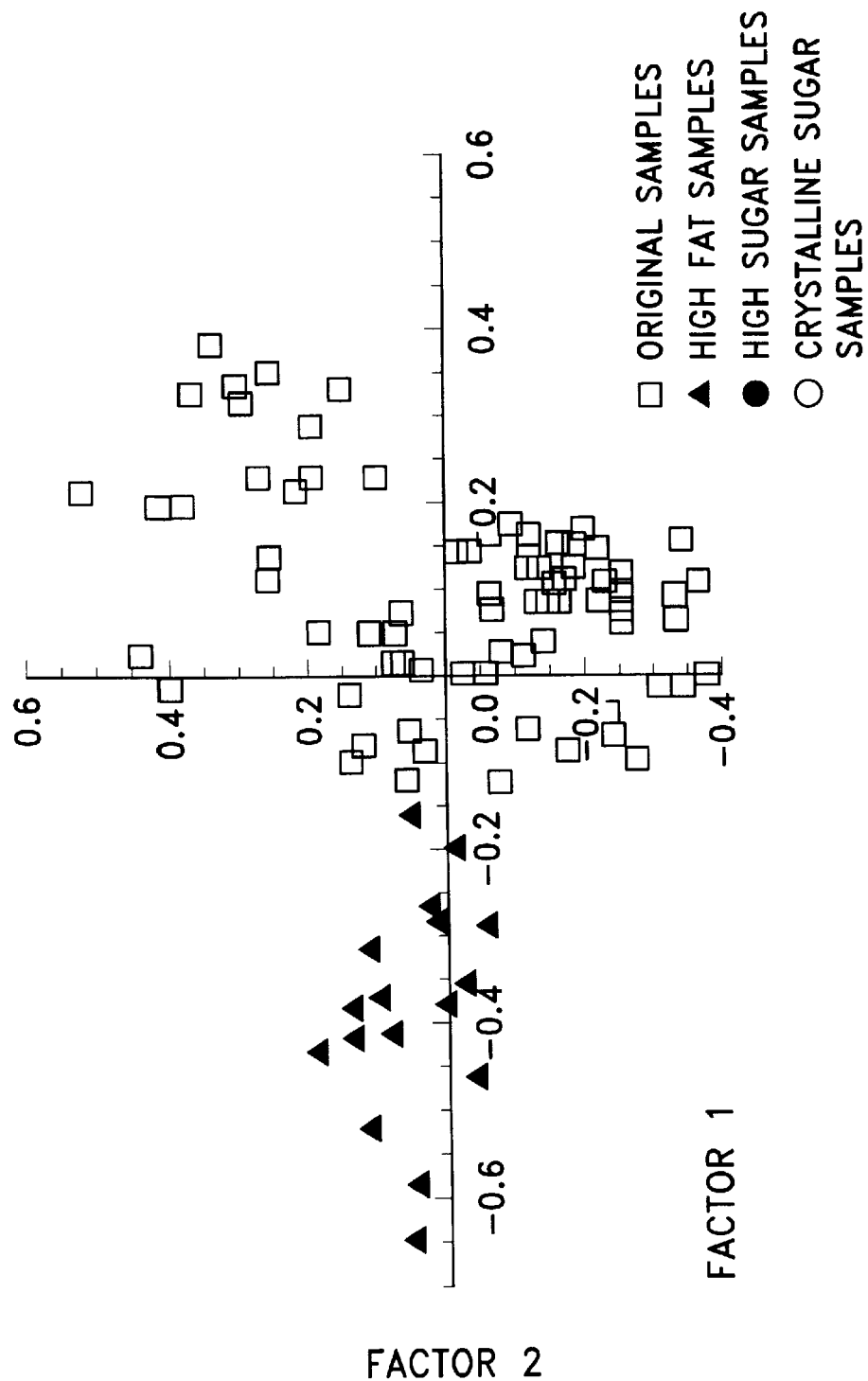
FIG. 16 shows plots of the PLS scores for factor 1 versus factor 2 for the fat-expanded model (A) and the fat- and sugar-expanded model (B).
Figure 16B:
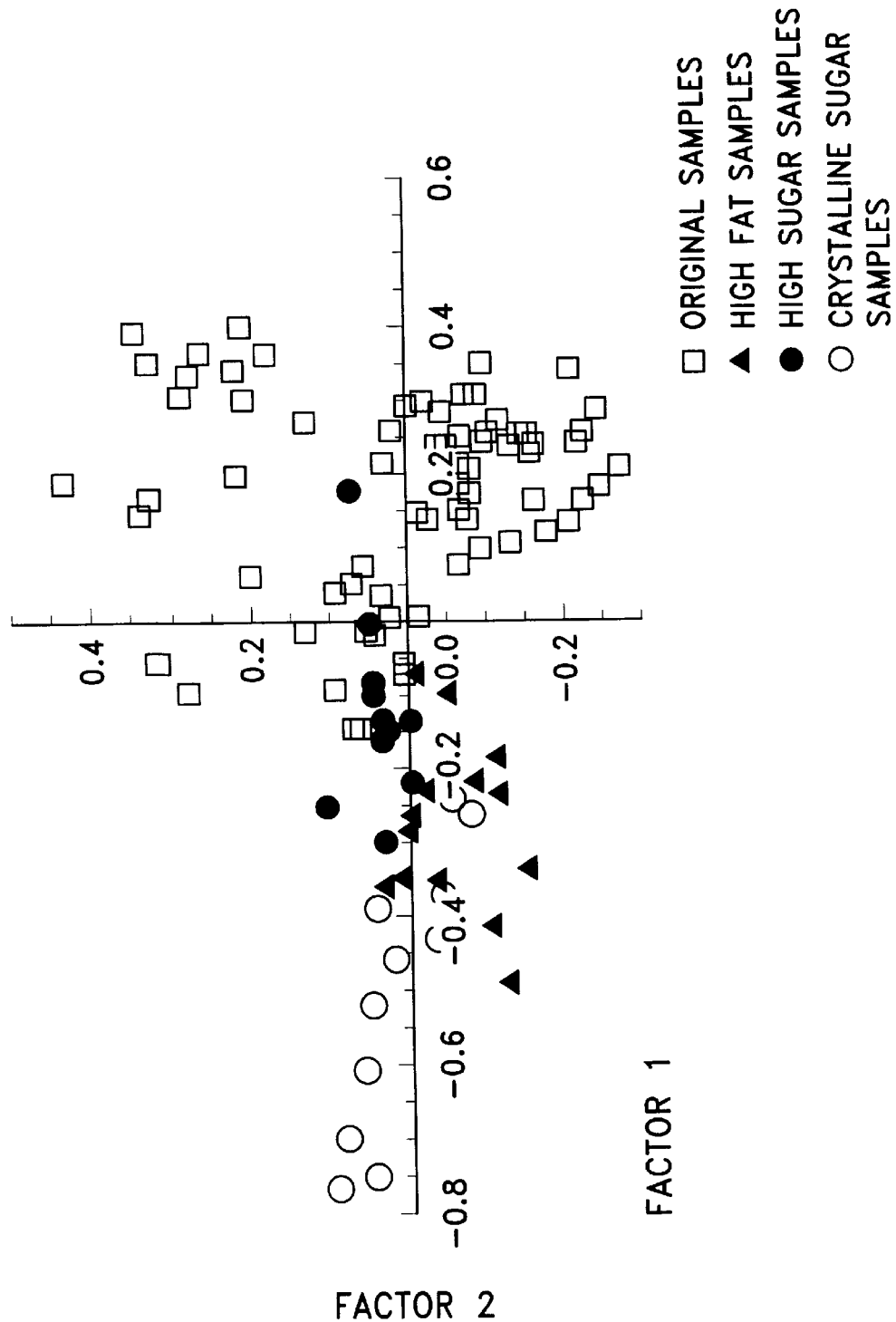

PLS Scores. Plots of factor 1 versus factor 2 scores for dietary fiber are represented in FIG. 16, panels A and B. For the fat-expanded model, fat content, based upon product nutrition label values, appears to be a significant contributor to factor 1 (Pearson Correlation Coefficient 0.85) resulting in distribution of samples of high to low fat content along the factor 1 axis (FIG. 16A). The predominant contribution to factor 2 appears to be dietary fiber (Pearson Correlation Coefficient 0.72). For the fat- and sugar-expanded model the predominant contributor to factor 1 appears to be sugar content, based on product nutrient label values (Pearson's Correlation Coefficient −0.73). As in the sugar-expanded model of Example 2 the crystalline sugar samples, which in general contain the largest amount of sugar, are visualized along the factor 1 axis (FIG. 16B). For factor 2 the major contribution appears to be from dietary fiber (Pearson's Correlation Coefficient o.79). Fat content did not appear to make a substantial contribution to any of the factors in the fat- and sugar-expanded model, based on Pearson Correlation Coefficients.

Accordingly, the model was expanded to include cereal products with high fat content. The fat-expanded model had a similar level of accuracy to the original model of Example 2 (standard error of cross validation 1.75%, $R^2$ 0.98). The model was also expanded to include both high fat and high sugar products. As with the previous models, the fat- and sugar-expanded model encompasses a broad range of cereal products such as breakfast cereals, crackers, brans, flours, pastas, cookies, and a broad range of grains, wheat, oats, barley, rye, corn, millet, amaranth, and products containing multiple grains. In addition, the fat- and sugar-expanded model encompasses products with a wide range in fat content, sugar content, and crystalline sugar content. The fat- and sugar-expanded model had a similar standard error of cross validation to the Example 2 model and was found to accurately predict total dietary fiber in an independent group of samples also with a broad range of product types, grains, fat content, and sugar content. The standard error of cross validation, standard error of performance, bias, slope, and coefficients of determination observed indicate a high degree of precision and reliability in determining dietary fiber using the fat- and sugar-expanded calibration.

Examination of the loadings in the fat- and sugar-combined calibration equation suggests that effects due to O—H and C—H groups in carbohydrate regions are most important in the model. The loadings for the 2 factors most highly correlated to dietary fiber have significant intensity in these regions (1434, 2076, and 2200–2300 nm). It is only in the loading plot for the third factor that significant intensity associated with absorbance by C—H stretch groups in lipid was observed. This loading is very similar to loading 2 of the fat-expanded model. Overall, the fat- and sugar-expanded model appears to be influenced by carbohydrate with minor influences from lipid, water, and protein. This is in contrast to the fat-expanded model where the major influence is from lipid with O—H bands in water evident in the loading for factor 3. Loadings for factor 1 and 2 of the fat- and sugar-extended model very closely resemble the loadings of factors 1 and 2 for the high sugar model of Example 2. In both models the loadings are dominated by sharp bands at 1434 and 2076 nm. The shape and positioning of these bands is indicative of the importance of O—H groups in crystalline sugar in development of these models.

TABLE 10

Calibration and Validation Statistics for Dietary Fiber Prediction by the Fat-expanded and Fat- and Sugar-expanded NIR Models[a]

| Model | Method | | Calibration | | | | | Validation[b] | | | | |
|---|---|---|---|---|---|---|---|---|---|---|---|---|
| | | n | Mean | SD | SECV | $R^2$ | n | Mean | SD | SEP | $r^2$ | Bias | Slope |
| fat expanded | AOAC | 94 | 14.02 | 13.03 | | | 40 | 12.93 | 12.53 | | | | |
| | NIRS | 94 | 14.10 | 12.82 | 1.75 | 0.98 | 40 | 12.43 | 12.16 | 1.77 | 0.98 | 0.51 | 1.02 |
| Fat- and Sugar-expanded | AOAC | 117 | 12.59 | 12.13 | | | 54 | 10.98 | 11.48 | | | | |
| | NIRS | 117 | 12.63 | 11.91 | 1.73 | 0.98 | 54 | 10.74 | 11.37 | 1.32 | 0.99 | 0.25 | 1.00 |

[a]Mean, standard deviation (SD), standard error of cross validation (SECV), and multiple coefficient of determination ($R^2$). Mean, standard deviation, standard error of performance (SEP), coefficient of determination ($r^2$), bias, and slope for validation.
[b]Independent validation samples (n = 40) used to test the fat-expanded model consisted of cereal samples with low fat and sugar (n = 30) plus samples with high fat (>10% fat, n = 10). Independent validation samples (n = 54) used to test the fat- and sugar-expanded model consisted of cereal samples with low fat and sugar (n = 30), plus cereal samples with high fat (>10% fat, n = 10), and cereal samples with high sugar (>20% sugar, n = 14).

TABLE 11

NIR Prediction of Total Dietary Fiber in Cereal Products

| | | NIR Predicted TDF %[a] | | |
|---|---|---|---|---|
| Products | AOAC TDF % | Original model[b] | Fat-expanded model | Fat- and sugar-expanded model |
| High Fat | | | | |
| Wild Blueberry Granola | 7.32 | 15.80 | 5.48 | 5.67 |
| Wheatables | 5.50 | 12.28 | 5.67 | 5.54 |
| Harvest Crisps | 4.46 | 6.76 | 3.50 | 4.52 |
| Cinnamon Grahams | 3.07 | 3.00 | 1.47 | 1.78 |
| Wheatsworth Crackers | 4.52 | 11.25 | 5.29 | 6.01 |
| Waverly Crackers | 2.10 | 6.57 | −0.33 | 1.50 |
| Blue Corn Chips | 5.23 | 19.81 | 4.06 | 4.68 |
| Vegetable Crackers | 7.36 | 10.55 | 8.21 | 9.11 |
| Super Nutty Granola | 6.28 | 16.62 | 4.69 | 5.72 |
| Cashew Almond Granola | 6.59 | 13.07 | 5.07 | 5.57 |
| High Sugar | | | | |
| Fruit and Fiber | 10.58 | 15.93 | — | 11.25 |
| Healthy Choice | 9.36 | 11.31 | — | 8.18 |
| Golden Crisp | 3.59 | 9.37 | — | 4.78 |
| Honey Grahams | 4.80 | 4.52 | — | 2.91 |
| Oatmeal Crunch | 4.52 | 4.18 | — | 3.67 |
| Blueberry Morning | 3.38 | 3.89 | — | 2.86 |
| Golden Grahams | 3.54 | 3.33 | — | 2.12 |
| Honey Nut Cheerios* | 7.29 | 0.24 | — | 6.35 |
| Nut and Honey Crunch* | 2.45 | −3.97 | — | 1.12 |
| Apple Cinnamon Toasted Oats* | 6.87 | −4.00 | — | 5.33 |
| Honey Crunch Corn Flakes* | 1.84 | −7.09 | — | 0.49 |
| Oat Bran Muffin Mix* | 4.65 | −10.62 | — | 4.28 |
| Double Dip Crunch* | 1.01 | −9.97 | — | −0.50 |
| Cocoa Pebbles* | 1.42 | −17.53 | — | 0.24 |
| High Fat and High Sugar | | | | |
| Oats'n Honey Granola Bars | 5.30 | 16.18 | — | 4.16 |
| 100% Natural Cereal | 6.54 | 15.69 | — | 7.93 |
| Cinnamon Toast Crunch | 3.62 | −1.43 | — | 1.48 |
| Famous Amos Cookies | 3.27 | 14.44 | — | 2.36 |
| Banana Nut Crunch | 5.84 | 11.79 | — | 5.14 |

[a]Total dietary fiber.
[b]Example 2 model.
*Spectral evidence of crystalline sugar Accordingly, using the calibration model according to the present invention, near-infrared reflectance spectroscopy can be used to predict, rapidly and accurately, the total dietary fiber content of a wide range of cereal products. Visual assessment of the spectral loadings suggests that analytically useful absorbance is dominated by effects related to O—H and C—H groups in the water and carbohydrate regions of the spectrum.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A method for determining total dietary fiber by NIRS in a sample containing one or more grains, said method comprising:
   (a) obtaining grain samples having >10% fat and having known dietary fiber content and representative of the range of dietary fiber to be determined;
   (b) milling each of said samples to form milled samples;
   (c) irradiating each of said milled samples with near infrared radiation and digitally recording reflectance intensity at discrete frequencies;
   (d) comparing variations in spectral intensity at said discrete frequencies with known total dietary fiber content for said variety of samples and selecting frequencies at which spectral deviations correlate with total dietary fiber content;
   (e) developing a calibration model based on the results of step (d);
   (f) obtaining a grain sample having >10% fat of which the dietary fiber content is to be determined;
   (g) milling said sample of step (f) to form a milled sample;
   (h) irradiating the milled sample of step (g) with near infrared radiation spectrometer and digitally recording spectral absorbance; and
   (i) determining total dietary fiber by comparing the scan with said calibration model.

2. A method for determining total dietary fiber by NIRS in a sample containing one or more grains, said method comprising:
   (a) obtaining grain samples having >20% sugar and having known dietary fiber content and representative of the range of dietary fiber to be determined;
   (b) milling each of said samples to form milled samples;

(c) irradiating each of said milled samples with near infrared radiation and digitally recording reflectance intensity at discrete frequencies;

(d) comparing variations in spectral intensity at said discrete frequencies with known total dietary fiber content for said variety of samples and selecting frequencies at which spectral deviations correlate with total dietary fiber content;

(e) developing a calibration model based on the results of step (d);

(f) obtaining a grain sample having >20% sugar of which the dietary fiber content is to be determined;

(g) milling said sample of step (f) to form a milled sample;

(h) irradiating the milled sample of step (g) with near infrared radiation spectrometer and digitally recording spectral absorbance; and (i) determining total dietary fiber by comparing the scan with said calibration model.

3. A method for determining total dietary fiber by NIRS in a sample containing one or more grains, said method comprising:

(a) obtaining grain samples having >20% crystalline sugar and having known dietary fiber content and representative of the range of dietary fiber to be determined;

(b) milling each of said samples to form milled samples;

(c) irradiating each of said milled samples with near infrared radiation and digitally recording reflectance intensity at discrete frequencies;

(d) comparing variations in spectral intensity at said discrete frequencies with known total dietary fiber content for said variety of samples and selecting frequencies at which spectral deviations correlate with total dietary fiber content;

(e) developing a calibration model based on the results of step (d);

(f) obtaining a grain sample having >20% crystalline sugar of which the dietary fiber content is to be determined;

(g) milling said sample of step (f) to form a milled sample;

(h) irradiating the milled sample of step (g) with near infrared radiation spectrometer and digitally recording spectral absorbance; and (i) determining total dietary fiber by comparing the scan with said calibration model.

4. A method for determining total dietary fiber by NIRS in a sample containing one or more grains, said method comprising:

(a) obtaining grain samples having >10% fat and >20% sugar and having known dietary fiber content and representative of the range of dietary fiber to be determined;

(b) milling each of said samples to form milled samples;

(c) irradiating each of said milled samples with near infrared radiation and digitally recording reflectance intensity at discrete frequencies;

(d) comparing variations in spectral intensity at said discrete frequencies with known total dietary fiber content for said variety of samples and selecting frequencies at which spectral deviations correlate with total dietary fiber content;

(e) developing a calibration model based on the results of step (d);

(f) obtaining a grain sample having >10% fat and >20% sugar of which the dietary fiber content is to be determined;

(g) milling said sample of step (f) to form a milled sample;

(h) irradiating the milled sample of step (g) with near infrared radiation spectrometer and digitally recording spectral absorbance; and (i) determining total dietary fiber by comparing the scan with said calibration model.

5. A method as in claims 1, 2, 3, or 4, wherein said grain samples of step (a) include at least 5 species of grain.

6. A method as in claims 1, 2, 3, or 4, wherein the spectra is recorded in step (c) at from about 5 to about 1,051 frequencies.

7. A method as in claim 6, wherein said spectra are recorded at from 100 to 800 frequencies.

8. A method as in claims 1, 2, 3, or 4, wherein said frequency selection in step (d) is by Principal Component Analysis.

9. A method as in claims 1, 2, 3, or 4, wherein spectra for each sample are transformed to $\log_{10}(1/R)$ spectra.

10. A method as in claims 1, 2, 3, or 4, wherein spectral intensity recorded in step (c) is transformed to $\log_{10}(1/R)$ spectra in absorbance units, and wherein said transformed data is processed using Partial Least Squares (PLS) regression for formation of said calibration model.

11. A method as in claim 10, wherein said PLS regression is modified PLS regression, the modification comprising scaling the reference method data and reflectance data at each wavelength to have a standard deviation 1.0 before each PLS regression term.

12. A method as in claim 10, wherein said $\log_{10}(1/R)$ spectra are transformed with normal variate and detrending procedures to remove multiplicative interferences of scatter, and then transformed with second derivative processing to enhance absorption peaks.

13. A method as in claims 1, 2, 3, or 4, wherein said scanning is from 1100 to 2498 nm.

14. A method as in claims 1, 2, 3, or 4, wherein said scanning is with a near infrared scanning monochromator.

15. A method as in claims 1, 2, 3, or 4, further including the step of pretreating the set of calibration data to remove and compensate for spectral artifacts prior to the step of processing the set of calibration data.

16. A method as in claim 15, wherein the step of pretreating the set of calibration data is performed using an algorithm selected from the group consisting of nth order derivatives, multiplicative scatter correction, n-point smoothing, mean centering, variance scaling, and ratiometric method.

17. A calibration model for determining total dietary fiber by NIRS in a sample containing one or more grains, said calibration model obtained by a method comprising:

(a) obtaining grain samples having >10% fat and having known dietary fiber content and representative of the range of dietary fiber to be determined;

(b) milling each of said samples to form milled samples;

(c) irradiating each of said milled samples with near infrared radiation and digitally recording reflectance intensity at discrete frequencies;

(d) comparing variations in spectral intensity at said discrete frequencies with known total dietary fiber content for said variety of samples and selecting frequencies at which spectral deviations correlate with total dietary fiber content;

(e) developing a calibration model based on the results of step (d);

(f) obtaining a grain sample having >10% fat of which the dietary fiber content is to be determined;

(g) milling said sample of step (f) to form a milled sample;

(h) irradiating the milled sample of step (g) with near infrared radiation spectrometer and digitally recording spectral absorbance; and (i) determining total dietary fiber by comparing the scan with said calibration model.

18. A calibration model for determining total dietary fiber by NIRS in a sample containing one or more grains, said calibration model obtained by a method comprising:

(a) obtaining grain samples having >20% sugar and having known dietary fiber content and representative of the range of dietary fiber to be determined;

(b) milling each of said samples to form milled samples;

(c) irradiating each of said milled samples with near infrared radiation and digitally recording reflectance intensity at discrete frequencies;

(d) comparing variations in spectral intensity at said discrete frequencies with known total dietary fiber content for said variety of samples and selecting frequencies at which spectral deviations correlate with total dietary fiber content;

(e) developing a calibration model based on the results of step (d);

(f) obtaining a grain sample having >20% sugar of which the dietary fiber content is to be determined;

(g) milling said sample of step (f) to form a milled sample;

(h) irradiating the milled sample of step (g) with near infrared radiation spectrometer and digitally recording spectral absorbance; and (i) determining total dietary fiber by comparing the scan with said calibration model.

19. A calibration model for determining total dietary fiber by NIRS in a sample containing one or more grains, said calibration model obtained by a method comprising:

(a) obtaining grain samples having >20% crystalline sugar and having known dietary fiber content and representative of the range of dietary fiber to be determined;

(b) milling each of said samples to form milled samples;

(c) irradiating each of said milled samples with near infrared radiation and digitally recording reflectance intensity at discrete frequencies;

(d) comparing variations in spectral intensity at said discrete frequencies with known total dietary fiber content for said variety of samples and selecting frequencies at which spectral deviations correlate with total dietary fiber content;

(e) developing a calibration model based on the results of step (d);

(f) obtaining a grain sample having >20% crystalline sugar of which the dietary fiber content is to be determined;

(g) milling said sample of step (f) to form a milled sample;

(h) irradiating the milled sample of step (g) with near infrared radiation spectrometer and digitally recording spectral absorbance; and (i) determining total dietary fiber by comparing the scan with said calibration model.

20. A calibration model for determining total dietary fiber by NIRS in a sample containing one or more grains, said calibration model obtained by a method comprising:

(a) obtaining grain samples having >10% fat and >20% sugar and having known dietary fiber content and representative of the range of dietary fiber to be determined;

(b) milling each of said samples to form milled samples;

(c) irradiating each of said milled samples with near infrared radiation and digitally recording reflectance intensity at discrete frequencies;

(d) comparing variations in spectral intensity at said discrete frequencies with known total dietary fiber content for said variety of samples and selecting frequencies at which spectral deviations correlate with total dietary fiber content;

(e) developing a calibration model based on the results of step (d);

(f) obtaining a grain sample having >10% fat and >20% sugar of which the dietary fiber content is to be determined;

(g) milling said sample of step (f) to form a milled sample;

(h) irradiating the milled sample of step (g) with near infrared radiation spectrometer and digitally recording spectral absorbance; and (i) determining total dietary fiber by comparing the scan with said calibration model.

* * * * *